United States Patent [19]
Campbell et al.

[11] Patent Number: 4,710,507
[45] Date of Patent: Dec. 1, 1987

[54] QUINOLONE INOTROPIC AGENTS

[75] Inventors: Simon F. Campbell, Deal; David A. Roberts, Sandwich, both of England

[73] Assignee: Pfizer Inc., New York, N.Y.

[21] Appl. No.: 683,440

[22] Filed: Dec. 18, 1984

[30] Foreign Application Priority Data

Dec. 22, 1983 [GB] United Kingdom ............... 8334282
Jul. 6, 1984 [GB] United Kingdom ............... 8417340

[51] Int. Cl.⁴ .................. A61K 31/47; C07D 215/18; C07D 215/22
[52] U.S. Cl. .................. 514/312; 546/157; 546/158
[58] Field of Search ............... 546/158, 157; 514/312

[56] References Cited

U.S. PATENT DOCUMENTS

| | | | |
|---|---|---|---|
| 3,907,808 | 9/1975 | Lesher | 546/156 |
| 3,962,445 | 6/1976 | Buckle | 514/312 |
| 3,993,656 | 11/1976 | Rooney | 260/296 N |
| 4,258,185 | 3/1981 | Nakao et al. | 544/114 |

FOREIGN PATENT DOCUMENTS

| | | |
|---|---|---|
| 0052016 | 5/1982 | European Pat. Off. |
| 0102046 | 3/1984 | European Pat. Off. |
| 7973783 | 6/1979 | Japan |
| 2086896 | 5/1982 | United Kingdom |

OTHER PUBLICATIONS

Tominaga, PCT/JP81/00328 (5/27/82).

*Primary Examiner*—Sidney Marantz
*Assistant Examiner*—Robert Benson
*Attorney, Agent, or Firm*—Peter C. Richardson; Lawrence C. Akers; Mark Dryer

[57] ABSTRACT

A heterocyclic-substituted 2-quinolone compound of the formula:

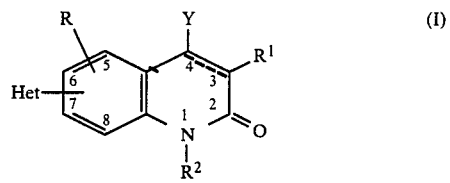

or a pharmaceutically-acceptable salt thereof, wherein "Het" is an optionally substituted 5-or 6-membered monocyclid aromatic heterocyclic group attached by a carbon atom to the 5-, 6-, 7- or 8- position of the quinolone nucleus; R, which is attached to the 5-, 6-, 7- or 8- position, is hydrogen, $C_1$–$C_4$ alkyl, $C_1$–$C_4$ alkoxy, $C_1$–$C_4$ alkylthio, $C_1$–$C_4$ alkylsulphinyl, $C_1$–$C_4$ alkylsulphonyl, halo, $CF_3$, hydroxy, hydroxymethyl, or cyano; $R^1$ is hydrogen, cyano ($C_1$–$C_4$ alkoxy)carbonyl, $C_1$–$C_4$ alkyl, nitro, halo, $-NR^3R^4$ or $-CONR^3R^4$ where each of $R^3$ and $R^4$ is hydrogen or $C_1$–$C_4$ alkyl or $R^3$ and $R^4$ together with the nitrogen atom to which they are attached form a saturated 5- or 6-membered heterocyclic group optionally containing a further heteroatom or group selected from O, S and N—$R^5$ where $R^5$ is hydrogen or $C_1$–$C_4$ alkyl; $R^2$ is hydrogen, $C_1$–$C_4$ alkyl, or 2-hydroxyethyl; Y is hydrogen or $C_1$–$C_4$ alkyl; and the dotted line between the 3- and 4- positions represents an optional bond. The compounds are inotropic agents useful as cardiac stimulants in the treatment of congestive heart failure.

6 Claims, No Drawings

QUINOLONE INOTROPIC AGENTS

BACKGROUND OF THE INVENTION

This invention relates to heterocyclic-substituted 2-quinolone compounds. These compounds are cardiac stimulants which in general selectively increase the force of myocardial contraction without producing significant increases in the heart rate. The compounds are useful in the curative or prophylactic treatment of cardiac conditions, in particular heart failure.

Substituted quinolone derivatives are known in the art and certain of these prior art compounds have been suggested for pharmaceutical use.

For example, Japanese Patent Application No. 79-73783 published June 13, 1979 discloses pyridine-substituted quinolone derivatives of the general formula:

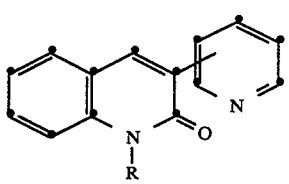

wherein R is a lower alkyl group or phenyl-alkyl group. These compounds are stated to be useful as anti-ulcer agents and hypertensive drugs, but there is no evidence of any inotropic activity.

United Kingdom Patent Application No. 2127402A, published Apr. 11, 1984, discloses certain carbostyril derivatives of the formula:

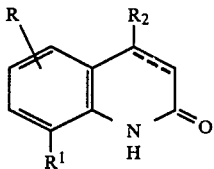

wherein one of R, $R^1$ and $R^2$ is a substituted pyridyl group and the other two are hydrogen atoms or certain substituent groups. These compounds are stated to be useful in the prophylaxis or treatment of thromboses, as coronary vasodilators, as hypotensive agents and as phosphodiesterase inhibitors.

United Kingdom Patent Application No. 2086896A, published May 19, 1982, discloses carbostyril compounds of the formula:

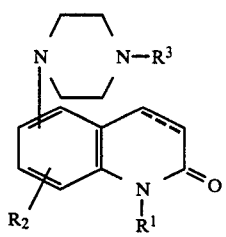

wherein each of $R^1$, $R^2$ and $R^3$ is a hydrogen atom or an organic substituent. These compounds are stated to have cardiotonic activity.

U.S. Pat. No. 4,258,185 discloses certain pyridazinone compounds which include, inter alia, compounds of the formula:

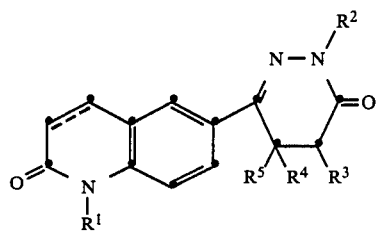

wherein each of $R^1$, $R^2$, $R^4$ and $R^5$ is a hydrogen atom or an organic substituent and $R^3$ is a hydrogen atom or $R^3$ and one of $R^4$ and $R^5$ together form a single bond. The compounds are stated to be therapeutically useful as antithrombotic and antihypertensive drugs.

It has now been found that certain substituted 2-quinolone compounds which differ structurally from the above prior art compounds are useful cardiac stimulants in the treatment of congestive heart failure.

SUMMARY OF THE INVENTION

Thus, according to the present invention there is provided a heterocyclic-substituted 2-quinolone compound having the general formula:

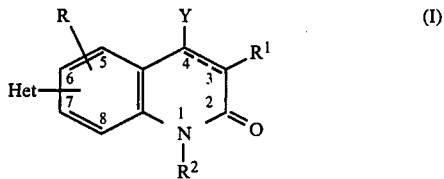

or a pharmaceutically-acceptable salt thereof, wherein "Het" is an optionally substituted 5- or 6-membered monocyclic aromatic heterocyclic group attached by a carbon atom to the 5-, 6-, 7- or 8-position of the quinolone nucleus; R, which is attached to the 5-, 6-, 7- or 8-position, is hydrogen, $C_1$-$C_4$ alkyl, $C_1$-$C_4$ alkoxy, $C_1$-$C_4$ alkylthio, $C_1C_4$ alkyl-sulphinyl, $C_1$-$C_4$ alkylsulphonyl, halo $CF_3$, hydroxy, hydroxymethyl or cyano; $R^1$ is hydrogen, cyano, ($C_1$-$C_4$ alkoxy)carbonyl, $C_1$-$C_4$ alkyl, nitro, halo, —$NR^3R^4$ or —$CONR^3R^4$ where each of $R^3$ and $R^4$ is hydrodgen or $C_1$-$C_4$ alkyl or $R^3$ and $R^4$ together with the nitrogen atom to which they are attached form a saturated 5- or 6-membered heterocyclic group optionally containing a further heteroatom or group selected from O, S and N—$R^5$ where $R^5$ is hydrogen or $C_1$-$C_4$ alkyl; $R^2$ is hydrogen, $C_1$-$C_4$ alkyl, or 2-hydroxyethyl; Y is hydrogen or $C_1$-$C_4$ alkyl; and the dotted line between the 3- and 4-positions represents an optional bond.

In a particular aspect, R is hydrogen, $C_1$-$C_4$ alkyl, $C_1$-$C_4$ alkoxy, $C_1C_4$ alkylthio, $C_1$-$C_4$ alkylsulphinyl, $C_1$-$C_4$ alkylsulphonyl, halo, $CF_3$ or hydroxy; and Y is hydrogen.

Also, the invention provides intermediates to the compounds of the formula (1) having the formula:

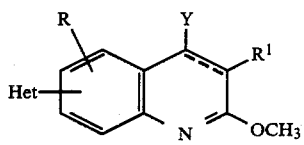

wherein Het, R, $R^1$, Y and the dotted line have the same significance as in formula (I).

In a particular aspect of the invention "Het" is an optionally substituted 5- or 6-membered monocyclic aromatic nitrogen-containing heterocyclic group attached by a carbon atom to the 5-, 6-, 7- or 8-position of said quinolone; R, which is attached to the 5-, 6-, 7- or 8-position, is hydrogen, $C_1$–$C_4$ alkyl or $C_1$–$C_4$ alkoxy; $R^1$ is hydrogen, cyano, ($C_1$–$C_4$ alkoxy)carbonyl, $C_1$–$C_4$ alkyl, —$NR^3R^4$ or —$CONR^3R^4$ where each of $R^3$ and $R^4$ is hydrogen or $C_1$–$C_4$ alkyl or $R^3$ and $R^4$ together with the nitrogen atom to which they are attached form a saturated 5- or 6-membered heterocyclic group optionally containing a further heteroatom or group selected from O, S and N—$R^5$ where $R^5$ is hydrogen or $C_1$–$C_4$ alkyl; $R^2$ is hydrogen, $C_1$–$C_4$ alkyl, or 2-hydroxyethyl; Y is hydrogen; and the dotted line between the 3- and 4-positions represents an optional bond.

Examples of said group "Het" include pyridyl, pyrazinyl, pyrimidinyl, pyridazinyl, imidazolyl, pyrazolyl, oxazolyl, isoxazolyl, thiazolyl, isothiazolyl, triazolyl, tetrazolyl, furyl, thienyl, oxadiazolyl, and, when nitrogen containing, their N-oxides, all being optionally substituted by 1 or 2 substituents each independently selected from, e.g., $C_1$–$C_4$ alkyl, $C_1$–$C_4$ alkoxy, $C_1$–$C_4$ alkylthio, cyano, $CF_3$, halo, —$NR^3R^4$ or —$CONR^3R^4$ where $R^3$ and $R^4$ are as defined for formula (I), hydroxymethyl, and ($C_1$–$C_4$ alkoxy)carbonyl.

The preferred N-oxide is pyridyl-N-oxide.

"Halo" means F, Cl, Br and I. $C_3$ and $C_4$ alkyl and alkoxy groups can be straight or branched chain.

Where $R^3$ and $R^4$ together with the nitrogen atom to which they are attached form said saturated 5- or 6-membered heterocyclic group, examples of this heterocyclic group are 1-pyrrolidinyl, piperidino, morpholino and 4-methylpiperazino.

Although the compounds of the formula (I) are written as 2-(1H)-quinolones, it should be realised that the following tautomerism will occur when $R^2$ hydrogen:

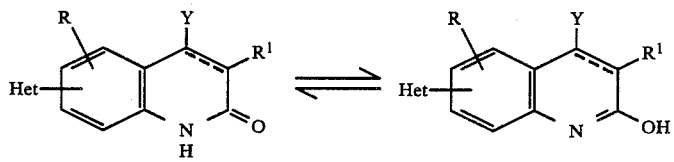

(I, $R^2$ = H)

However, as the keto-form is considered the more stable tautomer, the end products herein will be named and illustrated as quinolones although those skilled in the art will realise that both tautomers may be present or that any particular compound so named may exist predominantly as the hydroxy tautomer and the following disclosure is to be interpreted to incorporate all tautomeric forms.

In the preferred compounds, "Het" is preferably pyridyl, an N-oxide thereof, pyrimidinyl, pyridazinyl, pyrazinyl, imidazolyl, triazolyl, tetrazolyl, thiazolyl, oxadiazolyl, thienyl or furyl, all optionally substituted by 1 or 2 substituents each selected from $C_1$–$C_4$ alkyl, $C_1$–$C_4$ alkoxy, cyano, amino and carbamoyl.

More preferably, "Het" is selected from (a) pyridyl optionally substituted by 1 or 2 methyl groups or by a single methoxy, cyano, amino or carbamoyl group (b) pyridyl-N-oxide (c) pyrimidinyl (d) pyridazinyl (e) pyrazinyl (f) triazolyl or N-methyl triazolyl (g) tetrazolyl or N-(n-butyl)-tetrazolyl (h) N-methylimidazolyl (i) oxadiazolyl (j) thiazolyl (k) thienyl and (l) furyl.

Most preferably, "Het" is pyrid-3-yl, pyrid-4-yl, 2,6-dimethylpyrid-3-yl or 1-methyl-(1H)-1,2,4-triazol-5-yl.

"Het" is preferably attached to the 5-, 6- or 7-position and most preferably to the 6-position.

R is preferably H, $C_1$–$C_4$ alkyl, $C_1$–$C_4$ alkoxy, $C_1$–$C_4$ alkylthio, $C_1$–$C_4$ alkylsulphinyl, $C_1$–$C_4$ alkylsulphonyl, halo, hydroxy or hydroxymethyl. More preferably, R is H, $C_1$–$C_4$ alkyl, methoxy, methylthio, methylsulphinyl, methylsulphonyl, bromo, hydroxy or hydroxymethyl.

When R is a substituent, it is preferably in the 7- or 8-position, most preferably in the 8-position, particularly 8-methyl.

$R^1$ is preferably H, cyano, $C_1$–$C_4$ alkoxycarbonyl, nitro, halo or amino. $R^1$ is more preferably H, cyano, methoxycarbonyl, nitro, bromo or amino. $R^1$ is most preferably H.

$R^2$ is preferably H or $CH_3$, most preferably H.

Y is preferably H or $CH_3$, and most preferably H.

Preferably there is a double bond between the 3- and 4-positions in the quinolone.

The preferred compounds have the structure:

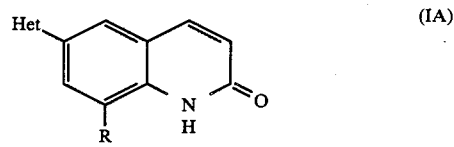

where Het and R are as defined above. "Het" is preferably 2,6-dimethylpyrid-3-yl or 1-methyl-(1H)-1,2,4-triazol-5-yl. R is preferably methyl.

The pharmaceutically-acceptable salts of the compounds of the formula (I) are non-toxic and include acid addition salts such as the hydrochloride, hydrobromide, hydroiodide, sulphate or bisulphate, phosphate or hydrogen phosphate, acetate, maleate, fumarate, lactate, tartrate, citrate, gluconate, mesylate and p-toluenesulphonate salts. Also included are the metal salts, especially the alkali metal and alkaline earth metal salts, particularly the sodium and potassium salts.

The cardiac stimulant activity of the compounds of the formula (I) is shown by their effectiveness in one or more of the following tests: (a) increasing the force of contraction in the "Starling" dog heart-lung preparation measured via a left ventricular catheter; (b) increasing myocardial contractility (left ventricular dp/dt max.) in the anaesthetised dog measured via a left ventricular catheter; (c) increasing myocardial contractility in the conscious dog with an implanted left ventricular transducer (dp/dt max.) or an exteriorised carotid artery loop (systolic time intervals).

In test (a), the positive inotropic effect of the test compound following bolus administration is measured in the "Starling" dog heart-lung preparation. The selectivity for increase in force versus frequency of contraction of the test compound is obtained.

In test (b), the positive inotropic action of the test compound following intravenous administration is measured in the anaesthetised dog. The magnitude and duration of this action, and the selectivity for increase in force versus frequency of contraction of the test compound are obtained, as are the peripheral effects, e.g. the effect on blood pressure.

In test (c) the positive inotropic action of the test compound following intravenous or oral administration to a conscious dog with an implanted left ventricular transducer (dp/dt max.) or an exteriorised carotid artery loop (systolic time intervals) is measured. The magnitude of the inotropic action, the selectivity for increase in force versus frequency of contraction, and the duration of action of the inotropic effect of the test compound are all obtained.

The compounds of the formula (I) can be administered alone but will generally be administered in admixture with a pharmaceutical carrier selected with regard to the intended route of administration and standard pharmaceutical practice. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic.

For administration to man in the curative or prophylactic treatment of cardiac conditions such as congestive heart failure, it is expected that oral dosages of the compounds of the invention will be in the range from 10 mg to 1 g daily, taken in 2 to 4 divided doses per day, for an average adult patient (70 kg). Dosages for intravenous administration would be expected to be within the range 1 to 100 mg per single dose as required, for example in the treatment of acute heart failure. Thus for a typical adult patient, individual tablets or capsules might contain 5 to 100 mg of active compound, in a suitable pharmaceutically acceptable vehicle or carrier. Variations may occur depending on the weight and condition of the subject being treated as will be known to medical practitioners.

Thus the present invention provides a pharmaceutical composition comprising a compound of the formula (I) as defined above or pharmaceutically acceptable salt thereof, together with a pharmaceutically acceptable diluent or carrier.

The invention also provides a method of stimulating the heart of an animal, including a human being, which comprises administering to the animal a compound of formula (I) or pharmaceutically acceptable salt thereof, or a pharmaceutical composition as defined above, in an amount sufficient to stimulate the heart of the animal.

The invention yet further provides a compound of the formula (I) or pharmaceutically acceptable salt thereof, for use in medicine, in particular for use in stimulating the heart of a human being suffering from congestive heart failure.

DETAILED DESCRIPTION OF THE INVENTION

The compounds of the invention may be prepared by a number of routes, including the following:

Route A:

This method for preparing compounds (I) in which $R^2$ is H is illustrated as follows:

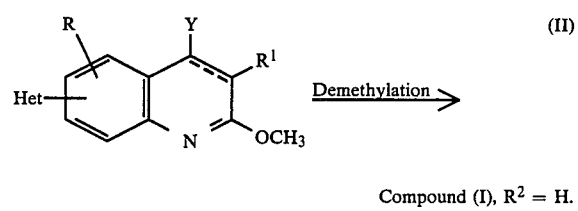

Compound (I), $R^2$ = H.

R, $R^1$, Y, the dotted line and "Het" are as defined for formula (I). The demethylation is preferably carried out by heating the methoxy-quinoline (II) in aqueous mineral acid, preferably aqueous HCl or HBr, and typically in 48% aqueous HBr or 5M aqueous HCl at up to reflux temperature for 0.5–4 hours, or by heating at up to reflux temperature in ethanol containing a catalytic quantity (generally 5–15% by volume) of 48% aqueous HBr. The product can be isolated and purified by conventional procedures.

Typical reactions using 48% aqueous HBr are illustrated as follows:

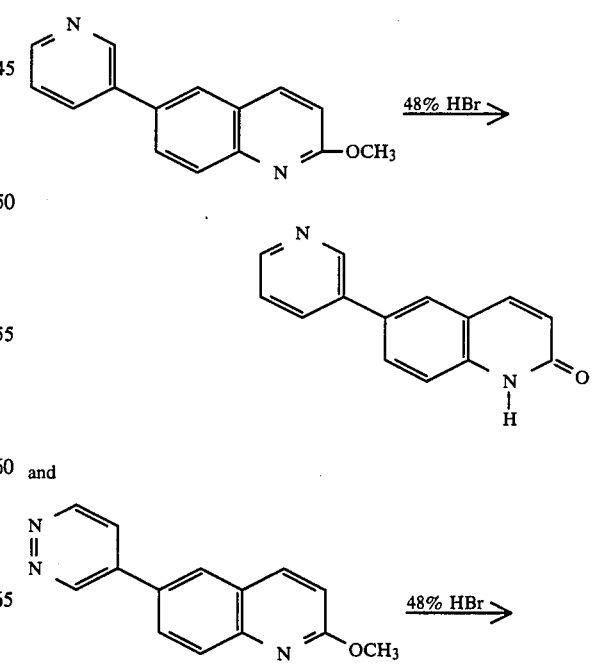

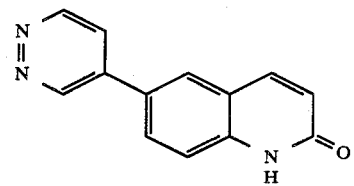
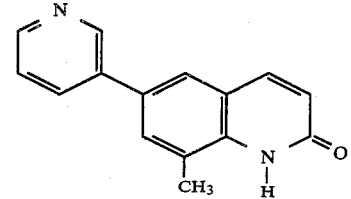
A typical reaction using ethanol containing a catalytic amount of 48% HBr is illustrated as follows:
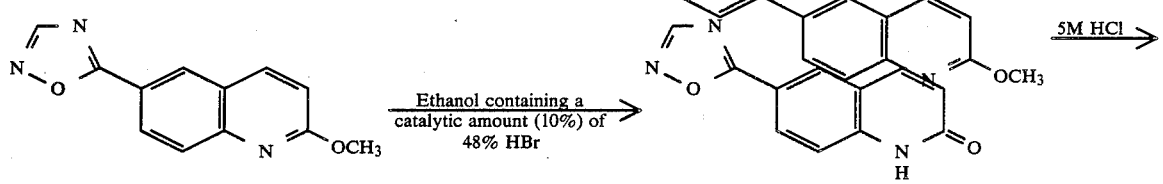
This process can also be carried out using aqueous 5M HCl instead of 48% HBr under similar conditions. Typical reactions using 5M HCl are illustrated as follows:
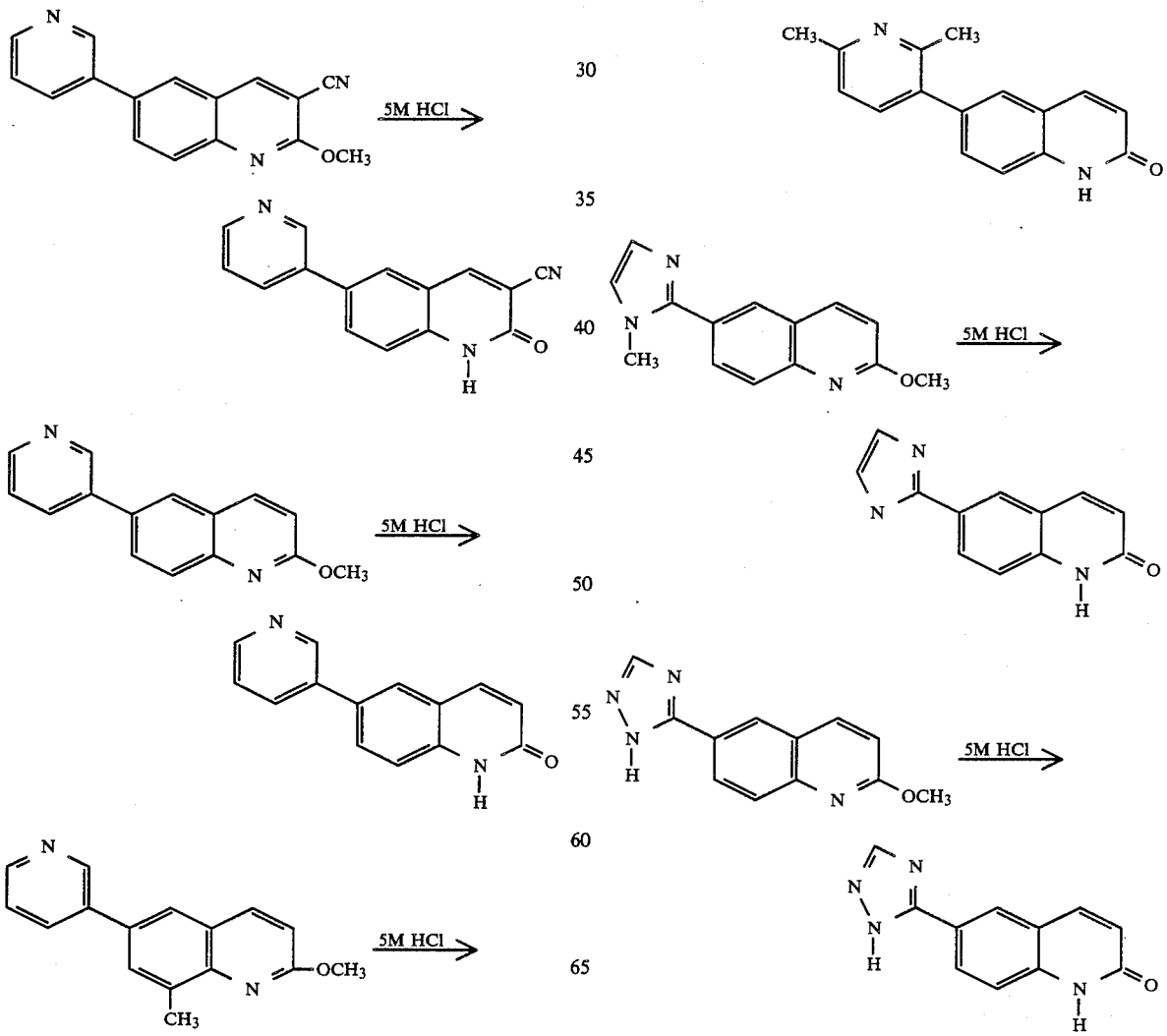

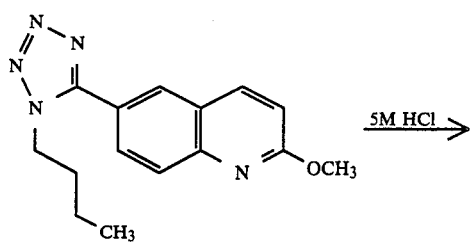

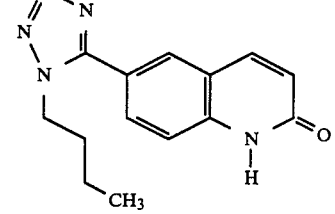

In cases where $R^1$ is an alkoxycarbonyl group (e.g. —COOCH$_3$), the demethylation may convert this group to —COOH, in which case the carboxyl group can be re-esterified conventionally, e.g. using methanol in sulphuric acid.

The starting materials of the formula (II) can again be prepared by conventional procedures. Typical routes to these materials, many of which are illustrated in detail in the following Preparations, are as follows:

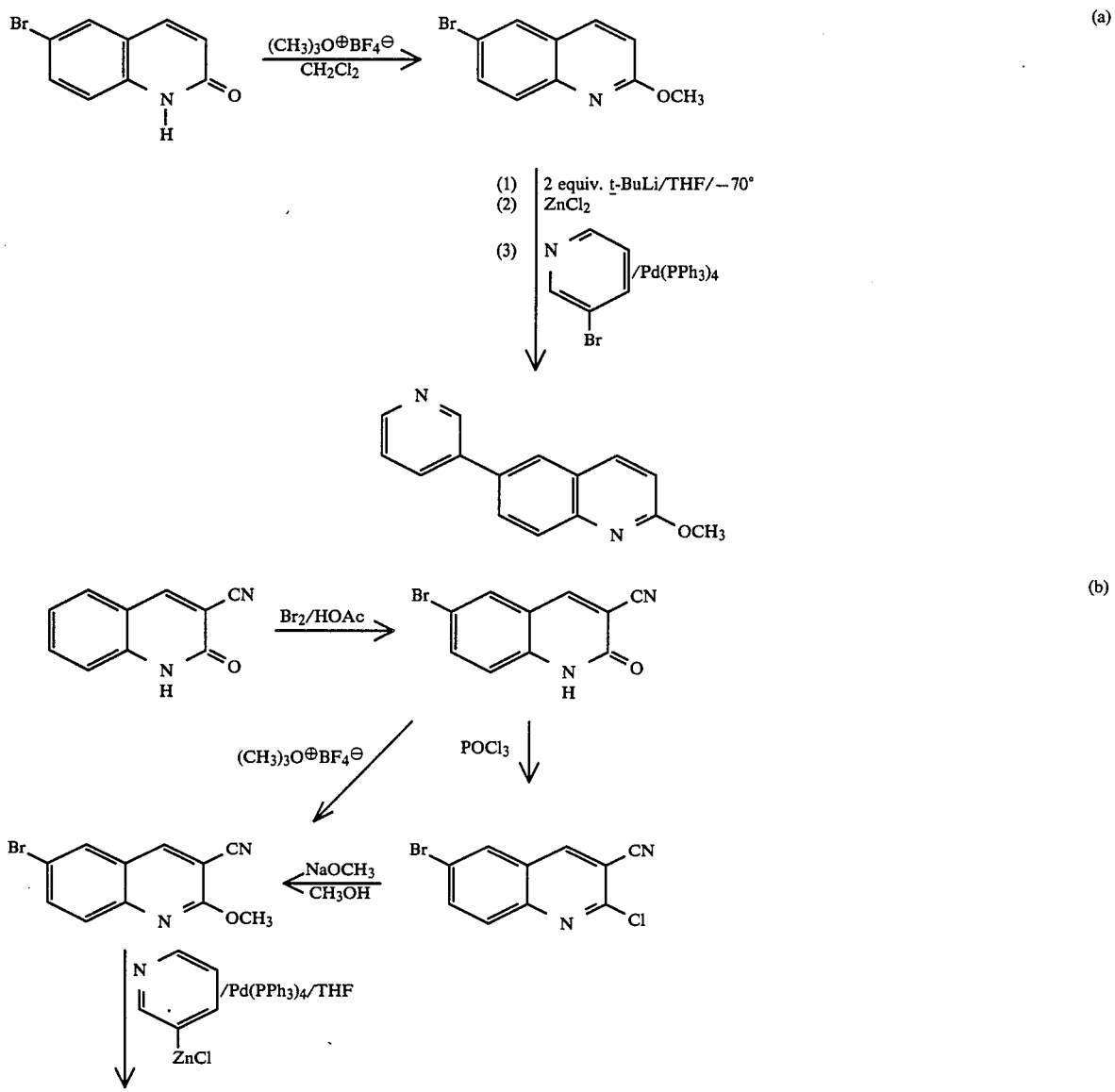

-continued
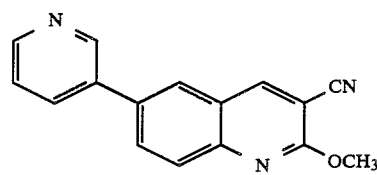
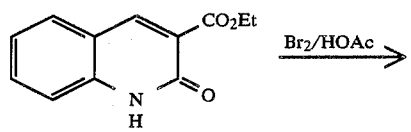 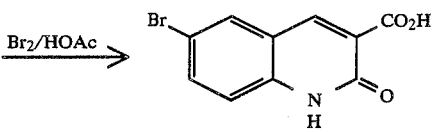 (c)
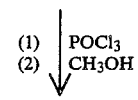
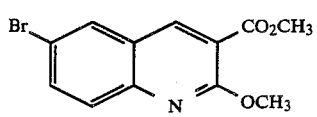 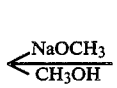 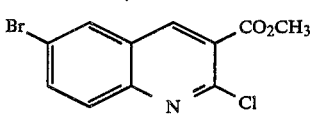
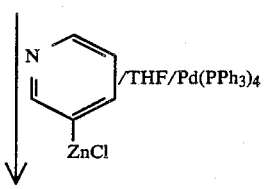
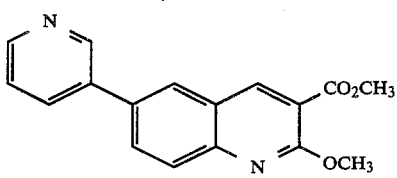
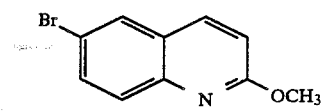 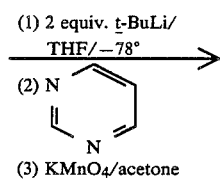 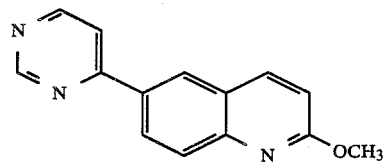 (d)
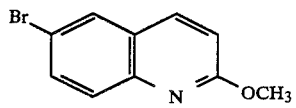 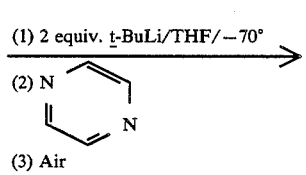 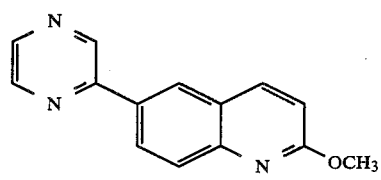 (e)
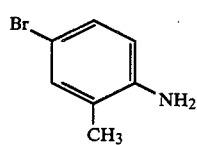 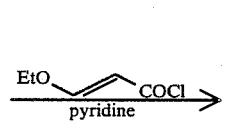 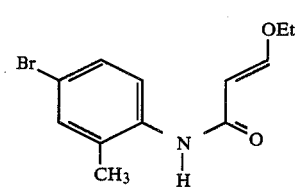 (f)

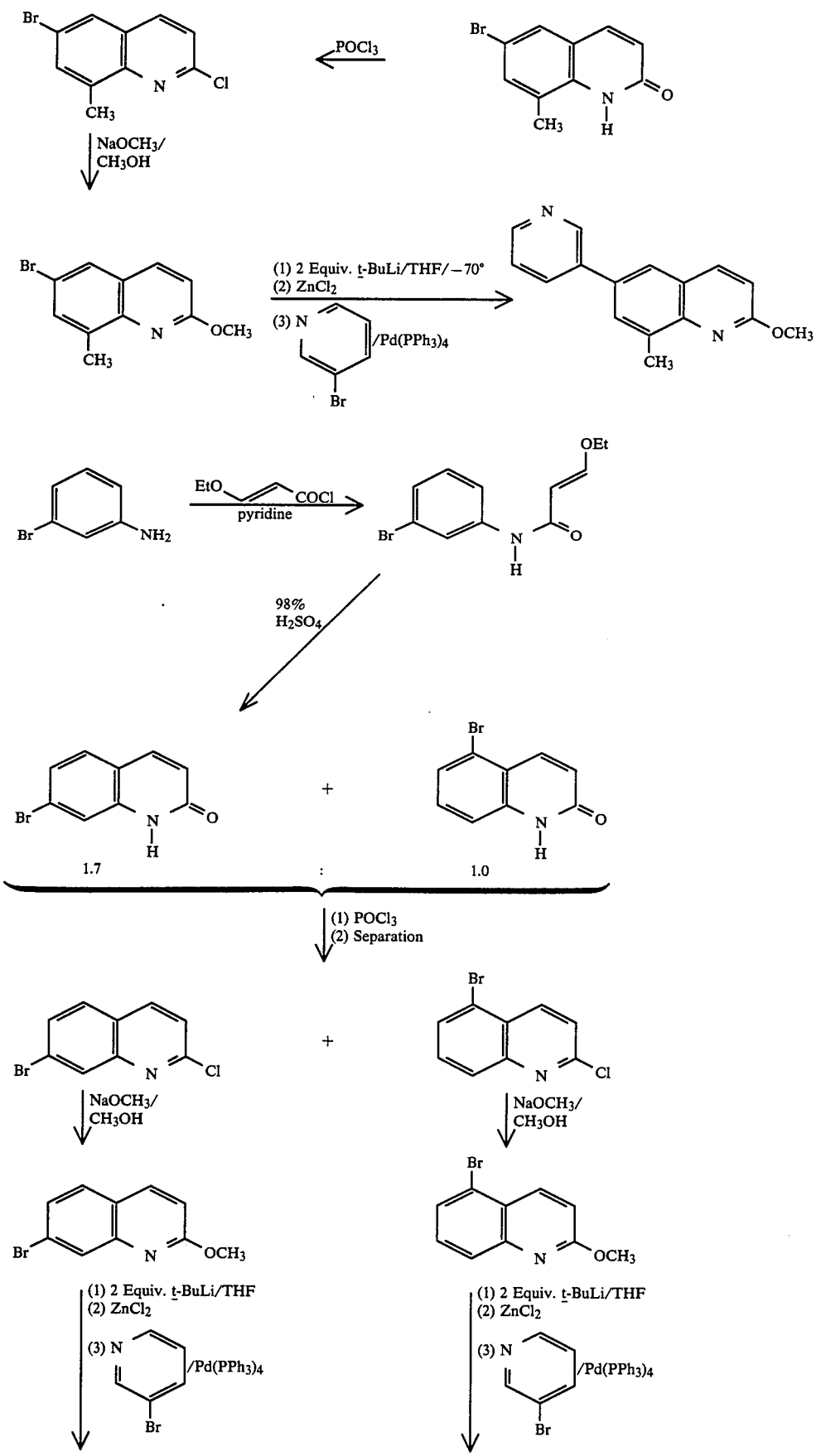
(g)

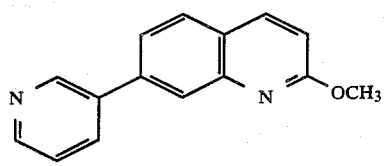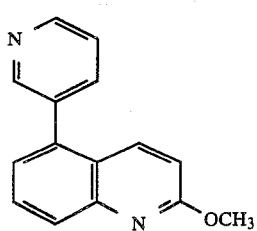
(h)
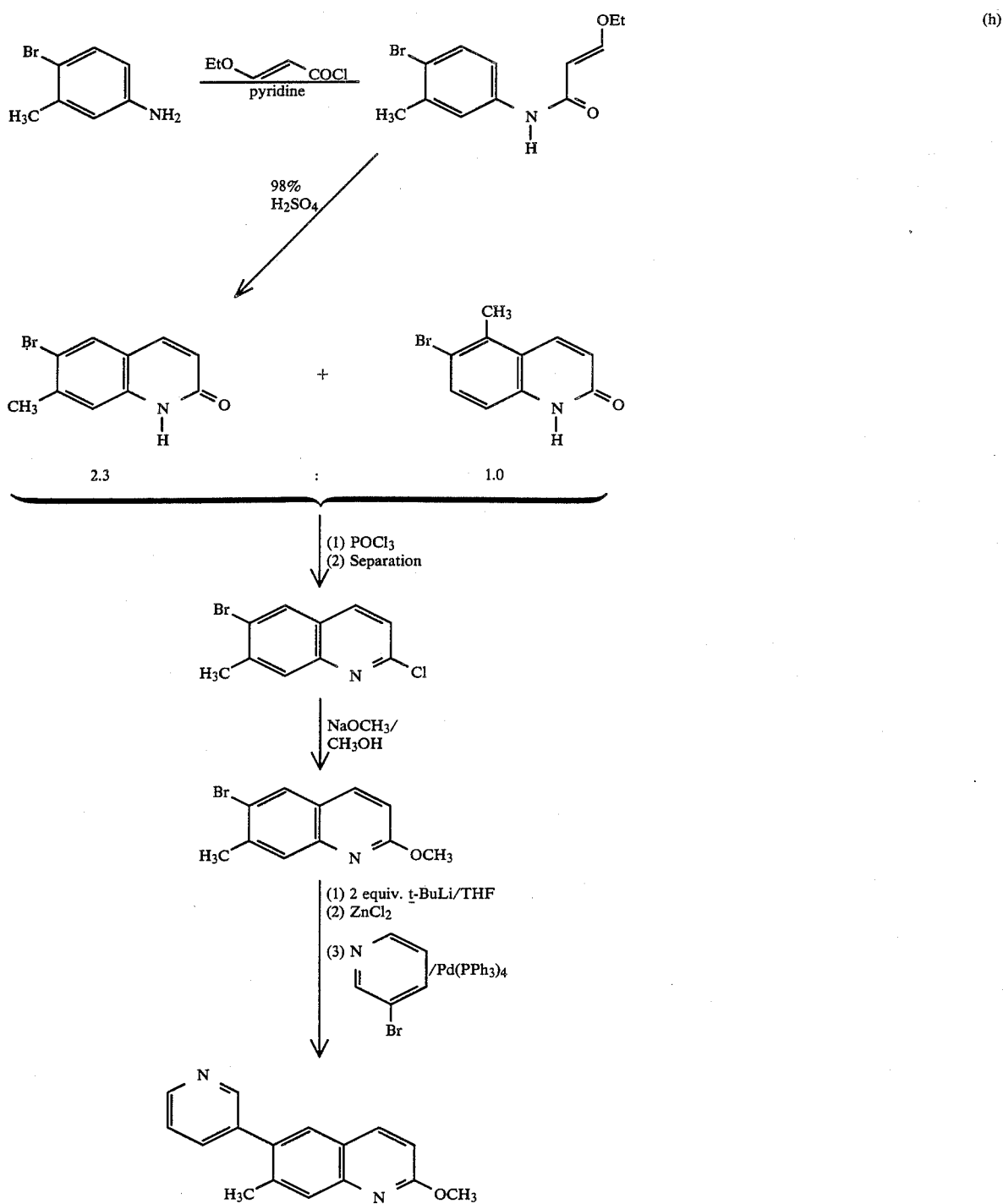

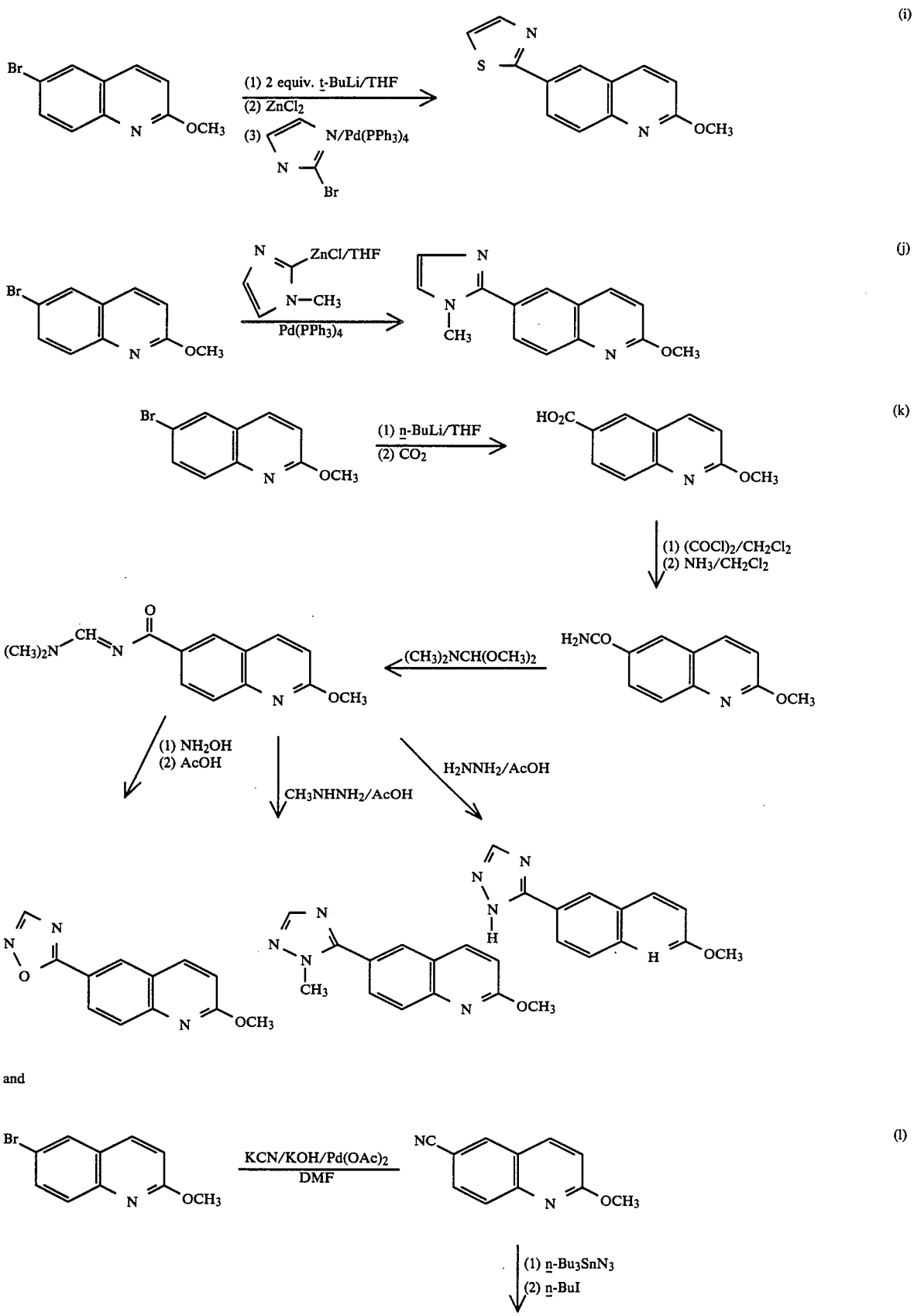

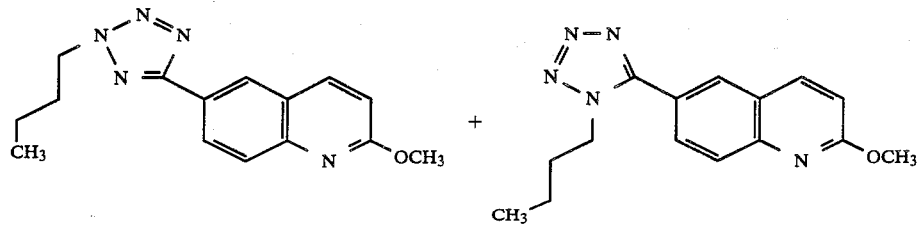

Route B:
This route can be illustrated in general terms as follows:

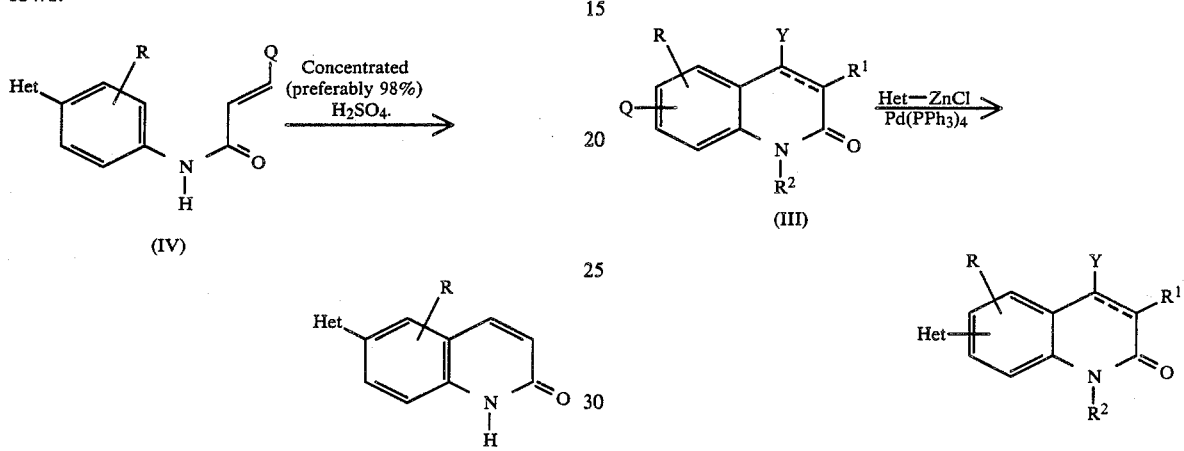

Q is a leaving group such as $C_1$–$C_4$ alkoxy. Q is preferably methoxy or ethoxy.

Thus it will be seen that this reaction involves the cyclisation of a propenamide derivative, typically a 3-ethoxypropenamide, using concentrated (typically 98%) sulphuric acid. The reaction is typically carried out by stirring the reactants at room temperature for 8–48 hours. The product can then be isolated and purified conventionally.

A typical reaction is illustrated as follows:

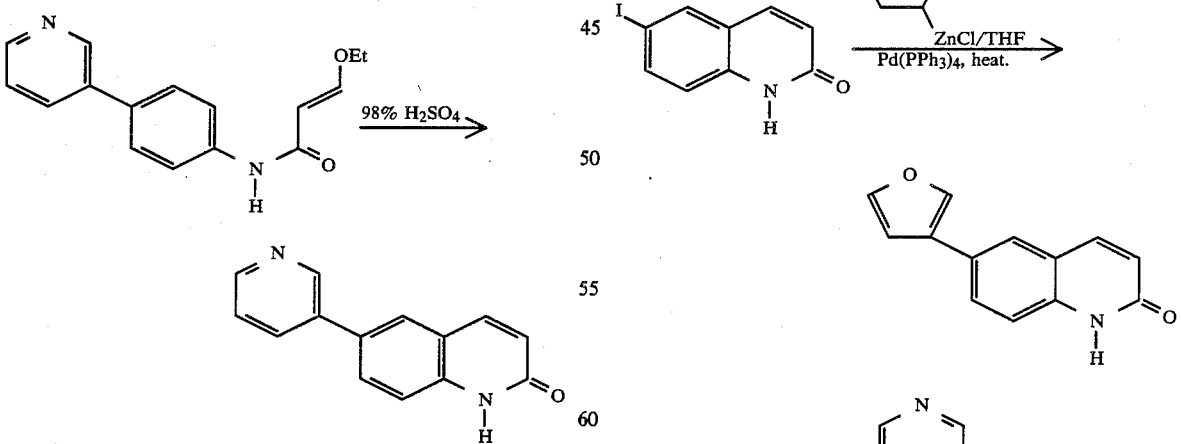

The starting materials are either known compounds or can be obtained conventionally.

Route C:
This route can be illustrated in general terms as follows:

Q is a suitable leaving group, e.g. Cl, Br, or I. Thus it will be seen that this reaction involves the displacement of a leaving group by the heteroaryl zinc chloride with tetrakis (triphenylphosphine) palladium(O) catalysis. The reaction is typically carried out by heating the reactants at up to reflux temperature in a suitable organic solvent, e.g. THF.

Typical reactions are illustrated as follows:

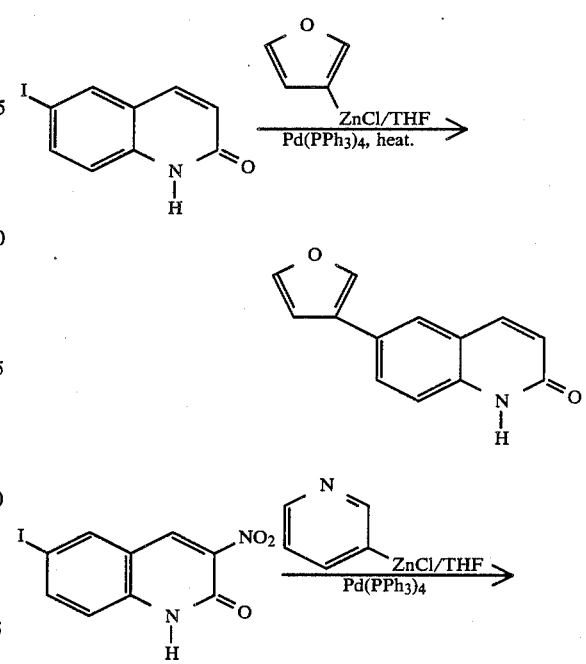

-continued

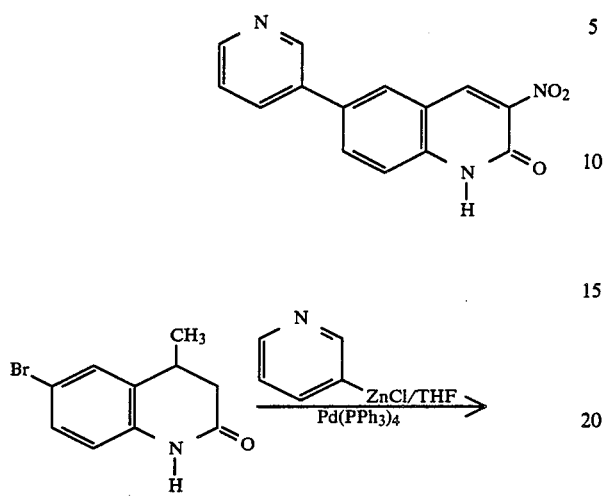

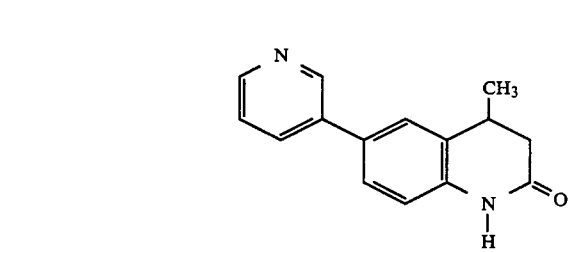

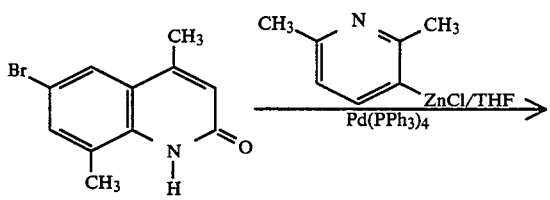

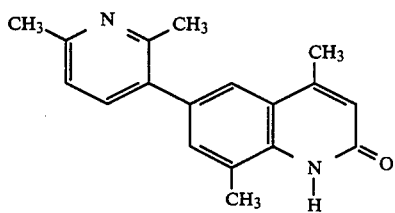

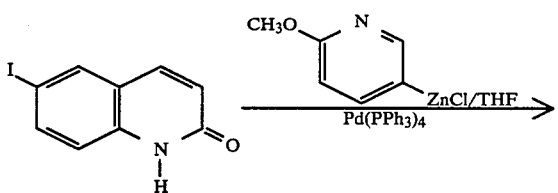

-continued

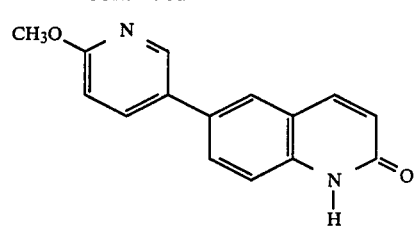

and

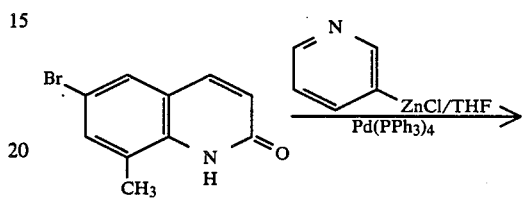

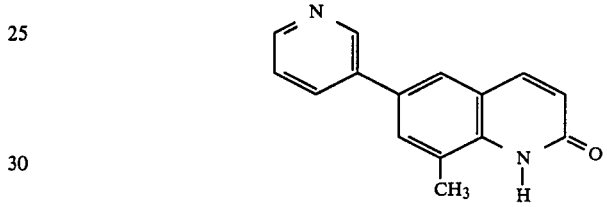

Heteroaryl magnesium chlorides may also be used in place of zinc chlorides using other suitable transition metal catalysts (e.g. nickel-based).

The starting materials are either known compounds or are obtainable conventionally. The heteroarylzinc chlorides are most conveniently obtained in situ by reacting the appropriate haloheterocycle at $-70°$ to $-100°$ C. in THF with 2 equivalents of t-butyl lithium to obtain the lithio-derivative, followed by reaction with a solution of anhydrous zinc chloride in THF. The heteroarylzinc chlorides can also be prepared from the corresponding Grignard reagents by reacting them with a solution of zinc chloride in THF. The desired end product is then typically obtained by allowing the reaction mixture to warm to room temperature, followed by adding the appropriate halo-quinolone and the tetrakis (triphenylphosphine) palladium(O) in THF and then heating under reflux until the reaction is complete; typically in 1 to 48 hours. The product can then be recovered and purified conventionally.

The starting materials of this route can be prepared by conventional procedures. Typical routes to these materials, many of which are illustrated in detail in the following Preparations, are as follows:

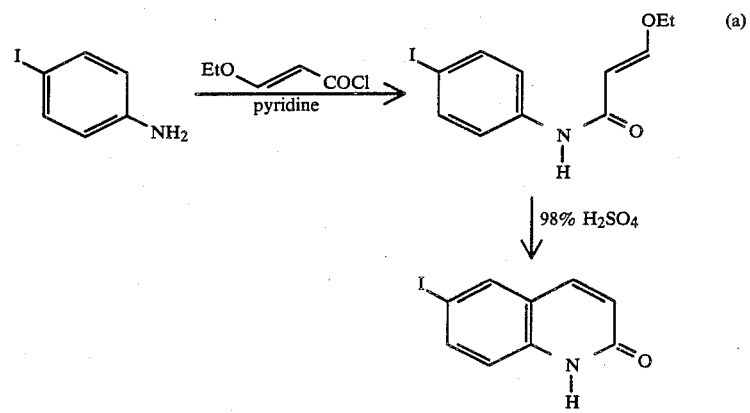
(a)
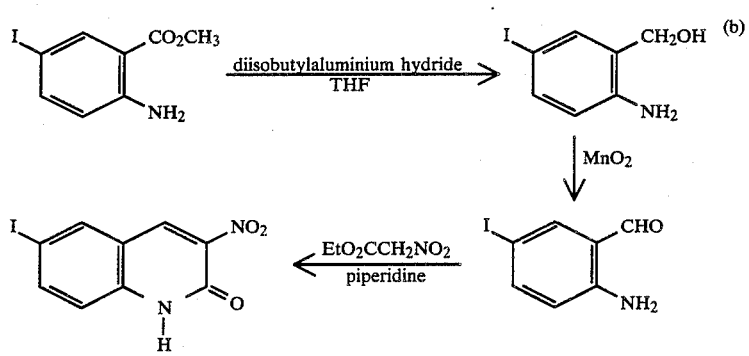
(b)
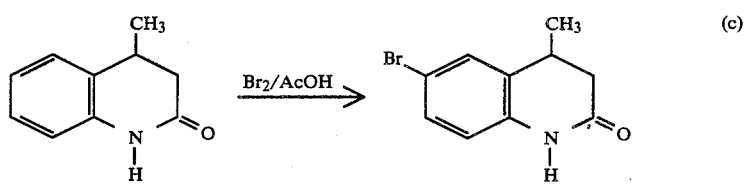
(c)
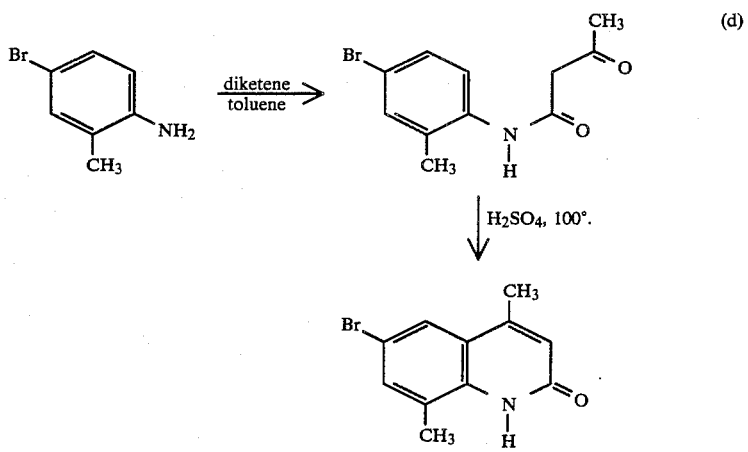
(d)
Route D:
This route can be illustrated in general terms as follows:
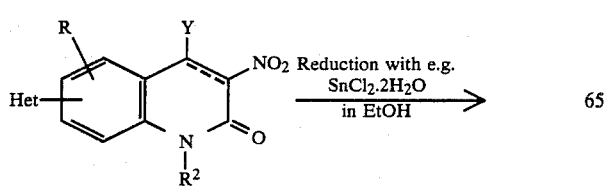
-continued
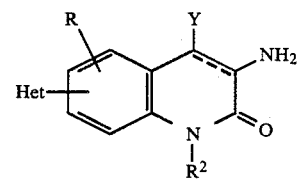

This reaction involves reduction of a nitro group, preferably using stannous chloride dihydrate in ethanol. The reaction is typically carried out by heating the reactants at up to reflux temperature for 1-8 hours.

A typical reaction is illustrated as follows:

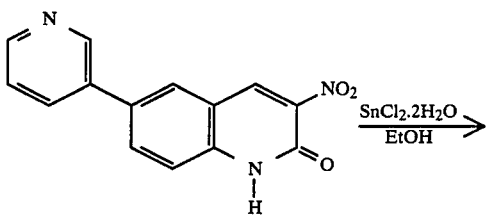

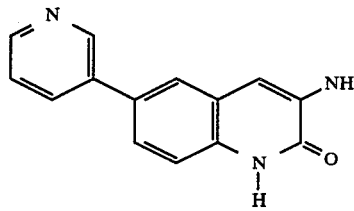

Route E:

The compounds of the formula (I) in which $R^1$ is Cl, Br or I can also be prepared by halogenation of the compounds in which $R^1$ is H using conventional procedures. A typical reaction is illustrated as follows:

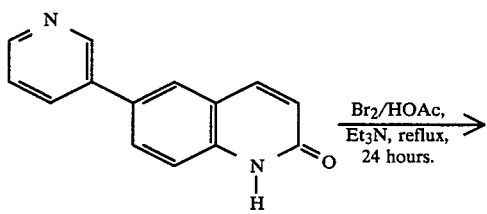

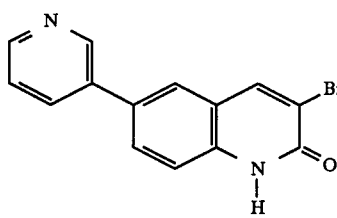

Route F:

The compounds of the formula (I) in which "Het" is an N-oxide can be prepared by the oxidation of the corresponding parent nitrogen-containing heterocycle, typically using a peracid oxidant such as m-chloroperbenzoic or peracetic acid under conventional reaction conditions. A typical reaction is illustrated as follows:

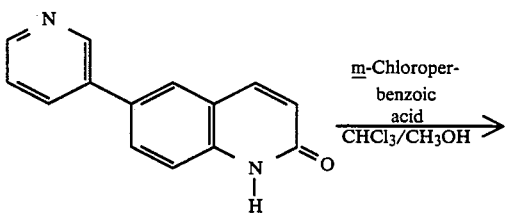

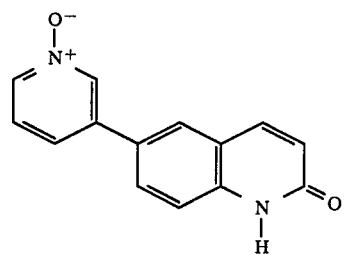

Route G:

The compounds of the formula (I) in which $R^2$ is $C_1$-$C_4$ alkyl or 2-hydroxyethyl can also be prepared by the N-alkylation of the corresponding compounds in which $R^2$ is H. This is typically achieved by reaction of the N-unsubstituted quinolone with sodium hydride or other strong base to form the anion, followed by reaction with, e.g., a $C_1$-$C_4$ alkyl halide, di($C_1$-$C_4$ alkyl)sulphate or 2-hydroxyethyl halide in conventional manner. A typical reaction is illustrated as follows:

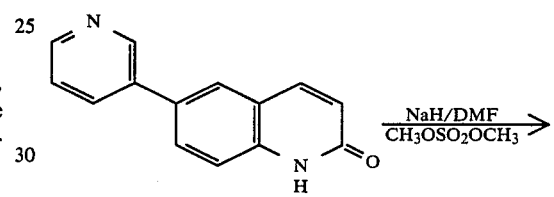

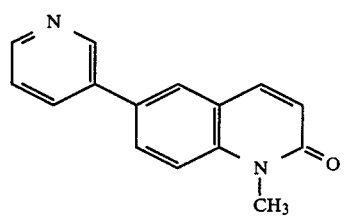

Route H:

This route can be illustrated in general terms as follows:

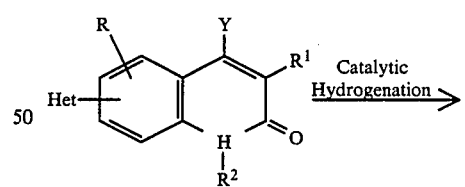

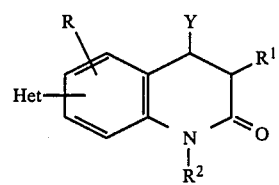

This reaction involves the catalytic hydrogenation of the 3,4-double bond over an appropriate catalyst, e.g. a transition metal catalyst. The reaction is typically carried out by heating the starting material in ethanol at 25°-100° C. and 15-5000 p.s.i. hydrogen pressure over 10% palladised charcoal, for 1-7 days.

A typical reaction is illustrated as follows:

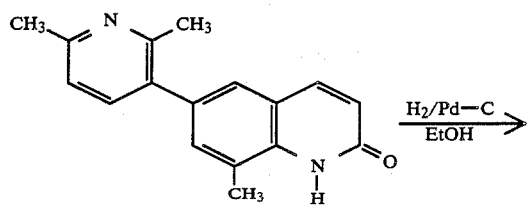

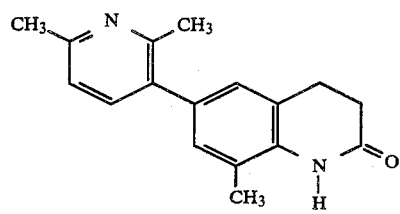

Route I:

This route can be illustrated in general terms as follows:

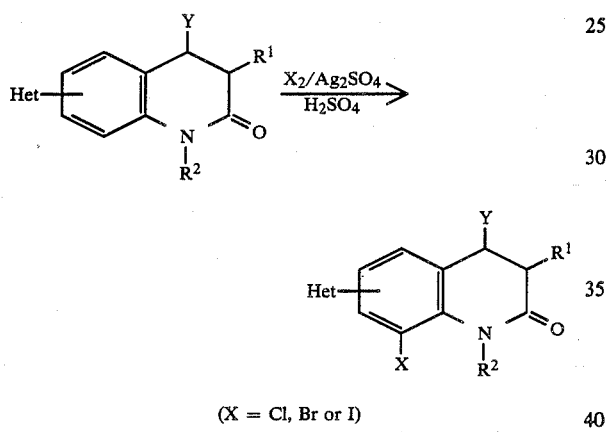

(X = Cl, Br or I)

This reaction involves the electrophilic halogenation of the 8-position of the 3,4-dihydroquinolone starting material in concentrated (preferably 98%) sulphuric acid in the presence of silver sulphate (X=Cl, Br, I). The reaction is typically conducted at 0°–70° for 1–16 hours. The product can then be purified conventionally.

A typical reaction is illustrated as follows:

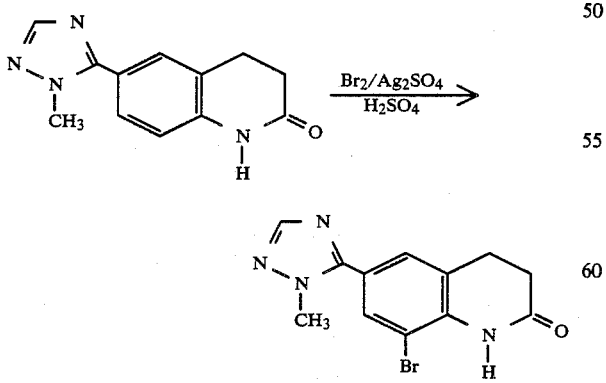

Route J:

This route can be illustrated in general terms as follows:

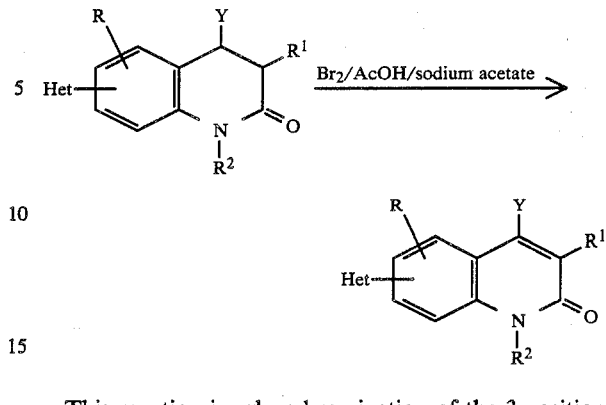

This reaction involves bromination of the 3-position of the starting material followed by dehydrobromination to generate the 3,4-double bond. The reaction is typically carried out by heating the 3,4-dihydroquinolone starting material with bromine and sodium acetate in acetic acid at 25°–120° for 1–2 hours.

The product can then be purified conventionally.

A typical reaction is illustrated as follows:

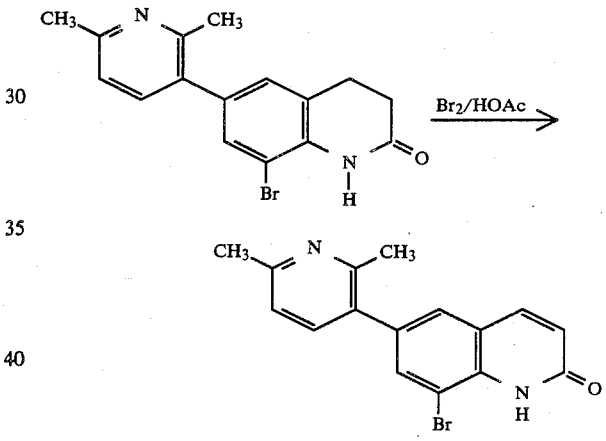

Route K:

This route can be illustrated in general terms as follows:

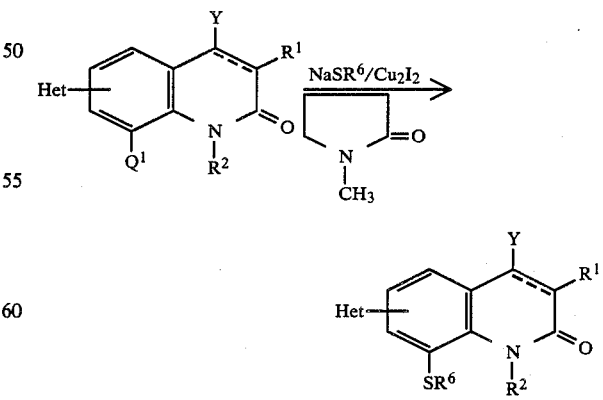

where $R^6$ is $C_1$–$C_4$ alkyl and $Q^1$ is a leaving group.

This reaction involves the nucleophilic substitution of a leaving group $Q^1$ (e.g. F, Cl, Br, I) by a metal salt (e.g. an alkali metal salt) of a $C_1$–$C_4$ alkylthiol in the presence of a copper (I) catalyst. It is typically conducted using the sodium salt in a high boiling organic solvent such as N-methylpyrrolidone at up to reflux temperature (e.g. at 160° C.) for 0.5–48 hours. The product can then be isolated and purified by conventional means.

A typical reaction is illustrated as follows:

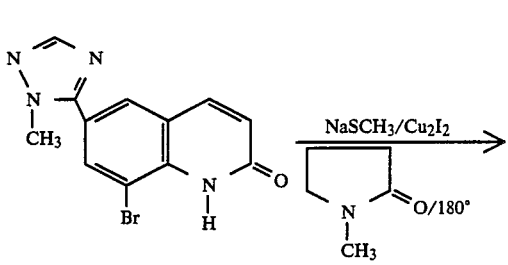

Route L:

This route can be illustrated in general terms as follows:

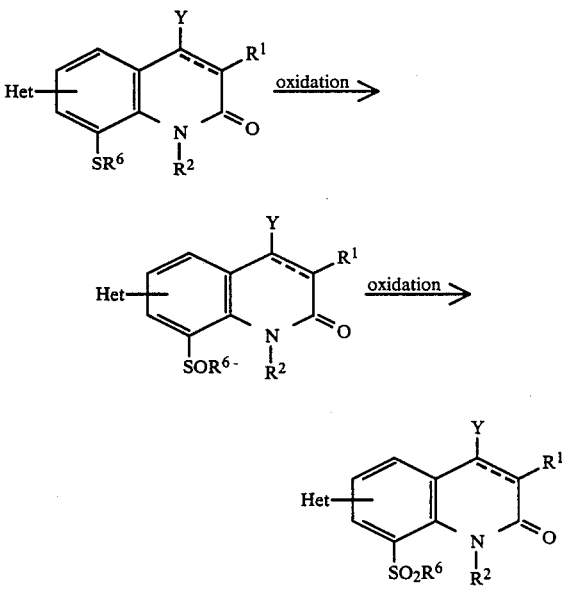

where $R^6$ is $C_1$–$C_4$ alkyl.

The reaction involves the oxidation of the sulphide moiety to the corresponding sulphoxide or sulphone with a suitable oxidising agent such as an organic peracid or sodium metaperiodate. It is typically conducted in an organic solvent such as dichloromethane or chloroform between −70° and +30° for 1–24 hours.

Typical reactions are illustrated as follows:

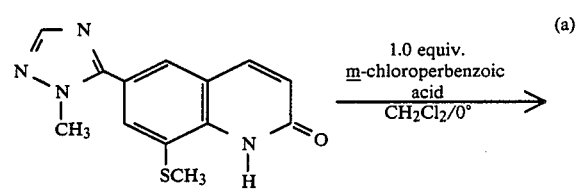

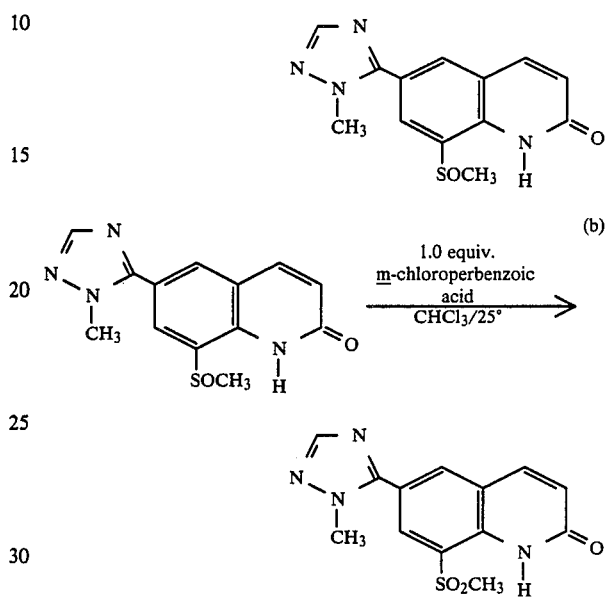

Route M:

This route can be illustrated in general terms as follows:

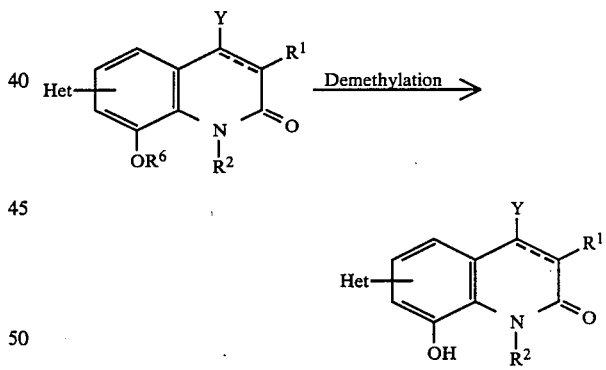

where $R^6$ is a $C_1$–$C_4$ alkyl group.

The demethylation is preferably carried out by heating the alkoxyquinoline in aqueous mineral acid, preferably 48% HBr, or by treatment with other demethylation reagents such as boron tribromide or pyridinium hydrochloride.

A typical reaction is illustrated as follows:

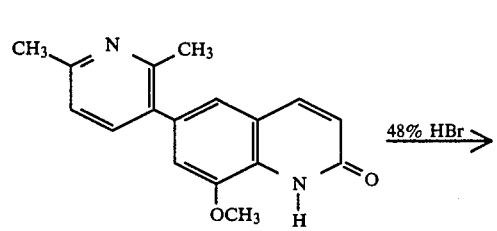

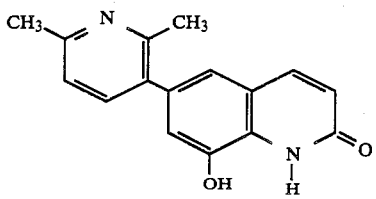

Route N:

This route can be illustrated in general terms as follows:

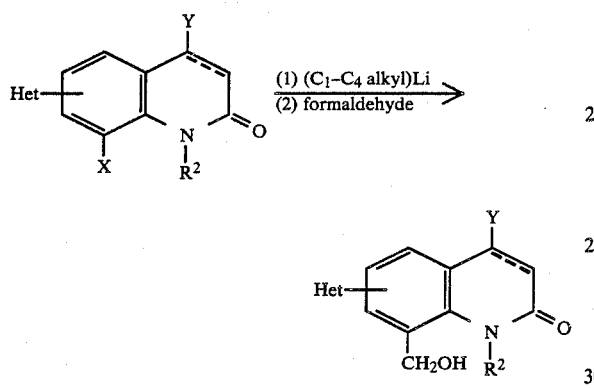

The reaction involves the exchange of a halogen atom "X" (X=Cl, Br, or I) with lithium derived from a $C_1$-$C_4$ alkyllithium followed by the subsequent quenching of the resulting organometallic species with gaseous formaldehyde (e.g. generated by sublimation of paraformaldehyde). The reaction is typically carried out at from $-75°$ and $0°$ C. in a suitable organic solvent (e.g. tetrahydrofuran). When $R^2$ is H, at least 2 equivalents of a $C_1$-$C_4$ alkyllithium should be used. The preferred alkyllithium is n-butyllithium.

A typical reaction is illustrated as follows:

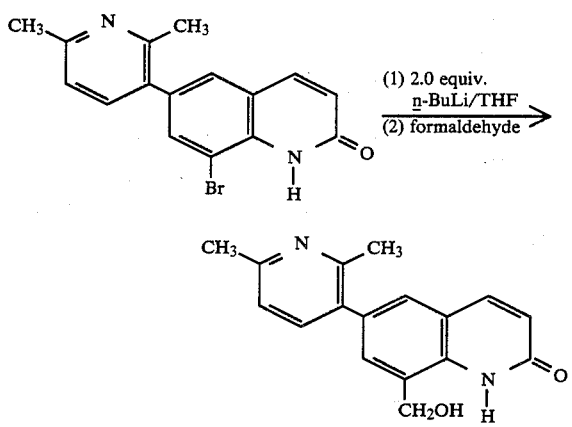

Salts of the compounds of the formula (I) are preparable by entirely conventional methods, e.g. by reacting a solution of the free base in an organic solvent with a solution of an appropriate acid in an organic solvent to form an acid addition salt, or by reacting the free base with an appropriate base, e.g. an alkali metal or alkaline earth metal hydroxide, preferably aqueous sodium hydroxide, to form a pharmaceutically acceptable metal salt.

Where the compounds of the invention contain one or more asymmetric centres, then the invention include the separated enantiomers and diastereoisomers or mixtures thereof. The separated forms can be obtained by conventional means.

The following Examples illustrate the preparation of the compounds (I). (All temperatures are in °C.):

EXAMPLE 1

Preparation of 6-(3-pyridyl)-2-(1H)-quinolone

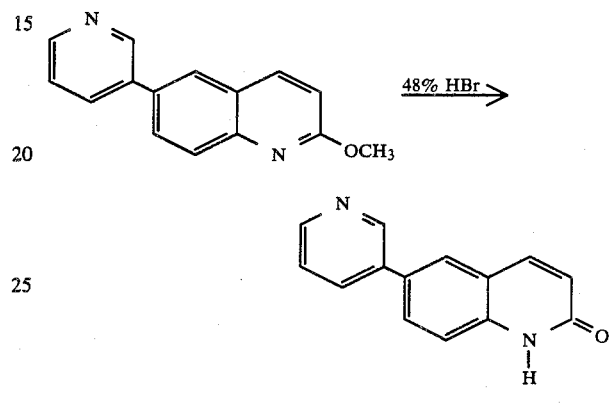

A stirred solution of 2-methoxy-6-(3-pyridyl) quinoline (1.83 g) in 48% aqueous hydrobromic acid (6 cm³) was heated at 100° C. for 1.5 hours. The mixture was then cooled in an ice bath, adjusted with 5M sodium hydroxide solution to pH 8, and continuously extracted with chloroform for 6 hours. The dried ($MgSO_4$) organic extract was then evaporated to give a solid which was recrystallised from methanol-ethyl acetate to afford 6-(3-pyridyl)-2-[1H]-quinolone, m.p. 217°–218°, (0.62 g).

Analysis %: Found: C, 75.9; H, 4.8; N, 12.2. Calculated for $C_{14}H_{12}N_2O$: C, 75.7; H, 4.5; N, 12.6.

EXAMPLES 2–11

The following compounds were prepared similarly to Example 1 starting from the appropriate 6-substituted-2-methoxyquinoline and 48% aqueous HBr:

| Example No. | Het | Form isolated and m.p. (°C.) | Analysis % (Theoretical in brackets) | | |
|---|---|---|---|---|---|
| | | | C | H | N |
| 2 | [pyridyl] | Free base, 258–260° | 74.8 (75.7 | 4.5 4.5 | 12.2 12.6) |
| 3 | [pyridyl] | 0.1 H₂O, 295–297° | 75.1 (75.1 | 4.6 4.6 | 12.3 12.5) |

-continued

![structure: Het-quinolin-2(1H)-one]

| Example No. | Het | Form isolated and m.p. (°C.) | Analysis % (Theoretical in brackets) C | H | N |
|---|---|---|---|---|---|
| 4 | 3-methyl-4-pyridyl | 0.75 H₂O, 225–235° (decomp.) | 72.0 (72.1 | 5.0 5.4 | 10.9 11.2) |
| 5 | 3-methyl-4-pyridyl (isomer) | Free base, 268–272° | 74.8 (74.8 | 5.2 5.2 | 11.3 11.6) |
| 6 | 2-pyrimidinyl | 0.25 H₂O, >310° | 68.5 (68.6 | 4.0 4.2 | 18.4 18.4) |
| 7 | pyridazinyl | 0.25 H₂O, 287–289° | 68.6 (68.6 | 4.1 4.2 | 18.5 18.4) |
| 8 | pyridazinyl | monohydrate, >310° | 65.2 (64.7 | 4.6 4.6 | 16.9 17.4) |
| 9 | pyrimidinyl | Free base, >310° | 69.8 (69.9 | 4.0 4.1 | 18.4 18.8) |
| 10 | pyrimidinyl | Free base, 289–291° | 69.7 (69.9 | 4.1 4.1 | 18.5 18.8) |
| 11 | pyrazinyl | 0.25 H₂O, 287–289° | 68.8 (68.6 | 4.1 4.2 | 18.1 18.4) |

EXAMPLES 12 AND 13

The following compounds were prepared similarly to Example 1 starting from the appropriate 3,6-disubstituted-2-methoxyquinoline but using aqueous 5M hydrochloric acid instead of 48% hydrobromic acid.

![structure: 6-Het-3-R¹-quinolin-2(1H)-one]

| Example No. | Het | R¹ | Form isolated and m.p. (°C.) | Analysis % (Theoretical in brackets) C | H | N |
|---|---|---|---|---|---|---|
| 12 | 3-pyridyl | —CN | 0.2 H₂O, >355° (decomp.) | 72.2 (71.8 | 4.0 3.8 | 16.4 16.8) |
| 13 | 4-pyridyl | —CN | 0.25 H₂O, 322–325° | 71.8 (71.6 | 4.1 3.8 | 15.9 16.7) |

EXAMPLE 14

3-Methoxycarbonyl-6-(3-pyridyl)-2-[1H]-quinolone hemihydrate

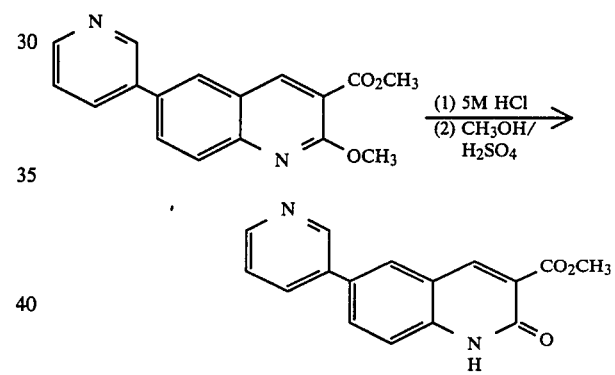

A solution of 2-methoxy-3-methoxycarbonyl-6-(3-pyridyl)quinoline (0.50 g) in 5M hydrochloric acid (30 cm³) was heated under reflux for 20 minutes. The cooled mixture was filtered and the solid washed with methanol to give the crude intermediate 6-(3-pyridyl)-2-[1H]-quinolone-3-carboxylic acid hydrochloride salt, m.p. 350°–352°, (0.45 g). This material was taken into methanol (50 cm³) and heated under reflux with concentrated sulphuric acid (1 cm³) for 1 hour. The mixture was concentrated in vacuo and the residue partitioned between chloroform (100 cm³) and aqueous sodium bicarbonate solution. The aqueous phase was further extracted with chloroform (3×25 cm³), and the combined organic extracts were dried (MgSO₄) and evaporated to afford 3-methoxycarbonyl-6-(3-pyridyl)-2-[1H]-quinolone hemihydrate, m.p. 223°–225°, (0.32 g).

Analysis %: Found: C, 66.9; H, 4.3; N, 9.4 Calculated for $C_{16}H_{12}N_2O_3 \cdot 0.5H_2O$: C, 66.5; H, 4.5; N, 9.7.

EXAMPLE 15

3-Methoxycarbonyl-6-(4-pyridyl)-2-[1H]-quinolone hemihydrate, m.p. 246°–248°, was prepared similarly to the previous Example using 2-methoxy-3-methoxycarbonyl-6-(4-pyridyl)quinoline as the starting material.

Analysis %: Found: C, 66.7; H, 4.2; N, 9.4 Calculated for $C_{16}H_{12}N_2O_3 \cdot \frac{1}{2}H_2O$: C, 66.4; H, 4.5; N, 9.7.

EXAMPLE 16

Preparation of 8-methyl-6-(3-pyridyl)-2-(1H)-quinolone

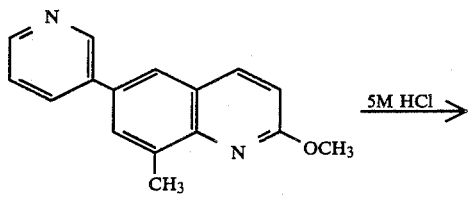

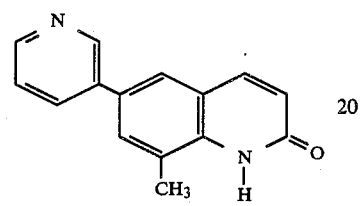

A stirred solution of 2-methoxy-8-methyl-6-(3-pyridyl)quinoline (1.07 g) in 5M hydrochloric acid (10 cm$^3$) was heated under reflux for 2.5 hours and then cooled. The cooled solution was basified to pH 9 with 2M aqueous sodium hydroxide, extracted with chloroform:methanol 9:1 (4×100 cm$^3$), and the combined and dried (MgSO$_4$) extracts were concentrated in vacuo to afford a solid. Recrystallisation of the solid from ethyl acetate-methanol gave 8-methyl-6-(3-pyridyl)-2-(1H)-quinolone, m.p. 235.5°–236.5°, (0.63 g).

Analysis %: Found: C, 76.0; H, 5.1; N, 11.6. Calculated for $C_{15}H_{12}N_2O$: C, 76.2; H, 5.1; N, 11.9.

EXAMPLES 17–56

The following compounds were prepared similarly to the method of Example 16 using the appropriately substituted 2-methoxyquinoline and either 10% by volume of 48% aqueous HBr in ethanol (Examples 37, 42, 46 and 51), or 5M aqueous HCl (remaining Examples).

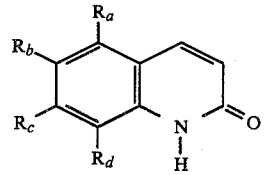

In Example 43, the starting material was 2-methoxy-6-(1-tributylstannyltetrazol-5-yl)quinoline, the tributylstannyl group being removed under the acidic reaction conditions.

In Example 37, some hydrolysis of —CN to —CONH$_2$ occurred. The resulting mixture of products was separated by chromatography on silica gel (Merck "MK 60.9385"), eluting with chloroform:methanol:aqueous ammonia (S.G. 0.880), 94:5:1 by volume. The carbamoyl-compound is designated as Example 51.

| Example No. | $R_a$ | $R_b$ | $R_c$ | $R_d$ | Form isolated and m.p. (°C.) | Analysis % (Theoretical in Brackets) | | |
|---|---|---|---|---|---|---|---|---|
| | | | | | | C | H | N |
| 17 | —H | 4-pyridyl | —H | —CH$_3$ | Monohydrochloride, >350° | 66.1 (66.1 | 4.7 4.8 | 10.2 10.3) |
| 18 | —H | 2,6-dimethyl-3-pyridyl | —H | —H | Free base hemihydrate, 280–283° | 74.5 (74.1 | 5.7 5.8 | 10.9 10.8) |
| 19 | —H | 2-methyl-5-pyridyl | —H | —H | Free base hemihydrate, 282–284° | 73.2 (73.4 | 5.0 5.3 | 11.5 11.4) |
| 20 | —H | 2-methyl-3-pyridyl | —H | —H | Free base 293–295.5° | 76.4 (76.3 | 5.1 5.1 | 11.9 11.9) |
| 21 | —H | thiazol-2-yl | —H | —H | Free base, monohydrate, 279–280° | 58.5 (58.5 | 3.1 4.1 | 11.4 11.4) |
| 22 | —H | 2-amino-5-pyridyl | —H | —H | Monohydrochloride 0.5 H$_2$O, >300° | 59.4 (59.5 | 4.3 4.6 | 14.7 14.9) |

-continued

| Example No. | $R_a$ | $R_b$ | $R_c$ | $R_d$ | Form isolated and m.p. (°C.) | Analysis % (Theoretical in Brackets) | | |
|---|---|---|---|---|---|---|---|---|
| | | | | | | C | H | N |
| 23 | —H | 2-pyrimidinyl | —H | —CH$_3$ | Monohydrochloride, 290–292° | 61.4 (61.4 | 4.4 4.4 | 15.3 15.3) |
| 24 | —H | 2,6-dimethyl-4-pyridinyl | —H | —CH$_3$ | Free base, 256–259° | 77.2 (77.2 | 6.0 6.1 | 10.3 10.6) |
| 25 | —H | —H | 2-pyridinyl | —H | Free base, 235–237° | 75.1 (75.6 | 4.7 4.5 | 12.5 12.6) |
| 26 | —H | —H | 3-pyridinyl | —H | Free base, 0.25 H$_2$O, 237–239° | 74.0 (74.2 | 4.5 4.7 | 12.1 12.4) |
| 27 | —H | —H | 4-pyridinyl | —H | Free base, 261–263° | 75.4 (75.6 | 4.5 4.5 | 12.5 12.6) |
| 28 | 2-pyridinyl | —H | —H | —H | Free base, 254–256° | 75.5 (75.6 | 4.5 4.5 | 12.5 12.6) |
| 29 | 3-pyridinyl | —H | —H | —H | Free base, 259–261° | 75.3 (75.6 | 4.5 4.5 | 12.3 12.6) |
| 30 | —H | 2-pyridinyl | —CH$_3$ | —H | Free base, 241–243° | 76.1 (76.2 | 5.2 5.1 | 11.9 11.9) |
| 31 | —H | 3-pyridinyl | —CH$_3$ | —H | Free base, 249–251° | 76.4 (76.2 | 5.3 5.1 | 12.1 11.9) |
| 32 | —H | 4-pyridinyl | —CH$_3$ | —H | Free base, 297–299° | 75.8 (76.2 | 5.2 5.1 | 11.6 11.9) |
| 33 | —H | 2-methyl-3-pyridinyl | —CH$_3$ | —H | Free base, 0.15 H$_2$O 284–294° | 76.0 (76.0 | 5.7 5.7 | 10.7 11.1) |
| 34 | —H | 2-thienyl | —H | —H | Free base, 260–263° | 68.4 (68.7 | 4.1 4.0 | 6.2 6.2) |

-continued

| Example No. | $R_a$ | $R_b$ | $R_c$ | $R_d$ | Form isolated and m.p. (°C.) | Analysis % (Theoretical in Brackets) | | |
|---|---|---|---|---|---|---|---|---|
| | | | | | | C | H | N |
| 35 | —H | 2,6-dimethylpyridin-3-yl | —H | —CH$_3$ | Free base, 242–244° | 76.7 (76.8 | 5.7 5.6 | 11.3 11.2) |
| 36 | —H | 2,3-dimethylpyridin-4-yl | —H | —CH$_3$ | Free base, 252–254° | 76.7 (76.8 | 5.7 5.6 | 11.1 11.2) |
| 37 | —H | 5-cyano-3-methylpyridin-... | —H | —CH$_3$ | Crude base, Solid | — | | |
| 38 | —H | 5-methyl-1H-1,2,4-triazol-3-yl | —H | —H | Monohydrochloride, 357–359° (decomp.) | 53.3 (53.1 | 3.6 3.6 | 22.3 22.5 |
| 39 | —H | 5-methyl-1H-1,2,4-triazol-3-yl | —H | —CH$_3$ | Free base, 0.25 H$_2$O, 290–292° | 62.5 (62.5 | 4.3 4.6 | 24.1 24.3) |
| 40 | —H | 1,5-dimethyl-1,2,4-triazol-3-yl | —H | —H | Free base, 0.25 H$_2$O, (decomp.) | 62.5 (62.5 | 4.4 4.6 | 24.2 24.3) |
| 41 | —H | 1,5-dimethyl-1,2,4-triazol-3-yl | —H | —CH$_3$ | Free base, 295–297° | 64.9 (65.0 | 5.1 5.0 | 23.3 23.3) |
| 42 | —H | 5-methyl-1,3,4-oxadiazol-2-yl | —H | —H | Free base, 228–230° (decomp.) | 61.6 (62.0 | 3.3 3.3 | 19.7 19.7) |
| 43 | —H | 5-methyl-1H-tetrazol-... | —H | —H | Free base, 297–299° (decomp.) | 56.1 (56.3 | 3.3 3.3 | 32.3 32.9) |
| 44 | —H | 1-n-butyl-5-methyltetrazol-... | —H | —H | Free base, 212–214° | 62.0 (62.4 | 5.6 5.6 | 26.2 26.0) |
| 45 | —H | 2-n-butyl-5-methyltetrazol-... | —H | —H | Free base, 198–201° | 62.4 (62.4 | 5.6 5.6 | 25.7 26.0) |

-continued

| Example No. | $R_a$ | $R_b$ | $R_c$ | $R_d$ | Form isolated and m.p. (°C.) | Analysis % (Theoretical in Brackets) C | H | N |
|---|---|---|---|---|---|---|---|---|
| 46 | — | 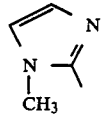 | —H | —H | Monohydrobromide, 323.5–325.5° | 50.8 (51.0 | 3.9 3.9 | 13.6 13.7) |
| 47 | —H | 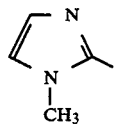 | —H | —CH₃ | Free base 0.25 H₂O, 221–224°. | 66.5 (69.0 | 5.4 5.6 | 16.9 17.2) |
| 48 | —H | 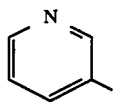 | —H | —H | Free base, 217–218° | 75.9 (75.7 | 4.8 4.5 | 12.2 12.6) |
| 49 | —H | 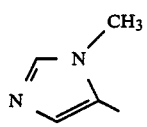 | —H | —CH₃ | Free base, 0.25 H₂O, 266–268° | 69.1 (69.0 | 5.2 5.6 | 17.1 17.2) |
| 50 | —H | 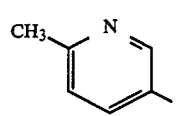 | —H | —CH₃ | Free base, 294.5–296° | 76.5 (76.8 | 5.7 5.6 | 10.7 11.2) |
| 51 | —H | 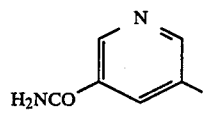 | —H | —CH₃ | Crude base, Solid | not characterised | | |
| 52 | —H | 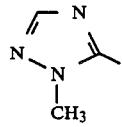 | —H | —Et | Free base, 237–241° | 66.3 (66.1 | 5.5 5.6 | 22.2 22.0) |
| 53 | —H | 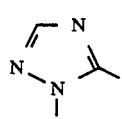 | —H | —CH(CH₃)₂ | Free base, 191–194° | 66.9 (67.1 | 6.1 6.1 | 20.8 20.9) |
| 54 | —H | 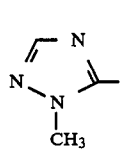 | —H | —OCH₃ | Free base, 211.5–215°. | 60.8 (60.9 | 4.8 4.7 | 21.9 21.9) |
| 55 | —H | 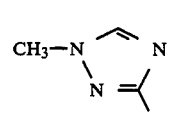 | —H | —CH₃ | Free base 0.25 H₂O, 270–272° | 64.3 (64.5 | 5.1 5.1 | 23.2 23.2) |
| 56 | —H | 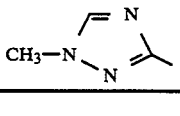 | —H | —Et | Free base, 252–254° | 66.1 (66.1 | 5.6 5.6 | 22.1 22.0) |

EXAMPLE 57

6-[1-Methyl-1,2,4-triazol-5-yl]-4,8-dimethyl-2-(1H)-quinolone 0.75H₂O, m.p. 327°, was prepared similarly to Example 16 using 6-[1-methyl-1,2,4-triazol-5yl]-2-methoxy-4,8-dimethylquinoline and 5M HCl as the starting materials.

Analysis %: Found: C, 62.8; H, 5.3; N, 20.6; Calculated for C₁₄H₁₄N₄O.0.75H₂O: C, 62.8; H, 5.8; N, 20.9.

EXAMPLE 58

Preparation of 8-methyl-6-[2,6-dimethylpyrid-3-yl]-2-(1H)-quinolone. 3H₂O, sodium salt

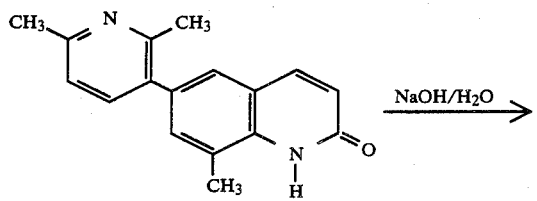

8-Methyl-6-[2,6-dimethylpyrid-3-yl]-2-(1H)-quinolone (94.7 g) was slurried with 5M aqueous sodium hydroxide solution (379 cm³) for 4 hours. The solid material was then filtered off and washed with water (380 cm³). Isopropanol (600 cm³) was added and the volatile material was distilled off to afford a solid which was dissolved in boiling methanol (1620 cm³). The hot solution was filtered, concentrated in vacuo (270 cm³ volume), and cooled to 0°. The precipitate was filtered and dried in vacuo at 50° to give the title compound, m.p. >220° (decomp.), (60.4 g).

Analysis %: Found: C, 59.8; H, 5.5; N, 7.9; Calculated for C₁₇H₁₅N₂ONa.3H₂O: C, 60.0; H, 6.2; N, 8.2.

EXAMPLE 59

Preparation of 8-hydroxymethyl-6-[2,6-dimethylpyrid-3-yl]-2-(1H)-quinolone. 0.1H₂O

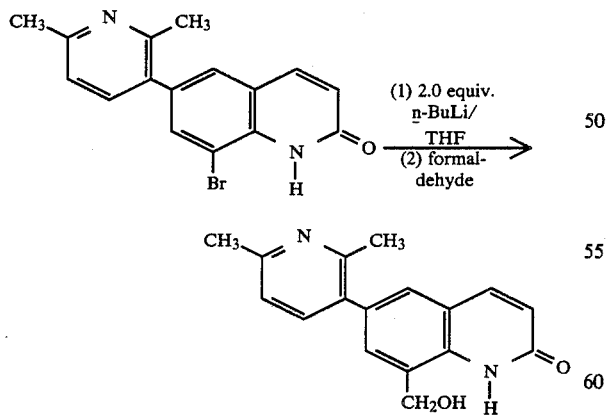

A solution of n-butyl lithium [1.04 cm³ of a 1.6M solution in n-hexane] was added at −70° to a stirred solution of 8-bromo-6-[2,6-dimethyl-pyrid-3-yl]-2-(1H)-quinolone (0.25 g) in THF (20 cm³) under nitrogen. After 2 hours, gaseous formaldehyde [generated by sublimation of paraformaldehyde (0.3 g)] was passed over the solution, and, after stirring for a further 10 minutes, the mixture was allowed to warm to room temperature. Saturated ammonium chloride solution (10 cm³) was then added and the mixture was extracted with chloroform (3×50 cm³). The combined and dried (MgSO₄) organic extracts were evaporated and the residue was chromatographed on silica (Merck "MK 60.9385" [Trade Mark]) eluting with dichloromethane:-methanol, 19:1. Combination and evaporation of the appropriate fractions afforded 8-hydroxymethyl-6-[2,6-dimethylpyrid-3-yl]-2-(1H)-quinolone. 0.1H₂O, m.p. 218.5°–221° (0.094 g).

Analysis %: Found: C, 72.1; H, 5.8; N, 9.9; Calculated for C₁₇H₁₆N₂O₂.0.1H₂O: C, 72.4; H, 5.7; N, 9.9.

EXAMPLE 60

Preparation of 6-(3-pyridyl)-2-(1H)-quinolone

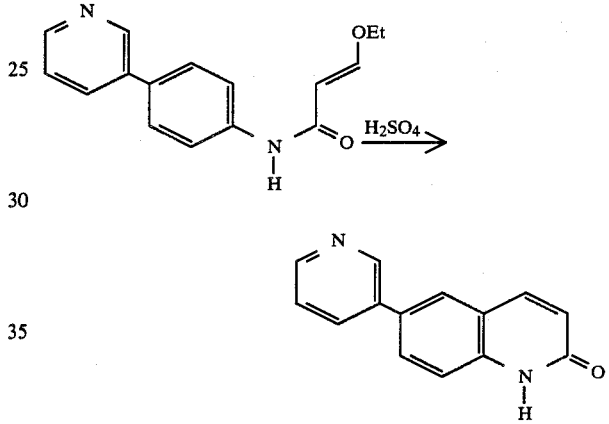

Trans-3-[4-(3-Ethoxypropenamido)phenyl]pyridine (1.43 g) was stirred in 98% sulphuric acid (4.0 cm³) for 16 hours. The mixture was added to ice (50 g) and the resulting solution was basified to pH8 with 2.5M sodium hydroxide solution. The mixture was extracted with chloroform:methanol, 9:1 (10×100 cm³), and the combined and dried (MgSO₄) extracts were concentrated in vacuo to yield a solid which was recrystallised from isopropanol to afford 6-(3-pyridyl)-2-(1H)-quinolone, m.p. 228°–230° (0.39 g).

Analysis %: Found: C, 75.3; H, 4.5; N, 12.5; Calculated for C₁₄H₁₂N₂O: C, 75.7; H, 4.5; N, 12.6.

EXAMPLE 61

Preparation of 6-(2-methoxypyrid-5-yl)-2-(1H)-quinolone

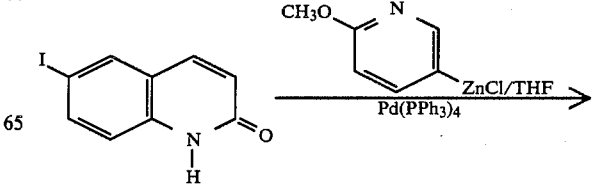

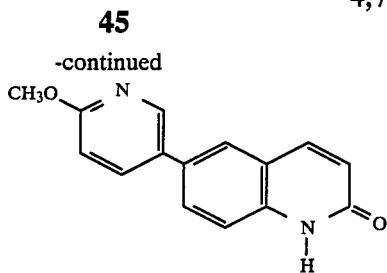

A solution of 5-bromo-2-methoxypyridine (1.50 g) in tetrahydrofuran (THF) (10 cm$^3$) was stirred at −70° under nitrogen during the addition of t-butyllithium (8.0 cm$^3$ of a 2.0M solution in pentane). After 10 minutes a solution of anhydrous zinc chloride (1.09 g) in tetrahydrofuran (THF) (10 cm$^3$) was added and the mixture was allowed to warm to room temperature over 1 hour. A suspension of 6-iodo-2-(1H)-quinolone (0.813 g) and tetrakis (triphenylphosphine) palladium(O) (0.03 g) in THF (10 cm$^3$) was then added and the mixture was heated under reflux for 3 hours. Saturated ammonium chloride solution (1 cm$^3$) was added to the cooled mixture followed by a solution of ethylenediaminetetraacetic acid disodium salt (6.0 g) in water (100 cm$^3$). Chloroform (100 cm$^3$) and methanol (30 cm$^3$) were added and the mixture was warmed until all the solid material dissolved. The phases were separated, the aqueous layer was further extracted with chloroform:methanol 9:1 (3×50 cm$^3$), and the combined and dried (MgSO$_4$) extracts were concentrated in vacuo to afford a solid which was recrystallised from isopropanol to give 6-(2-methoxypyrid-5-yl)-2-(1H)-quinolone, m.p. 248°–252°, (0.56 g).

Analysis %: Found: C, 71.4; H, 4.9; N, 11.2; Calculated for C$_{15}$H$_{12}$N$_2$O$_2$: C, 71.4; H, 4.8; N, 11.1.

EXAMPLES 62–72

The following compounds were prepared similarly to the previous Example starting from the appropriately substituted 6-iodo- or 6-bromo-2-(1H)-quinolone and the appropriate heteroarylzinc chloride with tetrakis (triphenylphosphine) palladium(O) as catalyst.

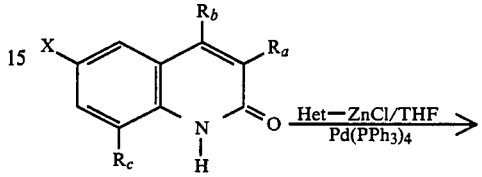

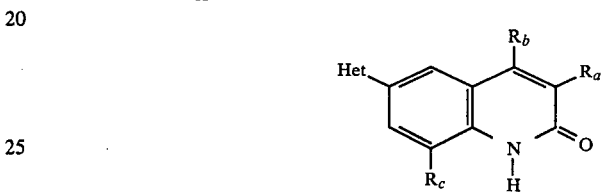

In Examples 69–72 the 2,6-dimethylpyrid-3-yl zinc chloride was generated from the appropriate magnesium Grignard reagent (which is a known compound) rather than from the appropriate lithio-derivative.

| Example No. | $R_a$ | $R_b$ | X | Het | $R_c$ | Form isolated and m.p. (°C.) | Analysis % (Theoretical in Brackets) | | |
|---|---|---|---|---|---|---|---|---|---|
| | | | | | | | C | H | N |
| 62 | —H | —H | —Br | (pyridine) | —CH$_3$ | Free base, 233–236° | 75.7 (76.2 | 5.1 5.1 | 11.8 11.9) |
| 63 | —H | —H | —Br | (pyridine) | —CH$_3$ | Free base, 235–237° | 76.0 (76.2 | 5.1 5.1 | 11.7 11.9) |
| 64 | —NO$_2$ | —H | —I | (pyridine) | —H | Free base, 0.5 H$_2$O, 338–340° (decomp.) | 61.0 (60.9 | 3.4 3.6 | 15.0 15.2) |
| 65 | —H | —H | —I | (furan) | —H | Free base, 228–231° | 73.3 (73.9 | 4.3 4.3 | 6.9 6.6) |
| 66 | —H | —CH$_3$ | —I | (pyridine) | —H | Free base, 272° | 76.4 (76.2 | 5.1 5.1 | 11.5 11.9) |
| 67 | —H | —CH$_3$ | —I | (pyridine) | —H | Free base, 0.75 H$_2$O, 300° | 72.4 (72.1 | 5.1 5.4 | 10.8 11.2) |

-continued

| Example No. | $R_a$ | $R_b$ | X | Het | $R_c$ | Form isolated and m.p. (°C.) | C | H | N |
|---|---|---|---|---|---|---|---|---|---|
| 68* | —H | —H | —I | 3-pyridyl | —H | Free base, 218–220° | 75.3 (75.7 | 4.5 4.5 | 12.2 12.6) |
| 69 | —H | —CH₃ | —Br | 2,6-dimethyl-pyridyl(CH₃ substituted) | —CH₃ | Free base, 259.5–262.5° | 77.4 (77.7 | 6.5 6.5 | 10.0 10.1) |
| 70 | —H | —H | —I | 2,6-dimethyl-pyridyl | —Et | Free base, 202–204° | 77.7 (77.7 | 6.5 6.5 | 10.0 10.1) |
| 71 | —H | —H | —I | 2,6-dimethyl-pyridyl | —CH(CH₃)₂ | Free base, 188–191.5° | 77.7 (78.0 | 6.7 6.9 | 9.6 9.6) |
| 72 | —H | —H | —Br | 2,6-dimethyl-pyridyl | —OCH₃ | Free base, 202.5–205° | 72.5 (72.8 | 5.7 5.7 | 10.0 10.0) |

*Identical to the product of Example 1.

EXAMPLES 73–75

The following compounds were prepared similarly to the procedure of Example 61 starting from 6-bromo-3,4-dihydro-2-(1H)-quinolone or 6-bromo-4-methyl-3,4-dihydro-2-(1H)-quinolone and the appropriate pyridyl-zinc chloride, with tetrakis (triphenylphosphine) palladium(O) as catalyst.

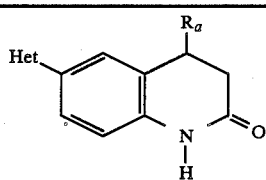

| Example No. | $R_a$ | Het | Form isolated and m.p. (°C.) | C | H | N |
|---|---|---|---|---|---|---|
| 73 | —H | 3-pyridyl | Free base, 180° | 74.8 (75.0 | 5.4 5.4 | 12.4 12.5) |
| 74 | —H | 4-pyridyl | Free base, 0.25 H₂O, 263–264° | 73.8 (73.5 | 5.4 5.5 | 12.2 12.2) |
| 75 | —CH₃ | 3-pyridyl | Free base, 179.5° | 75.5 (75.6 | 6.0 5.9 | 11.7 11.8) |

EXAMPLE 76

Preparation of 3-amino-6-(3-pyridyl)-2-(1H)-quinolone ⅔ hydrate

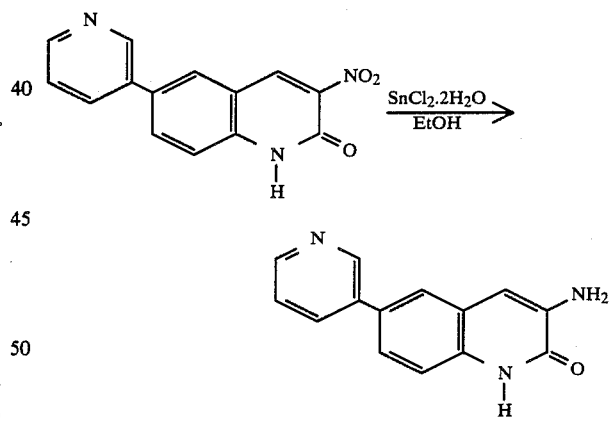

Stannous chloride dihydrate (1.27 g) was added to a stirred solution of 3-nitro-6-(3-pyridyl)-2-(1H)-quinoline (0.30 g) in ethanol (10 cm³) and the mixture was heated under reflux for 1.5 hours and then cooled. The cooled mixture was partitioned between chloroform (100 cm³) and aqueous sodium carbonate solution (50 cm³). The mixture was filtered, the layers were separated, and the aqueous phase was further extracted with chloroform-:methanol, 9:1 (2×50 cm³). The combined and dried (MgSO₄) extracts were concentrated in vacuo to afford a solid which was triturated with hot isopropanol, filtered and dried to give 3-amino-6-(3-pyridyl)-2-(1H)-quinoline, 0.66H₂O, m.p. 298°–300° (decomp.), (0.093 g).

Analysis %: Found: C, 67.8; H, 4.7; N, 16.8; Calculated for C₁₄H₁₁N₃O.0.66H₂O: C, 67.5; H, 4.9; N, 16.9.

EXAMPLE 77

Preparation of 3-bromo-6-(3-pyridyl)-2-(1H)-quinolone

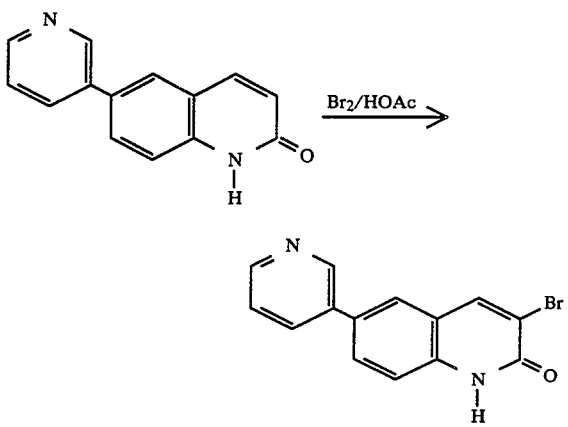

A mixture of 6-(3-pyridyl)-2-(1H)-quinolone monohydrochloride (0.50 g), bromine (3.2 g), acetic acid (10 cm³) and triethylamine (0.195 g) was heated under reflux for 24 hours and then cooled. Ether (20 cm³) was then added to the cooled reaction mixture and the resulting yellow solid was filtered off. This material was purified by preparative layer chromatography eluting with chloroform:methanol, 15:1 (4 elutions), to afford 3-bromo-6-(3-pyridyl)-2-(1H)-quinolone, m.p. 297°–300°, (0.11 g).

Analysis %: Found: C, 55.7; H, 3.1; N, 9.2; Calculated for C₁₄H₉N₂OBr: C, 55.8; H, 3.0; N, 9.3.

EXAMPLE 78

Preparation of 6-(1-oxopyrid-3-yl)-2-(1H)-quinoline ¼ hydrate

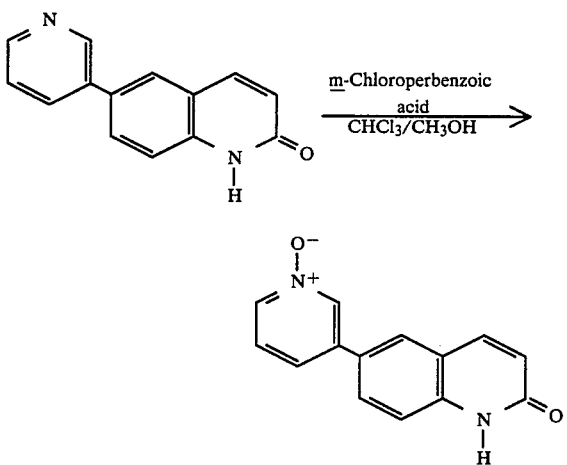

m-Chloroperbenzoic acid (3.74 g) was added to a stirred solution of 6-(3-pyridyl)-2-(1H)-quinolone (1.49 g) in chloroform (50 cm³) and methanol (50 cm³). After 16 hours, a solution of sodium hydroxide (0.90 g) in water (5 cm³) was added, followed by silica gel (Merck "MK 60.9385" [Trade Mark]; 30 g), and the mixture was evaporated to dryness in vacuo. The resulting powder was placed on top of a silica gel column (Merck "MK 60.9385") and eluted with chloroform:methanol, 9:1. The fractions containing the product were combined and evaporated to afford a solid which was recrystallised from isopropanol to give 6-(1-oxopyrid-3-yl)-2-(1H)-quinolone. 0.25H₂O, m.p. 280° (decomp.), (0.44 g).

Analysis %: Found: C, 69.4; H, 4.4; N, 11.3; Calculated for C₁₄H₁₀N₂O₂.0.25H₂O: C, 69.3; H, 4.4; N, 11.5.

EXAMPLE 79

8-Methyl-6-(1-oxopyrid-3-yl)-2-(1H)-quinolone, 0.35H₂O, m.p. 290° (decomp.), was prepared similarly to the previous Example using 8-methyl-6-(3-pyridyl)-2-(1H)-quinolone as the starting material.

Analysis %: Found: C, 69.3; H, 4.8; N, 10.6; Calculated for C₁₅H₁₂N₂O.0.35H₂O: C, 69.7; H, 4.9; N, 10.8.

EXAMPLE 80

1-Methyl-6-(3-pyridyl)-2-(1H)-quinolone 174 hydrate

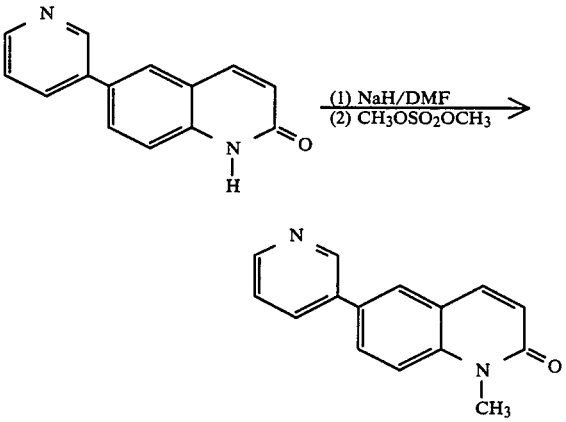

A stirred solution of 6-(3-pyridyl)-2-[1H]-quinolone (0.05 g) in DMF (0.5 cm³) was treated at room temperature with sodium hydride (0.012 g of a 50% dispersion in oil) for 1 hour. A solution of dimethyl sulphate (0.016 g) in DMF (0.2 cm³) was added and the mixture was stirred for 1.5 hours. The mixture was concentrated in vacuo, water (5 cm³) was added and the mixture was extracted with ethyl acetate (3 × 10 cm³). The combined organic extracts were dried (MgSO₄), concentrated in vacuo and the residue chromatographed on silica (Merck "MK 60.9385") eluting with chloroform to yield a solid which was triturated with ether to afford 1-methyl-6-(3-pyridyl)-2-(1H)-quinolone 0.25H₂O, m.p. 116°–118°, (0.02 g).

Analysis %: Found: C, 75.2; H, 5.3; N, 11.6; Calculated for C₁₅H₁₂N₂O.0.25H₂O: C, 74.8; H, 5.2; N, 11.6.

EXAMPLE 81

8-Methyl-6-[2,6-dimethylpyrid-3-yl]-3,4-dihydro-2-(1H)-quinolone

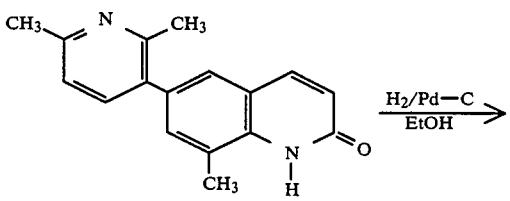

-continued

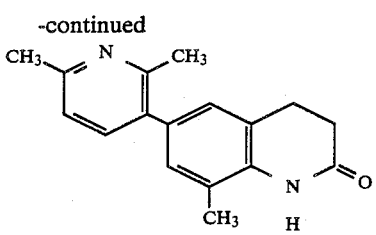

tallised from ethyl acetate/methanol to give 8-methyl-6-[2,6-dimethylpyrid-3-yl]-3,4-dihydro-2-(1H)-quinoline, m.p. 255°–258° (0.110 g).

Analysis %: Found: C, 76.2; H, 6.8; N, 10.4; Calculated for $C_{17}H_{18}N_2O$: C, 76.7; H, 6.8; N, 10.5.

EXAMPLES 82–88

The following compounds were prepared similarly to the previous Example starting from the appropriately substituted quinolone and $H_2$/Pd-C:

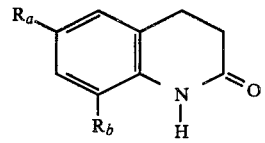

| Example No. | $R_a$ | $R_b$ | Form isolated and m.p. (°C.) | C | H | N |
|---|---|---|---|---|---|---|
| 82 | CH₃-pyridyl-CH₃ | —H | Free base, 0.5 H₂O 213–215° | 73.7 (73.5 | 6.3 6.6 | 11.1 10.7) |
| 83 | CH₃-pyridyl-CH₃ | —Et | Free base, 210–213° | 77.5 (77.1 | 7.4 7.2 | 9.9 10.0) |
| 84 | CH₃-pyridyl-CH₃ | —CH(CH₃)₂ | Free base, 185–188° | 77.4 (77.5 | 7.5 7.5 | 9.4 9.5) |
| 85 | CH₃-pyridyl-CH₃ | —OCH₃ | Free base, 195–200° | 72.1 (72.3 | 6.4 6.4 | 9.9 9.9) |
| 86 | N-methylpyrazolyl | —H | Free base, 0.33 H₂O 196–198° | 61.5 (61.5 | 5.4 5.1 | 23.9 23.7) |
| 87 | N-methylpyrazolyl | —CH₃ | Free base, 0.25 H₂O 182.5–184.5° | 63.3 (63.3 | 5.9 5.8 | 22.7 22.7) |
| 88 | N-methylpyrazolyl | —Et | Free base, 163–168° | 65.3 (65.6 | 6.0 6.3 | 22.0 21.9) |

A solution of 8-methyl-6-[2,6-dimethylpyrid-3-yl]-2-(1H)-quinolone (0.30 g) was hydrogenated at 60° and 60 p.s.i. ($4.13 \times 10^5$ Pa) pressure over 10% palladised charcoal (0.10 g) for 48 hours. The cooled solution was then filtered through "Solkafloc" (Trademark for a cellulose-based filtering aid), evaporated to dryness in vacuo, and the residue chromatographed on silica (Merck "MK 60.9385") eluting with chloroform:methanol, 49:1. Combination and evaporation of appropriate fractions afforded a solid (0.16 g) which was recrys-

EXAMPLE 89

4,8-Dimethyl-6-[2,6-dimethylpyrid-3-yl]-3,4-dihydro-2-(1H)-quinolone 0.25 H₂O, m.p. 177°–9°, was prepared similarly to Example 81 using 4,8-dimethyl-6-[2,6-dimethylpyrid-3-yl]-2-(1H)-quinolone and $H_2$/Pd-C as the starting materials.

Analysis %: Found: C, 76.3; H, 7.3; N, 10.0; Calculated for $C_{18}H_{20}N_2O \cdot 0.25H_2O$: C, 75.9; H, 7.3; N, 9.8.

EXAMPLE 90

8-Bromo-6-[2,6-dimethylpyrid-3-yl]-3,4-dihydro-2-(1H)-quinolone

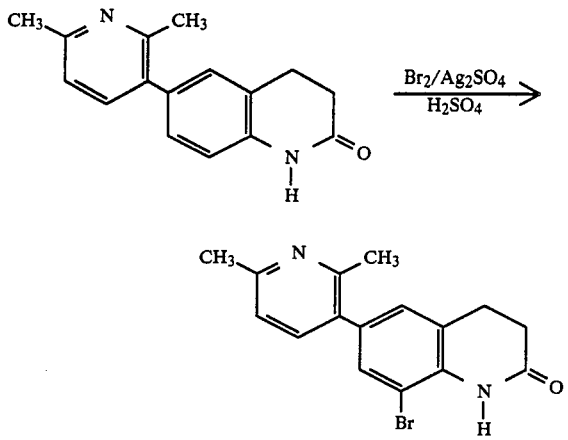

Bromine (0.46 cm³) was added at room temperature to a stirred solution of 3,4-dihydro-6-[2,6-dimethylpyrid-3-yl]-2-(1H)-quinolone (1.5 g) and silver sulphate (1.4 g), in 98% sulphuric acid (25 cm³). After warming at 50° for 16 hours, the cooled mixture was poured onto ice (100 g) and neutralised to pH7 which 5M sodium hydroxide solution. Chloroform (100 cm³) was added, the phases were separated, and the aqueous phase was further extracted with chloroform (2×100 cm³). The combined and dried (MgSO₄) extracts were evaporated in vacuo to give a solid (1.9 g). A small portion of this material was recrystallised from ethyl acetate/methanol to afford 8-bromo-6-[2,6-dimethylpyrid-3-yl]-3,4-dihydro-2-(1H)-quinolone, m.p. 194°-195°.

Analysis %: Found: C, 57.7; H, 4.4; N, 8.7; Calculated for $C_{16}H_{15}N_2OBr$: C, 58.0; H, 4.6; N, 8.5.

EXAMPLE 91

8-Bromo-6-[1-methyl-1,2,4-triazol-5-yl]-3,4-dihydro-2-(1H)-quinolone, m.p. 160°-163°, was prepared similarly to the previous Example using 6-[1-methyl-1,2,4-triazol-5-yl]-3,4-dihydro-2-(1H)-quinolone, bromine and silver sulphate in sulphuric acid as the starting materials.

Analysis %: Found: C, 46.8; H, 3.6; N, 18.3; Calculated for $C_{12}H_{11}BrN_4O$: C, 46.9; H, 3.6; N, 18.2.

EXAMPLE 92

8-Bromo-6-[2,6-dimethylpyrid-3-yl]-2-(1H)-quinolone

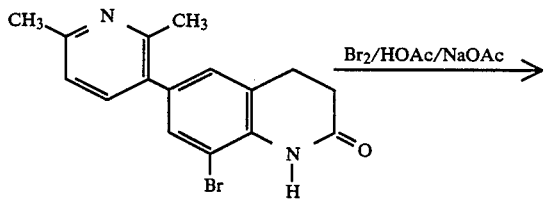

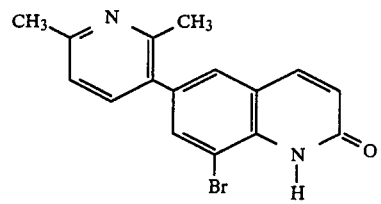

Bromine (0.33 cm³) was added at room temperature to a stirred suspension of 8-bromo-6-[2,6-dimethylpyrid-3-yl]-3,4-dihydro-2-(1H)-quinolone (1.9 g) and sodium acetate (1.06 g) in acetic acid (50 cm³). After warming 100° for 18 hours, the cooled solution was evaporated in vacuo and the residue was partitioned between 10% sodium carbonate solution (50 cm³) and chloroform (100 cm³). The aqueous phase was further extracted with chloroform (3×100 cm³) and the combined and dried (MgSO₄) extracts were concentrated in vacuo to give a solid which was chromatographed on silica (Merck "MK 60.9385" [Trade Mark]) eluting with chloroform. Combination and evaporation of the appropriate fractions afforded a solid (0.80 g) which was recrystallised from ethyl acetate/methanol to give 8-bromo-6-[2,6-dimethylpyrid-3-yl]-2-(1H)-quinolone, m.p. 212°-215° (0.55 g).

Analysis %: Found: C, 58.2; H, 4.0; N, 8.5; Calculated for $C_{16}H_{13}BrN_2O$: C, 58.4; H, 4.0; N, 8.5.

EXAMPLE 93

8-Bromo-6-[1-methyl-1,2,4-triazol-5-yl]-2-(1H)-quinolone, m.p. 257°-259°, was prepared similarly to the previous Example using 8-bromo-6-[1-methyl-1,2,4-triazol-5-yl]-3,4-dihydro-2-(1H)-quinolone, bromine and sodium acetate in acetic acid as the starting materials.

Analysis %: Found: C, 47.0; H, 3.0; N, 18.2; Calculated for $C_{12}H_9BrN_4O$: C, 47.2; H, 3.0; N, 18.4.

EXAMPLE 94

6-[2,6-Dimethylpyrid-3-yl]-8-thiomethyl-2-(1H)-quinolone ¼ hydrate

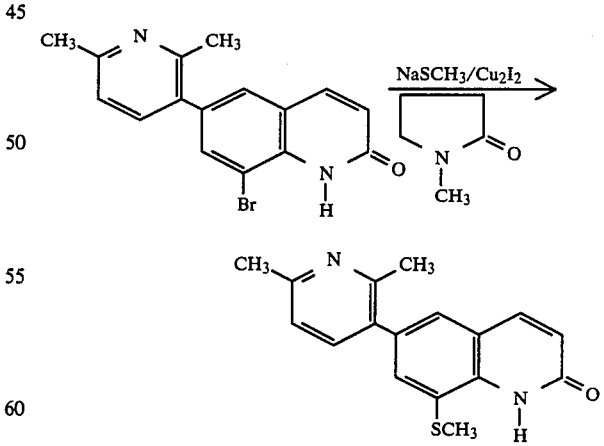

A solution of sodium methanethiolate (15 cm³ of a 2.0M solution in methanol) was added at room temperature to a solution of 8-bromo-6-[2,6-dimethylpyrid-3-yl]-2-(1H)-quinolone (0.50 g) and cuprous iodide (0.15 g) in N-methyl-2-pyrollidone (12 cm³). After heating at 160° for 48 hours the cooled mixture was diluted with chloroform (100 cm³) and water (50 cm³). The separated aqueous phase was further extracted with chloroform (3×50 cm³), and the combined and dried (MgSO₄) chloroform extracts were evaporated in vacuo to given an oil which was chromatographed on silica (Merck "MK 60.9385" [Trade Mark]) eluting with chloroform. Combination and evaporation of appropriate fractions gave a solid which was recrystallised from ethyl acetate to afford 6-[2,6-dimethyl-pyrid-3-yl]-8-thiomethyl-2-(1H)-quinolone 0.25 H₂O, m.p. 146.5°–148.5° (0.04 g).

Analysis %: Found: C, 67.9; H, 5.6; N, 9.4; Calculated for $C_{18}H_{16}N_2OS \cdot 0.25H_2O$: C, 67.9; H, 5.5; N, 9.3.

EXAMPLE 95

6-[1-Methyl-1,2,4-triazol-5-yl]-8-thiomethyl-2-(1H)-quinolone, 0.33H₂O, m.p. 203°–205°, was prepared similarly to the previous Example using 8-bromo-6-[1-methyl-1,2,4-triazol-5-yl]-2-(1H)-quinolone, sodium methanethiolate and cuprous iodide as the starting materials.

Analysis %: Found: C, 56.1; H, 4.5; N, 19.7; Calculated for $C_{13}H_{12}N_4OS \cdot 0.33H_2O$: C, 56.1; H, 4.5; N, 20.1.

EXAMPLE 96

8-Methylsulphinyl-6-[1-methyl-1,2,4-triazol-5-yl]-2-(1H)-quinolone

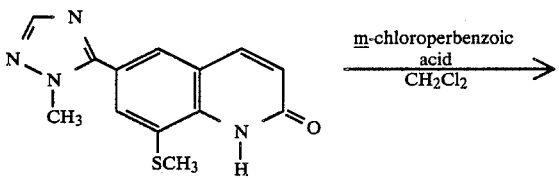

m-Chloroperbenzoic acid (0.14 g) was added at 0° to a stirred solution of 6-[1-methyl-1,2,4-triazol-5-yl]-8-thiomethyl-2-(1H)-quinolone in dichloromethane (10 cm³). After 0.5 hours the solution was concentrated in vacuo, and the residue was chromatographed on silica (Merck "MK 60.9385" [Trade mark]) eluting with chloroform:methanol, 19:1. Combination and evaporation of the appropriate fractions gave a solid which was recrystallised from ethyl acetate to afford 8-methylsulphinyl-6-[1-methyl-1,2,4-triazol-5-yl]-2-(1H)-quinolone, m.p. 224°–227° (0.086 g).

Analysis %: Found: C, 53.8; H, 4.3; N, 19.3. Calculated for $C_{13}H_{12}N_4O_2S$: C, 54.2; H, 4.2; N, 19.4.

EXAMPLE 97

8-Methylsulphonyl-6-[1-methyl-1,2,4-triazol-5-yl]-2-(1H)-quinolone

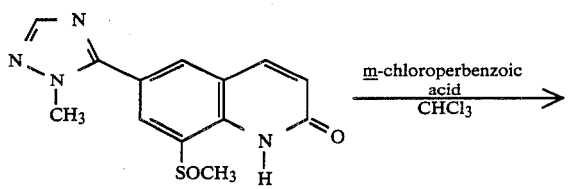

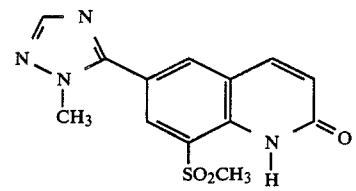

A mixture of 8-methylsulphinyl-6-[1-methyl-1,2,4-triazol-5-yl]-2-(1H)-quinolone (0.097 g) and m-chloroperbenzoic acid (0.088 g) in chloroform (10 cm³) was stirred for 18 hours at room temperature. The mixture was then concentrated in vacuo and the residue was chromatographed on silica (Merck "MK 60.9385" [Trade Mark]), eluting with ethyl acetate:methanol, 19:1. Combination and evaporation of the appropriate fractions afforded a solid which was recrystallised from dichloromethane/hexane to give 8-methylsulphonyl-6-[1-methyl-1,2,4-triazol-5-yl]-2-(1H)-quinolone, m.p. 226°–232° (0.051 g).

Analysis %: Found: C, 51.0; H, 4.1; N, 17.6; Calculated for $C_{13}H_{12}N_4O_3S$: C, 51.3; H, 4.0; N, 18.4.

EXAMPLE 98

8-Hydroxy-6-[2,6-dimethylpyrid-3-yl]-2-(1H)-quinolone

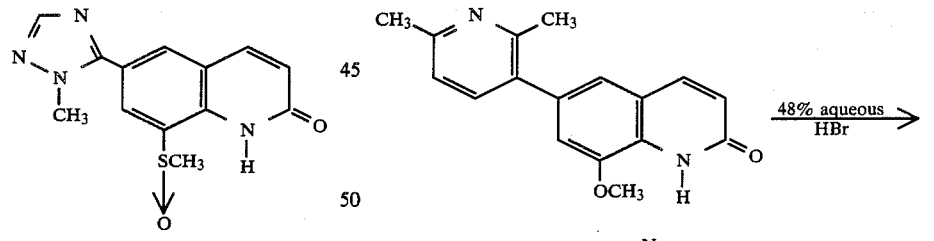

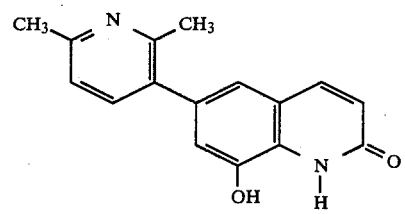

A mixture of 8-methoxy-6-[2,6-dimethylpyrid-3-yl]-2-(1H)-quinolone (0.15 g) and 48% aqueous HBr (5 cm³) was heated under reflux for 19 hours. The mixture was diluted with water (20 cm³), basified to pH7 with 5M sodium hydroxide solution, and extracted with CHCl₃ (3×50 cm³). The combined and dried (MgSO₄) chloroform extracts were evaporated in vacuo to afford a solid which was recrystallised from ethyl acetate to give 8-hydroxy-6-[2,6-dimethylpyrid-3-yl]-2-(1H)-quinolone, m.p. 276°-277°, (0.132 g).

Analysis %: Found: C, 71.8; H, 5.4; N, 10.3; Calculated for $C_{16}H_{14}N_2O_2$: C, 72.2; H, 5.3; N, 10.5.

EXAMPLE 99

8-Hydroxy-6-[2,6-dimethylpyrid-3-yl]-3,4-dihydro-2-(1H)-quinolone 0.5H₂O, m.p. 178°-185°, was prepared similarly to the previous Example using 8-methoxy-6-[2,6-dimethylpyrid-3-yl]-3,4-dihydro-2-(1H)-quinolone and 48% HBr as the starting materials.

Analysis %: Found: C, 69.8; H, 6.3; N, 9.4; Calculated for $C_{16}H_{16}N_2O_2.0.5H_2O$: C, 71.6; H, 6.0; N, 10.4.

EXAMPLE 100

8-Hydroxy-6-[1-methyl-1,2,4-triazol-5-yl]-2-(1H)-quinolone, m.p. 312°-3°, was prepared similarly to Example 98 using 8-methoxy-6-[1-methyl-1,2,4-triazol-5-yl]-2-(1H)-quinolone and 48% HBr as the starting materials.

Analysis %: Found: C, 59.2; H, 4.1; N, 23.4; Calculated for $C_{12}H_{10}N_4O_2$: C, 59.5; H, 4.2; N, 23.1.

The following Preparations illustrate the synthesis of the novel starting materials. All temperatures are in °C.:

PREPARATION 1

2-Methoxy-6-bromoquinoline

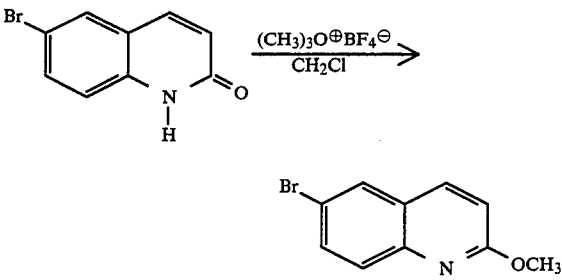

A mixture of 6-bromo-2-[1H]-quinolone (2.90 g) and trimethyloxoniumtetrafluoroborate (2.10 g) was stirred in dichloromethane (50 cm³) for 48 hours under nitrogen. Aqueous 10% sodium hydroxide (20 cm³) was added and the aqueous phase was extracted with dichloromethane (2×40 cm³). The dried (MgSO₄) extracts were evaporated and the residue was crystallised from petroleum ether (b.p. 60°-80°) to yield 2-methoxy-6-bromoquinoline, m.p. 90°-94°, (2.16 g).

Analysis %: Found: C, 50.7; H, 3.5; N, 6.0. Calculated for $C_{10}H_8NOBr$: C, 50.4; H, 3.4; N, 5.9.

PREPARATION 2

2-Methoxy-6-bromoquinoline (alternative to Preparation 1)

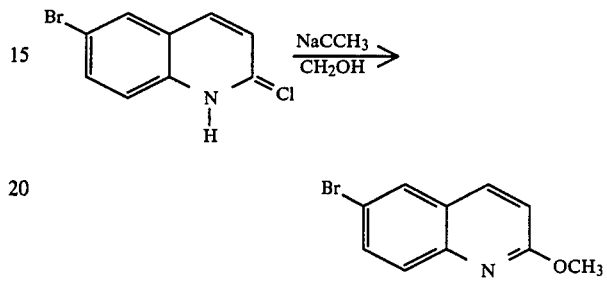

A solution of 2-chloro-6-bromoquinoline (4.0 g) in methanol (20 cm³) was heated under reflux with sodium methoxide [made from sodium (0.5 g) and methanol (20 cm³)] for 16 hours. The solvent was removed in vacuo and the residue was partitioned between water (20 cm³) and chloroform (100 cm³). The aqueous phase was extracted with chloroform (2×30 cm³) and the dried (MgSO₄) extracts were evaporated to give a solid which was recrystallised from petroleum ether (b.p. 60°-80°) to yield 2-methoxy-6-bromoquinoline, m.p. 93°-96°, (3.0 g).

Analysis %: Found: C, 50.4; H, 3.4; N 6.0; Calculated for $C_{10}H_8NOBr$: C, 50.4; H, 3.4; N, 5.9.

PREPARATIONS 3-9

The following compounds were prepared similarly to Preparation 2 using the appropriately substituted 2-chloroquinoline derivative and sodium methoxide in methanol as the starting materials:

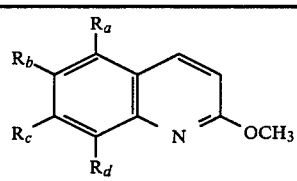

| Preparation No. | $R_a$ | $R_b$ | $R_c$ | $R_d$ | Form isolated and m.p. (°C.) | C | H | N |
|---|---|---|---|---|---|---|---|---|
| 3 | —Br | —H | —H | —H | Free base, 86-87° | 50.4 (50.4 | 3.4 3.4 | 6.1 5.9) |
| 4 | —H | —Br | —H | —CH₃ | Free base, 89-91° | 52.2 (52.4 | 3.9 4.0 | 5.7 5.6) |
| 5 | —H | —H | —Br | —H | Free base, 71-72° | 50.4 (50.4 | 3.4 3.4 | 6.3 5.9) |
| 6 | —H | —Br | —CH₃ | —H | Free base, 71-74° | 52.3 (52.4 | 4.0 4.0 | 5.8 5.6) |
| 7 | —H | —I | —H | —Et | Free base, 40° | 47.1 (46.0 | 4.1 3.9 | 4.5 4.5) |
| 8 | —H | —I | —H | —CH(CH₃)₂ | Free base, 64-66° | 47.9 (47.7 | 4.3 4.3 | 4.3 4.3) |
| 9 | —H | —Br | —H | —OCH₃ | Free base 0.25 H₂O, | 48.6 (48.5 | 3.7 3.9 | 5.0 5.1) |

-continued

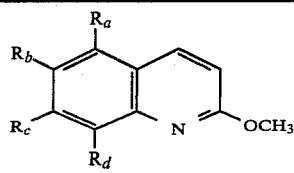

| Preparation No. | $R_a$ | $R_b$ | $R_c$ | $R_d$ | Form isolated and m.p. (°C.) | Analysis % (Theoretical in brackets) C H N |
|---|---|---|---|---|---|---|
| | | | | | 101.5–102.5 | |

PREPARATION 10

6-Bromo-4,8-dimethyl-2-methoxyquinoline, 0.25H$_2$O, m.p. 105°, was prepared similarly to Preparation 2 using 6-bromo-2-chloro-4,8-dimethylquinoline and sodium methoxide in methanol as the starting materials.

Analysis %: Found: C, 53.1; H, 4.4; N, 5.2; Calculated for C$_{12}$H$_{12}$BrNO.0.25H$_2$O: C, 53.2; H, 4.6; N, 5.2.

PREPARATION 11

2-Methoxy-8-methyl-6-(3-pyridyl)quinoline

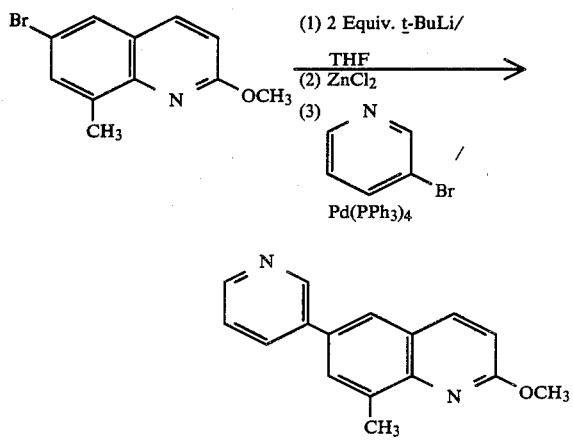

t-Butyl lithium (8.0 cm$^3$ of a 2.0M solution in pentane) was added dropwise to a stirred solution of 6-bromo-2-methoxy-8-methylquinoline (2.0 g) in THF (20 cm$^3$) at $-70°$ under nitrogen. After 10 minutes the mixtures was treated with a solution of anhydrous zinc chloride (1.09 g) in THF (10 cm$^3$) and the resulting solution was warmed to 0°. A solution containing 3-bromopyridine (1.26 g) and tetrakis(triphenylphosphine) palladium(O) (0.05 g) in THF (10 cm$^3$) was then added and the mixture was heated under reflux for 2 hours. The reaction mixture was cooled, concentrated in vacuo, treated with chloroform (100 cm$^3$) and a solution of ethylenediaminetetraacetic acid disodium salt (6 g) in water (100 cm$^3$). The aqueous phase was extracted further with chloroform (3×50 cm$^3$) and the combined and dried (MgSO$_4$) extracts were concentrated in vacuo to give an oil. This oil was chromatographed on silica (Merck "MK 60.9385") eluting with ethyl acetate. The fractions containing the product were combined and evaporated to afford a solid which was recrystallised from hexane to afford 2-methoxy-8-methyl-6-(3-pyridyl)quinoline, m.p. 117°–118.5°, (1.12 g).

Analysis %: Found: C, 76.5; H, 5.7; N, 11.0; Calculated for C$_{16}$H$_{14}$N$_2$O: C, 76.8; H, 5.6; N, 11.2.

PREPARATION 12–40

The following compounds were prepared similarly to the previous Preparation using the appropriate bromo-substituted heterocycle and the appropriately substituted 2-methoxyquinoline as starting materials.

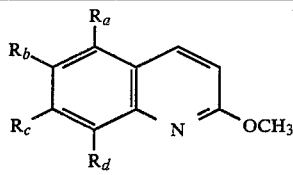

| Preparation No. | $R_a$ | $R_b$ | $R_c$ | $R_d$ | Form isolated and m.p. (°C.) | Analysis % (Theoretical in brackets) | | |
|---|---|---|---|---|---|---|---|---|
| | | | | | | C | H | N |
| 12 | —H | 3-pyridyl | —H | —H | Free base, 89–91° | 76.4 (76.2 | 5.1 5.1 | 11.6 11.9) |
| 13 | —H | 2,6-dimethyl-pyridyl | —H | —H | Free base, 88–90° | 76.7 (77.2 | 6.6 6.1 | 10.3 10.6) |

-continued

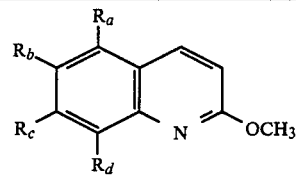

| Preparation No. | $R_a$ | $R_b$ | $R_c$ | $R_d$ | Form isolated and m.p. (°C.) | C | H | N |
|---|---|---|---|---|---|---|---|---|
| 14 | —H | 4-pyridyl | —H | —CH₃ | Free base, 83.5–85.5° | 76.8 (76.8 | 5.6 5.6 | 11.2 11.2) |
| 15 | —H | 2-methyl-5-pyridyl | —H | —H | Free base, 101–103° | 76.6 (76.8 | 5.6 5.6 | 11.3 11.2) |
| 16 | —H | 2,3-dimethyl-pyridyl | —H | —H | Free base, 99–101° | 76.7 (76.8 | 5.8 5.6 | 11.4 11.2) |
| 17 | —H | thiazolyl | —H | —H | Free base, 90–91° | 65.0 (64.4 | 4.2 4.2 | 11.3 11.6) |
| 18 | —H | 2-amino-5-pyridyl | —H | —H | Free base, 182–183° | 71.3 (71.7 | 5.2 5.2 | 16.7 16.7) |
| 19 | —H | 2-pyrimidinyl | —H | —CH₃ | Free base, 131.5–132.5 | 71.7 (71.7 | 5.2 5.2 | 16.5 16.7) |
| 20 | —H | 2,6-dimethyl-3-methyl-pyridyl | —H | —CH₃ | Free base, 0.33 H₂O 74–76° | 75.9 (76.0 | 6.4 6.6 | 9.7 9.8) |
| 21 | —H | 2,6-dimethyl-pyridyl | —H | —CH₃ | Crude free base, oil | — | — | — |
| 22 | —H | 2,3-dimethyl-pyridyl | —H | —CH₃ | Free base, 72.5–74.5 | 77.4 (77.3 | 6.2 6.1 | 10.4 10.6) |
| 23 | 3-pyridyl | —H | —H | —H | Free base, 74–76° | 76.0 (76.2 | 5.2 5.1 | 11.7 11.9) |
| 24 | 2-pyridyl | —H | —H | —H | Crude free base, oil | — | — | — |

-continued

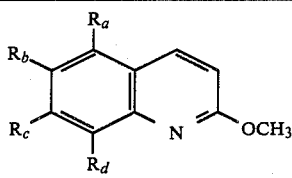

| Preparation No. | $R_a$ | $R_b$ | $R_c$ | $R_d$ | Form isolated and m.p. (°C.) | C | H | N |
|---|---|---|---|---|---|---|---|---|
| 25 | —H | —H | 2-pyridyl | —H | Free base, 0.1 H$_2$O, 79–81° | 75.7 (75.7 | 5.1 5.2 | 11.8 11.8) |
| 26 | —H | —H | 3-pyridyl | —H | Free base, 0.15 H$_2$O, 84–87° | 75.4 (75.4 | 5.2 5.2 | 11.2 11.7) |
| 27 | —H | —H | 4-pyridyl | —H | Free base, 0.25 H$_2$O, 116–117° | 75.2 (74.8 | 5.3 5.2 | 11.6 11.6) |
| 28 | —H | 2-pyridyl | —CH$_3$ | —H | Free base, 80–82° | 76.6 (76.8 | 5.6 5.6 | 11.0 11.2) |
| 29 | —H | 3-pyridyl | —CH$_3$ | —H | Free base, 61–63° | 76.0 (76.8 | 5.6 5.6 | 11.2 11.2) |
| 30 | —H | 4-pyridyl | —CH$_3$ | —H | Free base, 161–163° | 76.5 (76.8 | 5.7 5.6 | 11.2 11.2) |
| 31 | —H | 2-methyl-3-pyridyl | —CH$_3$ | —H | Crude free base, oil | — | — | — |
| 32 | —H | thienyl | —H | —H | Free base, 141.5–143° | 69.4 (69.7 | 4.6 4.6 | 5.8 5.8) |
| 33 | —H | 5-cyano-3-pyridyl | —H | —CH$_3$ | Free base, 220–222° | 73.8 (74.2 | 4.9 4.8 | 15.6 15.3) |
| 34 | —H | 2-methyl-5-pyridyl | —H | —CH$_3$ | Free base, 111.5–114° | 77.1 (77.3 | 6.1 6.1 | 10.4 10.6) |
| 35 | —H | 6-methyl-2-pyridyl | —H | —H | Free base, 83–84° | 76.2 (76.2 | 5.2 5.1 | 11.9 11.9) |

-continued

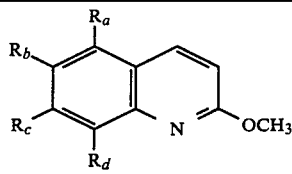

| Preparation No. | $R_a$ | $R_b$ | $R_c$ | $R_d$ | Form isolated and m.p. (°C.) | C | H | N |
|---|---|---|---|---|---|---|---|---|
| 36 | —H | 4-pyridyl | —H | —H | Zinc complex* 254–257° | Not characterised | | |
| 37 | —H | 3-methylpyrid-4-yl | —H | —H | Crude free base, oil | Not characterised | | |
| 38 | —H | 4-methylpyrid-3-yl | —H | —H | Crude free base, oil | Not characterised | | |
| 39 | —H | pyrimidin-5-yl | —H | —H | Free base, 165–168° | 70.5 (70.9 | 4.6 4.7 | 17.6 17.7) |
| 40 | —H | pyrimidin-2-yl | —H | —H | Free base, 139–140° | 70.6 (70.9 | 4.4 4.7 | 17.7 17.7) |

*Preparation 36 gave a stable complex containing zinc chloride whose structure was not rigorously characterised. This material was used directly in Example 3.

PREPARATION 41 (Alternative to Preparation 20)

8-Methyl-6-[2,6-dimethylpyrid-3-yl]-2-methoxyquinoline 0.33 H₂O

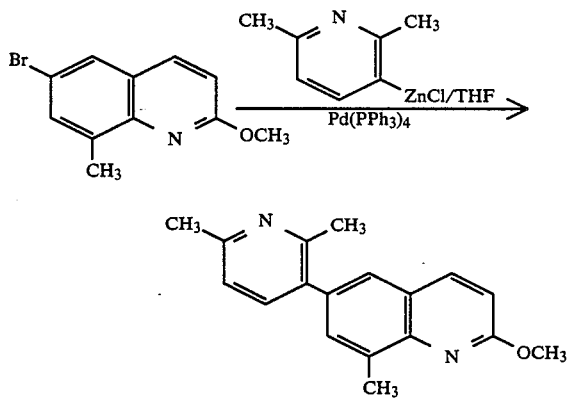

A solution of 3-bromo-2,6-dimethylpyridine (0.935 g) in tetrahydrofuran (THF) (5 cm³) was added dropwise to a stirred suspension of magnesium turnings (0.133 g) and iodine (0.005 g) in THF (5 cm³) under reflux. The magnesium was completely consumed after heating for a further 1 hour and the solution was then cooled to 0° during the addition of a solution of anhydrous zinc chloride (0.680 g) in THF (4 cm³). After 0.5 hours a solution of 6-bromo-8-methyl-2-methoxyquinoline (1.25 g) and tetrakis-(triphenylphosphine)palladium(O) (0.05 g) in THF (10 cm³) was added and the mixture was heated under reflux for 4 hours. The cooled mixture was partitioned between chloroform (100 cm³) and ethylenediaminetetraacetic acid disodium salt (4 g) in water (80 cm³). The aqueous phase was further extracted with chloroform (2×50 cm³) and the combined and dried (MgSO₄) extracts were evaporated in vacuo to give an oil which was chromatographed on silica (Merck "MK 60.9385") eluting with chloroform. Combination and evaporation of appropriate fractions gave an oil (1.04 g) which crystallised on trituration with hexane to afford 8-methyl-6-[2,6-dimethyl-pyrid-3-yl]-2-methoxyquinoline 0.33 H₂O, m.p. 74°–6°.

Analysis %: Found: C, 76.5; H, 6.4; N, 9.7; Calculated for $C_{18}H_{18}N_2O \cdot 0.33H_2O$: C, 76.0; H, 6.6; N, 9.8.

PREPARATION 42 (Alternative to Preparation 12)

2-Methoxy-6-(3-pyridyl)-quinoline

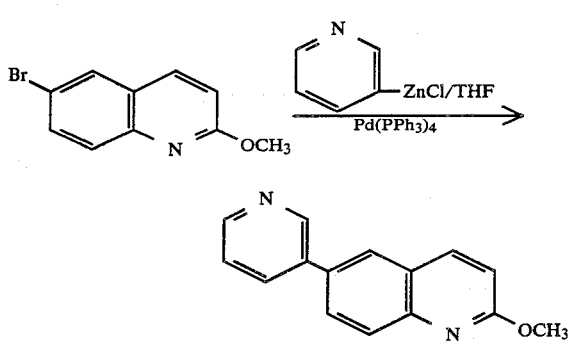

t-Butyl lithium (7.7 cm³ of a 2.6M solution in pentane) was added dropwise over 5 minutes to a stirred solution of 3-bromopyridine (1.44 cm³) in THF (25 cm³) at −100° under nitrogen. After stirring for 10 minutes a solution of anhydrous zinc chloride (2.05 g) in THF (20 cm³) was added slowly and the mixture was allowed to warm to room temperature over 1 hour. A solution of 2-methoxy-6-bromoquinoline (2.38 g) and tetrakis-(triphenylphosphine)palladium(O) (0.08 g) in THF (10 cm³) was added and the mixture was heated under reflux for 9 hours. Ammonium chloride solution (20 cm³) was then added, the mixture was concentrated in vacuo, and the aqueous phase extracted with chloroform (3×50 cm³). The dried (MgSO₄) extracts were evaporated in vacuo to give a solid which was chromatographed on silica (Merck "MK. 60.9385") eluting with ethyl acetate:hexane, 1:1, to afford a residue which was recrystallised from petroleum ether (b.p. 60°-80°)-ether to afford 2-methoxy-6-(3-pyridyl)quinoline, m.p. 89°-91°, (0.35 g).

Analysis %: Found: C, 76.4; H, 5.1; N, 11.6. Calculated for $C_{15}H_{12}N_2O$: C, 76.2; H, 5.1; N, 11.9.

PREPARATIONS 43–46

The following compounds were prepared similarly to the method of the previous Preparation using the appropriate bromopyridine and 6-bromo-3-cyano-2-methoxyquinoline (Preparations 43 and 44) or 6-bromo-2-methoxy-3-methoxycarbonylquinoline (Preparations 45 and 46) as starting materials:

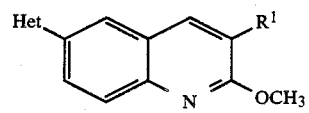

| Preparation No. | Het | R¹ | Form isolated and m.p. (°C.) | Analysis % (Theoretical in brackets) C | H | N |
|---|---|---|---|---|---|---|
| 43 | 3-pyridyl | —CN | zinc complex*, 266-268° | Not characterised | | |
| 44 | 4-pyridyl | —CN | 0.5 H₂O, 210-212° | 71.4 (71.1 | 4.3 4.4 | 15.3 15.5) |
| 45 | 3-pyridyl | —CO₂CH₃ | zinc complex*, 175° (decomp.) | Not characterised | | |
| 46 | 4-pyridyl | —CO₂CH₃ | Free base, 129-131° | 69.5 (69.4 | 5.0 4.8 | 9.2 9.5) |

*Preparations 43 and 45 gave stable complexes containing zinc chloride whose structures were not rigorously characterised. These materials were used directly as in Examples 12 and 14.

PREPARATION 47

2-Methoxy-6-(4-pyrimidinyl)quinoline

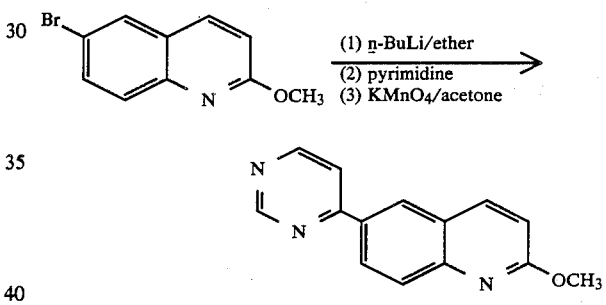

n-Butyl lithium (2.7 cm³ of a 1.5M solution in hexane) was added dropwise to a stirred suspension of 2-methoxy-6-bromoquinoline (0.95 g) in ether (5 cm³) at −70° under nitrogen. When all the solid material had dissolved a solution of pyrimidine (0.32 g) in ether (1 cm³) was added dropwise and the resulting solution was allowed to warm to room temperature. Saturated ammonium chloride solution (5 cm³) was added, the aqueous phase was extracted with chloroform (3×10 cm³) and the dried (MgSO₄) extracts were concentrated in vacuo to give an oil. This residue was taken into acetone and treated dropwise with a solution of potassium permanganate (0.63 g) in acetone until the purple colour persisted. The mixture ws filtered through "Solkafloc" (Trademark) and concentrated in vacuo to give an oil which was chromatographed on silica (Merck "MK. 60.9385" [Trademark]) eluting with ethyl acetate:hexane, 1:1, to give a solid. Recrystallisation from ethyl acetate gave 2-methoxy-6-(4-pyrimidinyl)quinoline, m.p. 164°-165°, (0.54 g).

Analysis %: Found: C, 70.5; H, 5.0; N, 17.9. Calculated for $C_{14}H_{11}N_3O$: C, 70.9; H, 4.7; N, 17.7.

PREPARATIONS 48 AND 49

The following compounds were prepared similarly to the previous Preparation using pyridazine and 2-methoxy-6-lithioquinoline as starting materials. In this case a mixture of 2-methoxy-6-(4-pyridazinyl)quinoline and 2-methoxy-6-(3-pyridazinyl)quinoline was formed which was separated by chromatography on silica (Merck "MK. 60.9385") eluting with ethyl acetate.

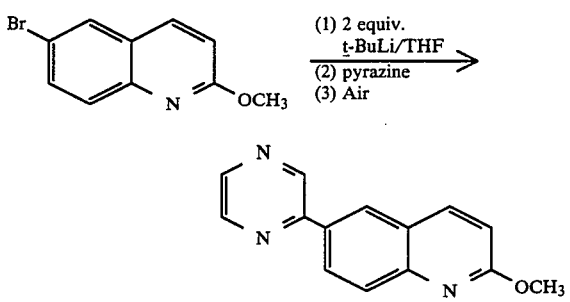

| Preparation No. | Het | Form isolated and m.p. (°C.) | Analysis % (Theoretical in brackets) | | |
|---|---|---|---|---|---|
| | | | C | H | N |
| 48 | (pyridazin-4-yl) | 0.25 H₂O, 162–163° | 69.8 (69.6 | 4.7 4.8 | 17.6 17.4) |
| 49 | (pyridazin-3-yl) | Free base, 186–187° | 71.2 (70.9 | 4.7 4.7 | 17.7 17.7) |

PREPARATION 50

2-Methoxy-6-(pyrazin-2-yl)quinoline ¼ hydrate

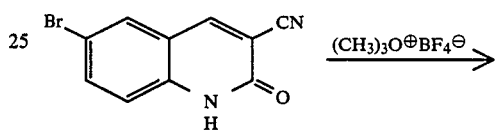

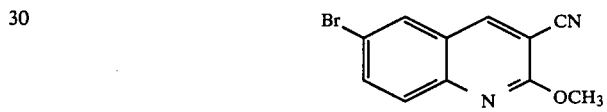

t-Butyl lithium (4.6 cm³ of a 2.6M solution in pentane) was added dropwise to a stirred solution of 2-methoxy-6-bromoquinoline (1.43 g) in THF (10 cm³) at −70° under nitrogen. After 20 minutes a solution of pyrazine (0.48 g) in THF (5 cm³) was added and after stirring for a further 20 minutes a stream of dry air was bubbled through the solution for 0.5 hour at −70° and then for a further 1 hour as the mixture warmed to room temperature. Chloroform (50 cm³) was added and the solution was washed with water (10 cm³), dried (MgSO₄) and concentrated in vacuo to afford a residue which was chromatographed on silica (Merck "MK 60.9385") eluting with ethyl acetate:hexane, 1:1, to give a solid. Recrystallisation from ethyl acetate gave 2-methoxy-6-(2-pyrazinyl)quinoline. ¼H₂O, m.p. 130°–132°, (0.22 g).

Analysis %: Found: C, 69.9; H, 4.6; N, 17.1. Calculated for $C_{14}H_{11}N_3 \cdot 1/4H_2O$: C, 69.9; H, 4.8, N, 17.4.

PREPARATION 51

3-Cyano-6-bromo-2-(1H)-quinolone

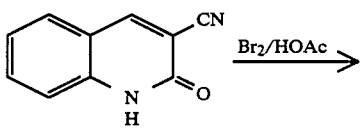

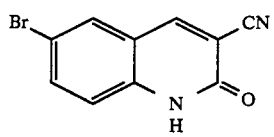

A suspension of 3-cyano-2-[1H]-quinolone (13.3 g) in acetic acid (130 cm³) was treated at room temperature with a solution of bromine (4.1 cm³) in acetic acid (10 cm³). After heating under reflux for 4 hours the mixture was cooled to room temperature, filtered, and the solid washed with ethanol to give 3-cyano-6-bromo-2-[1H]-quinolone (14.63 g), a small quantity of which was recrystallised from ethanol, m.p. 308°–311°.

Analysis %: Found: C, 48.6; H, 2.1; N, 11.4. Calculated for $C_{10}H_5N_2OBr$: C, 48.2; H, 2.0; N, 11.3.

PREPARATION 52

6-Bromo-3-cyano-2-methoxyquinoline

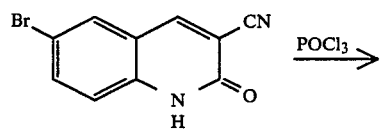

A suspension of 6-bromo-3-cyano-2-[1H]-quinolone (14.6 g) in dichloromethane (150 cm³) was stirred under nitrogen with trimethyloxonium tetrafluoroborate (10.35 g) for 2 days. A solution of 2M sodium hydroxide (100 cm³) was added and the aqueous phase was extracted with dichloromethane (3×200 cm³). The dried (MgSO₄) extracts were concentrated in vacuo and the residue chromatographed on silica (Merck "MK 60.9385") eluting with hexane:ethyl acetate, 4:1, to give a solid which was recrystallised from ethyl acetate to afford 6-bromo-3-cyano-2-methoxyquinoline, m.p. 169°–172°, (1.96 g).

Analysis %: Found: C, 50.4; H, 2.8; N, 10.8. Calculated for $C_{11}H_7N_2OBr$: C, 50.2; H, 2.7; N, 10.7.

PREPARATION 53

2-Chloro-6-Bromo-3-cyano-quinoline

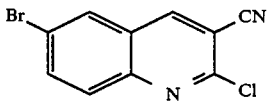

6-Bromo-3-cyano-2-[1H]-quinolone (142 g) was heated under reflux in phosphorus oxychloride (500 cm³) for 1.5 hours. Volatile material was removed in vacuo and the solid residue was taken into chloroform (400 cm³) and the resulting slurry was poured onto ice. The mixture was neutralised with aqueous ammonia solution (S.G. 0.880) and the aqueous phase was extracted further with chloroform (2×150 cm³). The dried (MgSO₄) organic extracts were concentrated in vacuo and the residue chromatographed on silica (Merck "MK 60.9385") eluting with toluene to give a solid which was recrystallised from ethyl acetate to afford 2-chloro-6-bromo-3-cyano-quinoline, m.p. 228°–230°, (80 g).

Analysis %: Found: C, 44.6; H, 1.5; N, 10.6. Calculated for $C_{10}H_5ClBrN_2$: C, 44.9; H, 1.5; N, 10.5.

PREPARATION 54 (Alternative to Preparation 52)

6-Bromo-3-cyano-2-methoxyquinoline

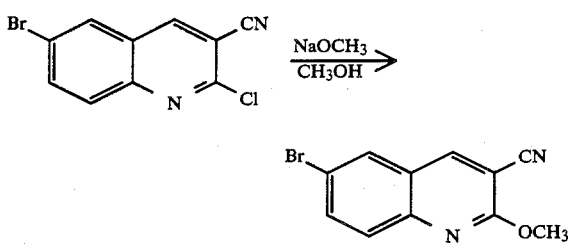

A solution of 6-bromo-2-chloro-3-cyano-quinoline (1.2 g) in methanol (30 cm³) was heated under reflux for 16 hours with sodium methoxide [made from sodium (0.116 g) and methanol (20 cm³)]. The mixture was cooled to 0° and the solid filtered to afford 6-bromo-3-cyano-2-methoxyquinoline, m.p. 172°–174°, (0.60 g).

Analysis %: Found: C, 49.8; H, 2.8; N, 10.4. Calculated for $C_{11}H_7N_2OBr$: C, 50.2; H, 2.7; N, 10.7.

PREPARATION 55

Also synthesised by a similar method to the previous Preparation starting from 6-bromo-2-chloro-3-methoxycarbonyl-quinoline was 6-bromo-2-methoxy-3-methoxycarbonyl-quinoline, m.p. 144°–145°.

Analysis %: Found: C, 49.0; H, 3.5; N, 5.1. Calculated for $C_{12}H_{10}BrNO_3$: C, 48.7; H, 3.4; N, 4.7.

PREPARATION 56

6-Bromo-2-(1H)-quinolone-3-carboxylic acid

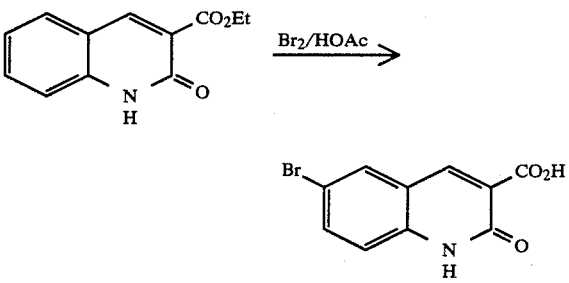

A stirred solution of 3-ethoxycarbonyl-2-[1H]-quinolone (4.5 g) in acetic acid (50 cm³) was treated at room temperature with a solution of bromine (16 g) in acetic acid (20 cm³). The mixture was heated under reflux for 24 hours, cooled and filtered to give 6-bromo-2-[1H]-quinolone-3-carboxylic acid, m.p. >300°, (3.42 g) as a crude solid.

PREPARATION 57

6-Bromo-2-chloro-3-methoxycarbonylquinoline

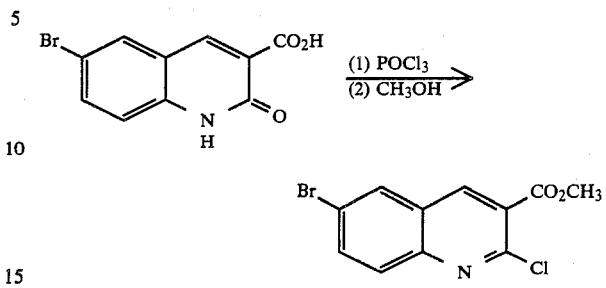

A stirred suspension of 6-bromo-2-[1H]-quinolone-3-carboxylic acid (3.4 g) in phosphorous oxychloride (40 cm³) was heated under reflux for 2 hours. The mixture was cooled, evaporated to dryness in vacuo and the solid residue was treated at 0° with methanol (50 cm³). After stirring for two hours at room temperature the mixture was filtered and the solid was washed with methanol to afford 6-bromo-2-chloro-3-methoxycarbonylquinoline, m.p. 176°–177°, (1.82 g).

Analysis %: Found: C, 44.0; H, 2.3; N, 4.7. Calculated for $C_{11}H_7CrClNO_2$: C, 44.0; H, 2.3; N, 4.7.

PREPARATION 58

6-Iodo-2-(1H)-quinolone

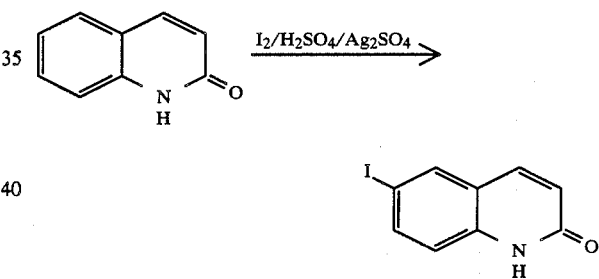

A solution of 2-[1H]-quinolone (2.0 g) and silver sulphate (2.14 g) in concentrated sulphuric acid (15.0 cm³) was stirred at room temperature during the addition of iodine (3.5 g). After heating at 50° for 24 hours the mixture was poured onto ice, the solution was neutralised with solid sodium carbonate and the solid was filtered off. This material was chromatographed on silica (Merck "MK 60.9385") eluting with chloroform to affford a residue which was recrystallised from methanol to give 6-iodo-2-[1H]-quinolone, m.p. 261°, (0.8 g).

Analysis %: Found: C, 41.0; H, 2.4; N, 5.5. Calculated for $C_9H_6INO$: C, 39.9; H, 2.2; N, 5.2.

PREPARATION 59

6-Bromo-2-chloro-8-methylquinoline

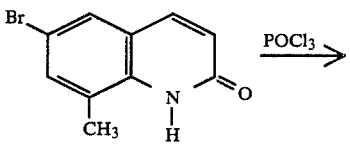

A mixture of 6-bromo-8-methyl-2-(1H)-quinolone (12.0 g) in phosphorus oxychloride (100 cm$^3$) was heated under reflux for 2 hours. Volatile material was removed in vacuo, the residue dissolved in chloroform (200 cm$^3$), and the resulting solution was poured onto ice (200 g). The mixture was basified with aqueous ammonia solution (S.G. 0.88) to pH10 and the aqueous phase was further extracted with chloroform (2×100 cm$^3$). The combined and dried (MgSO$_4$) extracts were concentrated in vacuo to give a solid (10.7 g) which was recrystallised from ethanol to afford 6-bromo-2-chloro-8-methyl-quinoline, m.p. 114°-116°.

Analysis %: Found: C, 47.2; H, 2.7; N, 5.8; Calculated for C$_{10}$H$_7$BrClN: C, 46.8; H, 2.7; N, 5.5.

PREPARATIONS 60-65

The following compounds were prepared similarly to the method of the previous Preparation using a 1.0:1.7 mixture of 5-bromo-2-(1H)-quinolone and 7-bromo-2-(1H)-quinolone (in Preparation 60 and 61) and a 1.0:2.3 mixture of 6-bromo-5-methyl-2-(1H)-quinolone and 6-bromo-7-methyl-2-(1H)-quinolone (in Preparation 62), 6-iodo-8-ethyl-2-(1H)-quinolone (in Preparation 63), 6-iodo-8-[prop-2-yl]-2-(1H)-quinolone (in Preparation 64), and 6-bromo-8-methoxy-2-(1H)-quinolone (in Preparation 65), and phosphorus oxychloride as the starting materials:

Analysis %: Found: C, 48.3; H, 3.3; N, 5.3; Calculated for C$_{11}$H$_9$BrClN: C, 48.3; H, 3.3; N, 5.2.

PREPARATION 67

6-Bromo-8-methyl-2-(1H)-quinolone

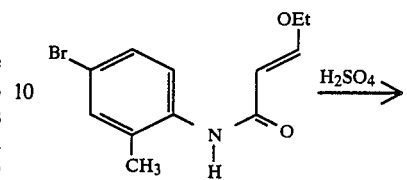

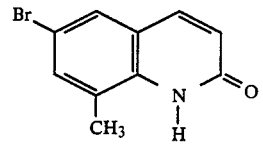

Trans-N-(4-bromo-2-methylphenyl)-3-ethoxy-propenamide (2.0 g) was added portionwise with stirring to 98% sulphuric acid (15 cm$^3$) at room temperature. After 16 hours the solution was poured onto ice (100 cm$^3$) and the resulting precipitate was filtered off and dried (1.5 g). Recrystallisation from ethyl acetate-methanol afforded 6-bromo-8-methyl-2-(1H)-quinolone, m.p. 272°-274°.

Analysis %: Found: C, 50.4; H, 3.4; N, 6.1; Calculated for C$_{10}$H$_8$NOBr: C, 50.4; H, 3.4; N, 5.9.

PREPARATION 68-75

The following compounds were prepared similarly to the method of the previous Preparation using trans-N-

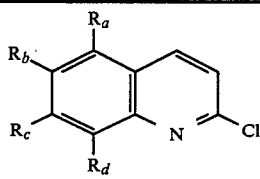

| Preparation No. | R$_a$ | R$_b$ | R$_c$ | R$_d$ | Form isolated and m.p. (°C.) | C | H | N |
|---|---|---|---|---|---|---|---|---|
| 60* | —Br | —H | —H | —H | Free base, 76-78° | 44.9 (44.6 | 2.3 2.1 | 5.8 5.8) |
| 61* | —H | —H | —Br | —H | Free base, 115-116° | 44.9 (44.6 | 2.3 2.1 | 5.8 5.8) |
| 62** | —H | —Br | —CH$_3$ | —H | Free base 121-123° | 46.7 (46.8 | 2.7 2.7 | 5.9 5.5) |
| 63 | —H | —I | —H | —Et | Free base, 75-76° | 41.6 (41.6 | 2.9 2.9 | 4.7 4.4) |
| 64 | —H | —I | —H | —CH(CH$_3$)$_2$ | Crude free base, oil | Characterised by $^1$H N.m.r. and Mass Spectroscopy | | |
| 65 | —H | —Br | —H | —OCH$_3$ | Free base, 160° | 44.0 (44.1 | 2.5 2.6 | 5.1 5.1) |

*The products of Preparations 60 and 61 were separated by HPLC on a Waters "Prep-Pak" (Trade Mark) silica column (5.7 × 30 cm) eluting with hexane:ether, 4:1.
**The product of Preparation 62 was separated from the isomeric 6-bromo-2-chloro-5-methylquinoline by crystallisation from ether.

PREPARATION 66

6-Bromo-2-chloro-4,8-dimethylquinoline, m.p. 182°, was prepared similarly to Preparation 59, using 6-bromo-4,8-dimethyl-2-(1H)-quinolone and phosphorus oxychloride as the starting materials.

(3-bromophenyl)-3-ethoxypropenamide (in Preparations 68 and 69), trans-N-(4-bromo-3-methylphenyl)-3-ethoxy-propenamide (in Preparations 70 and 71), trans-N-(4-iodophenyl)-3-ethoxypropenamide (in Preparation 72), trans-N-(4-iodo-2-ethylphenyl)-3-ethoxypropenamide (in Preparation 73), trans-N-(4-iodo-2-[prop-2-yl]-phenyl)-3-ethoxypropenamide (in Preparation 74), and trans-N-(4-bromo-2-methoxyphenyl)-3-ethoxypropenamide (in Preparation 75) and 98% sulphuric acid as the starting materials:

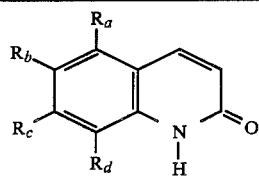

| Preparation No. | $R_a$ | $R_b$ | $R_c$ | $R_d$ | Form isolated and m.p. (°C.) | | Analysis % (Theoretical in brackets) | | |
|---|---|---|---|---|---|---|---|---|---|
| | | | | | | | C | H | N |
| 68 | —Br | —H | —H | —H | ⎫ 1.0 ⎫ | mixture of | 48.2 | 2.8 | 6.4 |
| 69 | —H | —H | —Br | —H | ⎬ to ⎬ | isomers* m.p. 251–260° | (48.2 | 2.7 | 6.3) |
| 70 | —CH₃ | —Br | —H | —H | ⎫ 1.0 ⎫ | mixture of | | | |
| 71 | —H | —Br | —CH₃ | —H | ⎬ to ⎬ 2.3 | isomers* | | | |
| 72+ | —H | —I | —H | —H | | Free base, 260–263° | 40.0 (39.9 | 2.2 2.2 | 5.1 5.2) |
| 73 | —H | —I | —H | —Et | | Free base, 236.5–239° | 44.2 (44.2 | 3.4 3.4 | 4.8 4.7) |
| 74 | —H | —I | —H | —CH(CH₃)₂ | | Free base, 189–192° | 46.2 (46.0 | 3.9 3.9 | 4.6 4.5) |
| 75 | —H | —Br | —H | —OCH₃ | | Free base, 167–170° | 47.1 (47.3 | 3.2 3.2 | 5.3 5.5) |

*Ratio estimated by 250 MHz ¹H N.M.R.
+Alternative to Preparation 58.
6-Iodo-4-methyl-2-(1H)—quinolone is a known compound.

PREPARATION 76

6-Bromo-4,8-dimethyl-2-(1H)-quinolone

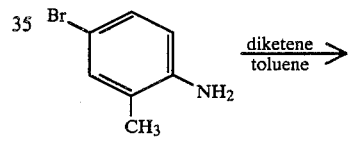

N-[4-Bromo-2-methylphenyl]-acetoacetamide (18 g) was heated for 5 hours with stirring in 98% sulphuric acid (50 cm³) at 100°. The cooled mixture was then poured onto ice (200 g), the solid was filtered off and dried in vacuo at 100° for 2 hours to give the crude product (15.0 g). A small portion (1.5 g) of this material was recrystallised from ethyl acetate/methanol to afford 6-bromo-4,8-dimethyl-2-(1H)-quinolone, m.p. >300° (1.1 g).

Analysis %: Found: C, 52.0; H, 4.1; N, 5.5; Calculated for C₁₁H₁₀BrNO: C, 52.4; H, 4.0; N, 5.6.

PREPARATION 77

N-[4-Bromo-2-methylphenyl]-acetoacetamide

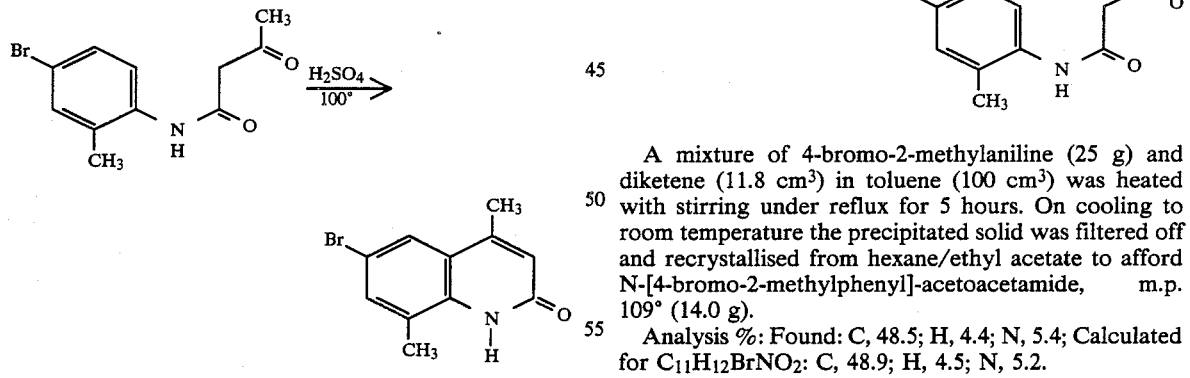

A mixture of 4-bromo-2-methylaniline (25 g) and diketene (11.8 cm³) in toluene (100 cm³) was heated with stirring under reflux for 5 hours. On cooling to room temperature the precipitated solid was filtered off and recrystallised from hexane/ethyl acetate to afford N-[4-bromo-2-methylphenyl]-acetoacetamide, m.p. 109° (14.0 g).

Analysis %: Found: C, 48.5; H, 4.4; N, 5.4; Calculated for C₁₁H₁₂BrNO₂: C, 48.9; H, 4.5; N, 5.2.

PREPARATION 78

Trans-N-(4-Bromo-2-methylphenyl)-3-ethoxypropenamide

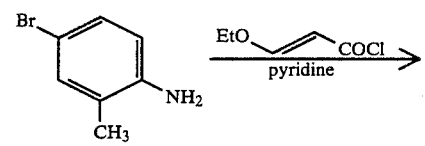

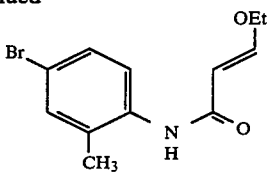

Trans-3-Ethoxypropenoyl chloride (0.74 g) was added at 0° to a stirred solution of 4-bromo-2-methylaniline (0.93 g) in pyridine (10 cm³). After 0.5 hours water (40 cm³) was added, the solid material was filtered off, washed with water (30 cm³) and dried. The product was recrystallised from ethyl acetate to afford trans-N-(4-bromo-2-methylphenyl)-3-ethoxypropenamide, m.p. 163°–164°, (1.3 g).

Analysis %: Found: C, 50.7; H, 5.0; N, 5.1; Calculated for $C_{12}H_{14}NO_2Br$: C, 50.7; H, 5.0; N, 4.9.

PREPARATIONS 79–85

The following compounds were prepared similarly to the method of the previous Preparation using the appropriately substituted aniline and trans-3-ethoxypropenoyl chloride as starting materials:

(27.0 g) and sodium acetate (16.4 g) in acetic acid (250 cm³). After 1 hour, volatile material was removed in vacuo and the residue was partitioned between ethyl acetate (200 cm³) and 10% sodium carbonate solution (50 cm³). The dried (MgSO₄) organic extract was filtered and evaporated in vacuo to afford an oil which was chromatographed on silica (Merck "MK 60.9385") eluting with hexane. Combination and evaporation of the product containing fractions gave the product as a crude dark unstable oil (38 g) which was not characterised fully but was used directly in Preparation 84.

PREPARATION 87

4-Iodo-2-ethylaniline (crude oil) was prepared similarly to the previous Preparation using 2-ethylaniline as the starting material. (4-Bromo-2-methoxyaniline is a known compound.)

PREPARATION 88

6-Cyano-2-methoxyquinoline

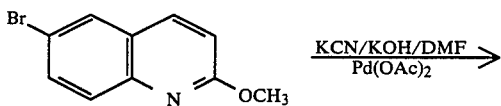

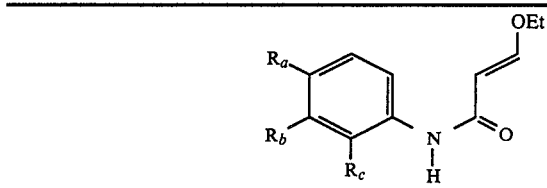

| Preparation No. | $R_a$ | $R_b$ | $R_c$ | Form isolated and m.p. (°C.) | Analysis % (Theoretical in brackets) C | H | N |
|---|---|---|---|---|---|---|---|
| 79 | —Br | —CH₃ | —H | Free base, 112–115° | 50.7 (50.7 | 5.0 5.0 | 5.0 4.9) |
| 80 | —H | —Br | —H | Free base, 98–100° | 49.3 (48.9 | 4.7 4.5 | 5.4 5.2) |
| 81 | —I | —H | —H | Free base as a crude solid, 181–182° | — | — | — |
| 82 | (pyridyl-CH₂) | —H | —H | Free base, 201–204° | 71.3 (71.6 | 6.1 6.0 | 10.4 10.4) |
| 83 | —I | —H | —Et | Free base, 196.5–199° | 45.2 (45.2 | 4.6 4.7 | 4.1 4.1) |
| 84 | —I | —H | —CH(CH₃)₂ | Free base, 161–163° | 47.2 (46.8 | 5.1 5.1 | 4.1 3.9) |
| 85 | —Br | —H | —OCH₃ | Free base, 133–136° | 48.4 (48.0 | 4.8 4.7 | 4.8 4.7) |

PREPARATION 86

4-Iodo-2-[prop-2-yl]aniline

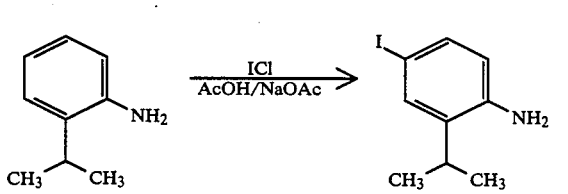

Iodine monochloride (12.9 cm³) was added at room temperature to a stirred solution of 2-[prop-2-yl]-aniline A mixture of 6-bromo-2-methoxyquinoline (0.476 g), potassium cyanide (0.26 g), potassium hydroxide (0.05 mg) and palladium (II) acetate (0.067 g) in DMF (2.0 cm³) were heated at 135° for 3 hours. The cooled solution was then partitioned between water (20 cm³) and chloroform (50 cm³) and the aqueous phase was further extracted with chloroform (2×25 cm³). The combined and dried (MgSO₄) extracts were evaporated in vacuo and the residue was chromatographed on silica (Merck "MK 60.9385") eluting with toluene to afford, after collection and evaporation of appropriate fractions, 6-cyano-2-methoxyquinoline, m.p. 163°–165°, (0.216 g).

Analysis %: Found: C, 71.7; H, 4.4; N, 14.8; Calculated for $C_{11}H_8N_2O$: C, 71.4; H, 4.4; N, 15.2.

PREPARATION 89

2-Methoxy-6-(1-tributylstannyl-(1H)-tetrazol-5-yl)quinoline

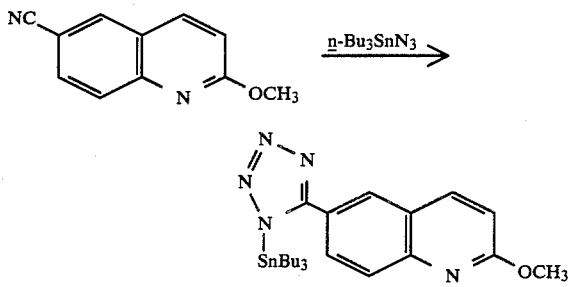

6-Cyano-2-methoxyquinoline (0.368 g) and tri-n-butyltin azide (0.73 g) were heated together at 110° for 18 hours to afford 2-methoxy-6-(1-tributylstannyl-(1H)-tetrazol-5-yl)quinoline as a crude oil which was not purified further but was used directly in the preparation of 6-(tetrazol-5-yl)-2-(1H)-quinolone (see Example 43).

PREPARATION 90

2-Methoxy-6-(1-butyl-(1H)-tetrazol-5-yl)quinoline and 2-methoxy-6-(2-butyl-(2H)-tetrazol-5-yl)quinoline

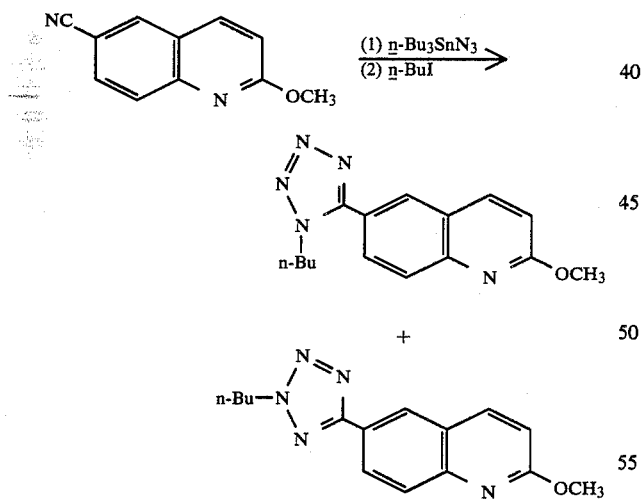

6-Cyano-2-methoxyquinoline (0.368 g) and tri-n-butyltin azide (0.73 g) were heated together at 120° for 18 hours. The mixture was then cooled to 100°, n-butyliodide (0.42 g) was added, and the reaction mixture was stirred for 3 hours. The residue was partitioned between acetonitrile (20 cm³) and hexane (20 cm³) and the acetonitrile layer was concentrated in vacuo to afford an oil. Chromatography of the oil on silica (Merck MK 60.9385) eluting with dichloromethane gave firstly; (R$_F$ 0.75 in chloroform: methanol, 19:1) 2-methoxy-6-(2-butyl-(2H)-tetrazol-5-yl)quinoline as a crude oil (0.087 g) and secondly; (R$_F$ 0.62 in chloroform:methanol, 19:1) 2-methoxy-6-(1-butyl-(1H)-tetrazol-5-yl)-quinoline as a crude oil (0.30 g). These compounds were used directly without further purification in Examples 44 and 45.

PREPARATION 91

6-Bromo-4-methyl-3,4-dihydro-2-(1H)-quinolone

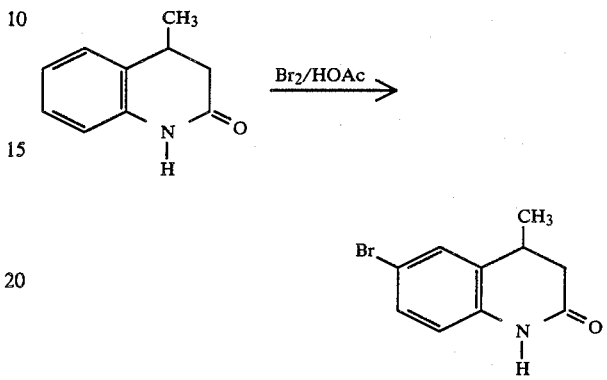

A solution of bromine (0.08 cm³) in acetic acid (1 cm³) was added at room temperature to a stirred solution of 4-methyl-3,4-dihydro-2-(1H)-quinolone (0.5 g) in acetic acid (4.0 cm³). After 2 hours, volatile material was removed in vacuo, the residue was partitioned between chloroform (50 cm³) and water (20 cm³), and the organic phase was further extracted with chloroform (2×20 cm³). The combined and dried (MgSO₄) organic extracts were evaporated in vacuo and the solid residue was recrystallised from ethyl acetate to afford 6-bromo-4-methyl-3,4-dihydro-2-(1H)-quinolone, m.p. 190°, (0.35 g).

Analysis %: Found: C, 50.2; H, 4.2; N, 6.0; Calculated for $C_{10}H_{10}BrNO$: C, 50.0; H, 4.2; N, 5.8.

6-Bromo-3,4-dihydro-2-(1H)-quinolone is a known compound.

PREPARATION 92

6-Iodo-3-nitro-2-(1H)-quinolone

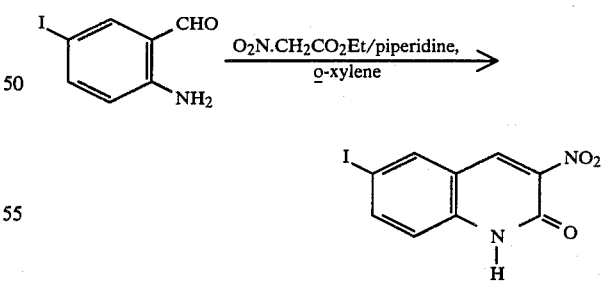

A stirred mixture of 2-amino-5-iodobenzaldehyde (2.0 g), ethyl nitroacetate (4.2 g), and piperidine (0.7 g) was heated under reflux for 1.5 hours in o-xylene (100 cm³). The cooled solution was then concentrated in vacuo and the solid residue was recrystallised from chloroform-isopropanol to afford 6-iodo-3-nitro-2-(1H)-quinolone, m.p. 279°–282°, (1.14 g).

Analysis %: Found: C, 34.6; H, 1.7; N, 8.6 Calculated for $C_9H_5IN_2O_3$: C, 34.2; H, 1.6; N, 8.9.

PREPARATION 93

2-Amino-5-iodobenzaldehyde hemihydrate

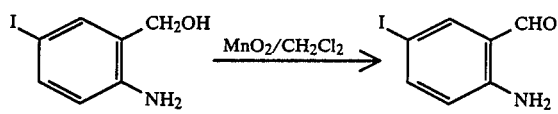

Manganese dioxide (0.044 g) was added to a stirred solution of 2-amino-5-iodobenzyl alcohol (0.125 g) in dichloromethane (10 cm$^3$) and the mixture was stirred for 6 hours. A further portion of manganese dioxide (0.044 g) was then added and stirring was continued for 16 hours. The mixture was then filtered, the filtrate evaporated in vacuo, and the residue chromatographed on silica (Merck "MK 60.9385") eluting with ethyl acetate. The requisite fractions were combined and concentrated in vacuo to afford 2-amino-5-iodobenzaldehyde. 0.5H$_2$O as a solid, m.p. 105°, (0.1 g).

Analysis %: Found: C, 33.0; H, 2.4; N, 6.1; Calculated for C$_7$H$_6$INO.0.5H$_2$O: C, 32.8; H, 2.5; N, 5.5.

PREPARATION 94

2-Amino-5-iodobenzyl alcohol

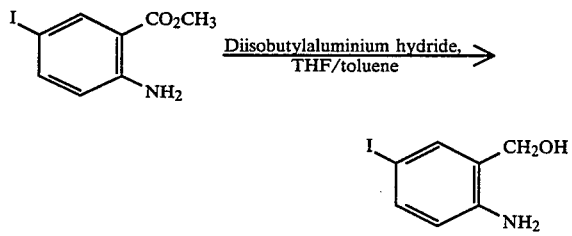

A solution of diisobutylaluminium hydride (210 cm$^3$ of a 1.5M solution in THF) was added at −30° to a stirred solution of methyl-2-amino-5-iodobenzoate (28.0 g) in THF (100 cm$^3$) under nitrogen. The mixture was warmed to room temperature, stirred for 16 hours and treated with methanol (35 cm$^3$). Ethyl acetate (500 cm$^3$) was added and the mixture filtered to remove inorganic material. The filtrate was concentrated in vacuo to afford a solid which was chromatographed on silica (Merck "MK 60.9385") eluting wiht chloroform:methanol, 49:1 (by volume), and the requisite fractions were combined and evaporated in vacuo to give 2-amino-5-iodobenzyl alcohol, m.p. 125°, (19.0 g).

Analysis %: Found: C, 34.4; H, 3.2; N, 6.0; Calculated for C$_{17}$H$_8$INO: C, 33.8; H, 3.2; N, 5.6.

PREPARATION 95

2-Methoxyquinoline-6-carboxylic acid

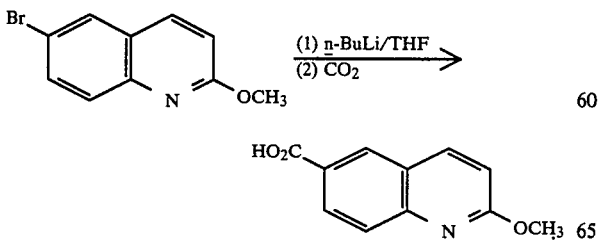

n-Butyl lithium (63 cm$^3$ of a 1.6M solution in hexane) was added dropwise to a stirred solution of 6-bromo-2-methoxyquinoline (20 g) in THF (250 cm$^3$) at −70° under nitrogen. After 0.5 hours, solid carbon dioxide (50 g) was added, the solution was allowed to warm to room temperature, and volatile material was removed in vacuo. The residue was partitioned between dichloromethane (100 cm$^3$) and water (100 cm$^3$), the aqueous phase was separated and acidified to pH 3.5 with 5M hydrochloric acid. The precipitated solid was filtered and dried (14.2 g). Recrystallisation of a small portion from isopropanol afforded 2-methoxyquinoline-6-carboxylic acid, m.p. 220°-222°.

Analysis %: Found: C, 65.1; H, 4.5; N, 7.0; Calculated for C$_{11}$H$_9$NO$_3$: C, 65.0; H, 4.5; N, 6.9.

PREPARATIONS 96-100

The following compounds were prepared similarly to the previous Preparation starting from the appropriately substituted 6-bromo- or 6-iodo-2-methoxyquinoline, n-BuLi and CO$_2$:

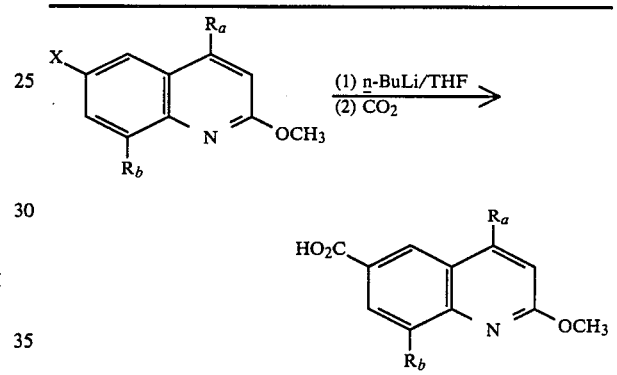

| Preparation No. | X | $R_a$ | $R_b$ | Form isolated and m.p. (°C.) | Analysis % (Theoretical in brackets) C | H | N |
|---|---|---|---|---|---|---|---|
| 96 | —Br | —H | —CH$_3$ | Free acid, 268–270° | 66.2 (66.3) | 5.1 (5.1) | 6.4 (6.4) |
| 97 | —I | —H | —Et | Free acid, 239° | 67.8 (67.5) | 5.7 (5.7) | 6.0 (6.1) |
| 98 | —I | —H | —CH(CH$_3$)$_2$ | Free acid, 259–262° | 68.7 (68.6) | 6.2 (6.2) | 5.5 (5.7) |
| 99 | —Br | —H | —OCH$_3$ | Free acid, 0.25 H$_2$O, 253.5–254.50° | 60.7 (60.6) | 4.8 (4.9) | 6.0 (5.9) |
| 100 | —Br | —CH$_3$ | —CH$_3$ | Free acid, 0.5 H$_2$O, 284° | 64.6 (65.0) | 5.6 (5.9) | 5.7 (5.8) |

PREPARATION 101

2-Methoxyquinoline-6-carboxylic acid amide

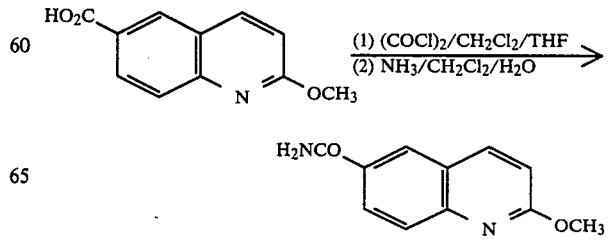

Oxalyl chloride (10.3 cm³) was added dropwise to a stirred solution of 2-methoxyquinoline-6-carboxylic acid (12.0 g) in dichloromethane (100 cm³) and DMF (0.1 g) at 0°. The mixture was warmed to room temperature and after 2 hours volatile material was removed in vacuo. The residue was taken into dichloromethane (100 cm³), cooled to 0° and treated cautiously with aqueous ammonia solution (30 cm³ of S.G. 0.880). After 2 hours the mixture was concentrated in vacuo and the solid residue was recrystallised from isopropanol to afford 2-methoxyquinoline-6-carboxylic acid amide, m.p. 212°–214°, (7.9 g).

Analysis %: Found: C, 65.0; H, 5.0; N, 13.8; Calculated for $C_{11}H_{10}N_2O_2$: C, 65.3; H, 5.0; N, 13.9.

PREPARATIONS 102–106

The following compounds were prepared similarly to the previous preparation starting from oxalyl chloride, the appropriately substituted 2-methoxyquinoline-6-carboxylic acid, and ammonia:

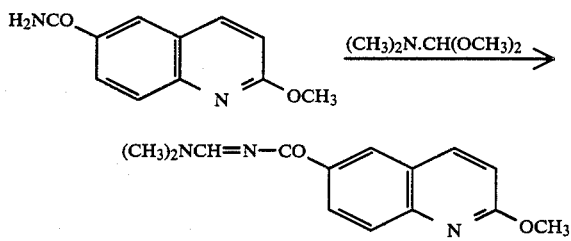

| Preparation No. | $R_a$ | $R_b$ | Form isolated and m.p. (°C.) | Analysis % (Theoretical in brackets) | | |
|---|---|---|---|---|---|---|
| | | | | C | H | N |
| 102 | —H | —CH₃ | Free base, 1/6 H₂O 212–215° | 65.5 (65.7 | 5.5 5.6 | 13.2 12.8) |
| 103 | —H | —Et | Free base, 170–175° | 67.7 (67.8 | 6.2 6.1 | 12.3 12.2) |
| 104 | —H | —CH(CH₃)₂ | Free base, 184–186° | 68.7 (68.8 | 6.6 6.6 | 11.7 11.5) |
| 105 | —H | —OCH₃ | Free base 0.25 H₂O, 214.5–216.5° | 61.2 (60.9 | 5.2 5.3 | 12.0 11.8) |
| 106 | —CH₃ | —CH₃ | Free base monohydrate, 262.5° | 63.4 (63.0 | 5.7 6.5 | 11.0 11.3) |

PREPARATION 107

2-Methoxyquinoline-6-(N-[dimethylaminomethylene])-carboxylic acid amide

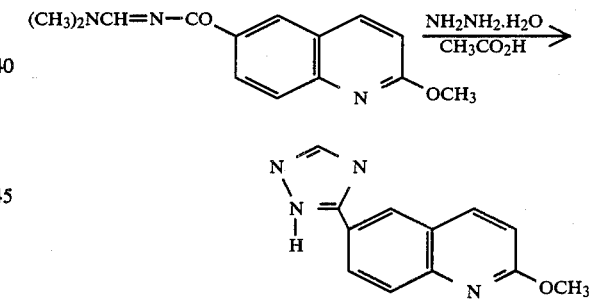

A mixture of 2-methoxyquinoline-6-carboxylic acid amide (3.0 g) and N,N-dimethylformamide dimethylacetal (6.0 cm³) was heated at 120° for 1.5 hours. After standing at room temperature for 16 hours the crystalline product was filtered off, washed with hexane (10 cm³) and dried to afford 2-methoxyquinoline-6-(N-[dimethylaminomethylene])carboxylic acid amide, m.p. 192°–195°, (3.78 g).

Analysis %: Found: C, 65.0; H, 5.9; N, 16.2; Calculated for $C_{14}H_{15}N_3O_2$: C, 65.4; H, 5.8; N, 16.3.

PREPARATIONS 108–112

The following compounds were prepared similarly to the previous Preparation starting from the appropriately substituted 2-methoxyquinoline-6-carboxylic acid amide and N,N-dimethylformamide dimethylacetal:

| Preparation No. | $R_a$ | $R_b$ | Form isolated and m.p. (°C.) | Analysis % (Theoretical in brackets) | | |
|---|---|---|---|---|---|---|
| | | | | C | H | N |
| 108 | —H | —CH₃ | Free base, 180–182° | 66.0 (66.4 | 6.3 6.3 | 15.8 15.5) |
| 109 | —H | —Et | Free base, 163–164° | 67.7 (67.4 | 6.9 6.7 | 14.6 14.7) |
| 110 | —H | —CH(CH₃)₂ | Free base, 156–159° | 68.2 (68.2 | 7.3 7.1 | 14.2 14.0) |
| 111 | —H | —OCH₃ | Free base 0.25 H₂O, 187.5–189.5° | 62.1 (61.7 | 5.9 6.0 | 14.5 14.4) |
| 112 | —CH₃ | —CH₃ | Free base 0.25 H₂O, 154° | 65.9 (66.3 | 6.7 6.8 | 14.0 14.5) |

PREPARATION 113

2-Methoxy-6-[(1H)-1,2,4-triazol-5-yl]quinoline

A mixture of 2-methoxyquinoline-6-(N-[dimethylaminomethylene])carboxylic acid amide (1.0 g) and hydrazine hydrate (0.208 cm³) was stirred at 90° for 1.5 hours in glacial acetic acid (10 cm³). Volatile material was removed in vacuo, the residue was chromatographed on silica (Merck "MK 60.9385") eluting with ethyl acetate:methanol, 49:1 (by volume), and the requisite fractions were combined and evaporated to afford 2-methoxy-6-[(1H)-1,2,4-triazol-5-yl]quinoline, m.p. 198°–200°, (0.811 g).

Analysis %: Found: C, 63.8; H, 4.5; N, 24.8; Calculated for $C_{12}H_{10}N_4O$: C, 63.7; H, 4.4; N, 24.8.

PREPARATIONS 114–122

The following compounds were prepared similarly to the previous Preparation starting from the appropriately substituted 2-methoxyquinoline-6-(N-[dimethylaminomethylene])carboxylic acid amide and hydrazine hydrate (in Preparation 114) or methylhydrazine (in Preparations 115-122) (Preparation 116). The minor isomer, $R_f$ 0.28 in ethyl acetate, was eluted subsequently (Preparation 117).

Reaction scheme: starting material with $(CH_3)_2NCH=N-$ amide group on quinoline bearing $R_a$, $R_b$ and $-OCH_3$ substituents, treated with $H_2NNH_2$ or $CH_3NHNH_2$ / AcOH, gives product with $R_a$, $R_b$, $R_c$ substituents on quinoline with $-OCH_3$.

| Preparation No. | $R_a$ | $R_b$ | $R_c$ | Form isolated and m.p. (°C.) | Analysis % (Theoretical in brackets) C | H | N |
|---|---|---|---|---|---|---|---|
| 114 | —H | —CH$_3$ | 1H-1,2,4-triazol-3-yl (NH) | Free base, 226–229° | 65.1 (65.0 | 5.1 5.0 | 23.5 23.3) |
| 115 | —H | —H | 1-methyl-1,2,4-triazol-3-yl | Free base, 149–152° | 65.1 (65.0 | 5.0 5.0 | 23.1 23.3) |
| 116 | —H | —CH$_3$ | 1-methyl-1,2,4-triazol-3-yl | Free base, 151–153° | 66.4 (66.1 | 5.6 5.5 | 22.3 22.0) |
| 117 | —H | —CH$_3$ | 4-methyl-1,2,4-triazol-3-yl | Free base, 174–176° | 65.9 (66.1 | 5.6 5.5 | 21.6 22.0) |
| 118 | —H | —Et | 1-methyl-1,2,4-triazol-3-yl | Free base, 74–76° | 67.0 (67.1 | 6.2 6.0 | 21.2 20.9) |
| 119 | —H | —Et | 4-methyl-1,2,4-triazol-3-yl | Free base, 95–96.5° | 67.0 (67.1 | 6.1 6.0 | 20.9 20.9) |
| 120 | —H | —CH(CH$_3$)$_2$ | 1-methyl-1,2,4-triazol-3-yl | Free base, 0.25 H$_2$O 83–86° | 67.1 (67.0 | 6.4 6.4 | 19.4 19.5) |
| 121 | —H | —OCH$_3$ | 1-methyl-1,2,4-triazol-3-yl | Free base, 0.25 H$_2$O, 104.5–107° | 61.0 (61.2 | 5.2 5.3 | 20.5 20.4) |
| 122 | —CH$_3$ | —CH$_3$ | 1-methyl-1,2,4-triazol-3-yl | Free base, 172–6° | 67.0 (67.1 | 6.1 6.0 | 20.6 20.9) |

Preparations 116 and 117 were obtained as a mixture of regioisomers which were separated by chromatography on silica (Merck "MK 60.9385") eluting with ether. The major isomer, $R_f$ 0.8 in ethyl acetate, eluted first Preparations 118 and 119 were similarly obtained as a mixture of regioisomers which were separated by chromatography on silica (Merck "MK 60.9385"). Elution with hexane:ether, 1:1, afforded the major isomer, (Preparation 118), while the minor isomer (Preparation 119) was eluted from the column with ethyl acetate.

PREPARATION 123

2-Methoxy-6-(1,2,4-oxadiazol-5-yl)quinoline

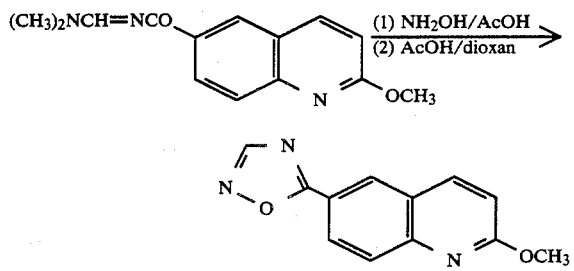

Aqueous 5M sodium hydroxide solution (0.94 cm³) was added to a solution of hydroxylamine hydrochloride (0.325 g) in water (3 cm³) and acetic acid (7 cm³). 2-Methoxyquinoline-6-N-([dimethylaminomethylene])-carboxylic acid amide (1.0 g) was added, the mixture was stirred for 10 minutes, water (10 cm³) was added, and the solution solution was kept at 0° for 1 hour. The precipitate was filtered off, taken into dioxan (5 cm³) and acetic acid (5 cm³), and warmed at 90° for 1.5 hours. The cooled solution was treated with water (10 cm³), and the precipitate was filtered off and chromatographed on silica (Merck "MK 60.9385") eluting with dichloromethane. The requisite fractions were combined and evaporated in vacuo to afford a solid (0.537 g). A small sample of the solid was recrystallised from ethyl acetate to give 2-methoxy-6-(1,2,4-oxadiazol-5-yl)quinoline, m.p. 150°-152°.

Analysis %: Found: C, 63.3; H, 4.0; N, 18.6; Calculated for $C_{12}H_9N_3O_2$: C, 63.4; H, 4.0; N, 18.5.

PREPARATION 124

6-[1-Methyl-(1H)-imidazol-2-yl]-2-methoxyquinoline

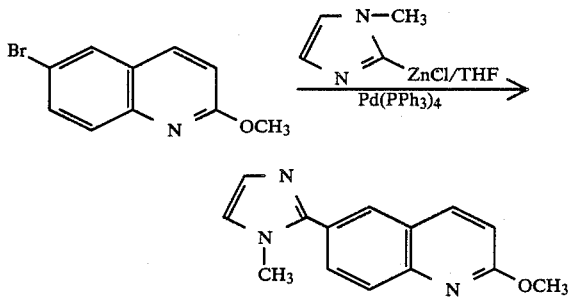

n-Butyl lithium (9 cm³ of a 1.6M solution in hexane) was added at −45° to a stirred solution of 1-methyl-(1H)-imidazole (1.03 cm³) in THF (30 cm³) under nitrogen. After 1.25 hours a solution of anhydrous zinc chloride (1.95 g) in THF (30 cm³) was added dropwise over 5 minutes giving a white precipitate. The mixture was warmed to room temperature, a solution of 6-bromo-2-methoxyquinoline (3 g) and tetrakis (triphenylphosphine) palladium(O) (0.2 g) in THF (20 cm³) was added, and the solution was heated under reflux for 16 hours. Saturated ammonium chloride (2 cm³) was added, the reaction mixture was concentrated in vacuo, and the residue partitioned between chloroform (100 cm³) and a solution of ethylenediaminetetraacetic acid disodium salt (10 g) in water (100 cm³). The aqueous phase was extracted further with chloroform (2×50 cm³) and the combined and dried (MgSO₄) extracts were evaporated in vacuo to give a solid, which was chromatographed on silica (Merck "MK 60.9385"), eluting with chloroform:methanol, 19:1 (by volume). The requisite fractions were combined and evaporated in vacuo to afford a foam which was recrystallised from ethyl acetate-hexane to give 6-[1-methyl-(1H)-imidazol-2-yl]-2-methoxyquinoline, m.p. 116.5°-118.5°, (0.517 g).

Analysis %: Found: C, 70.3; H, 5.5; N, 17.4; Calculated for $C_{14}H_{13}N_3O$: C, 70.3; H, 5.5; N, 17.5.

PREPARATION 125

Also synthesised by a similar method to the previous preparation using 1-methyl-(1H)-imidazole, tetrakis (triphenylphosphine)palladium(O) and 6-bromo-2-methoxy-8-methylquinoline as starting materials was 6-(1-methyl-(1H)-imidazol-2-yl)-2-methoxy-8-methylquinoline hemihydrate, m.p. 158°-161°.

Analysis %: Found: C, 68.4; H, 5.8; N, 15.8; Calculated for $C_{15}H_{15}N_3O.\frac{1}{2}H_2O$: C, 68.7; H, 6.1; N, 16.0.

PREPARATION 126

6-[1-Methyl-(1H)-imidazol-5-yl]-2-methoxy-8-methylquinoline

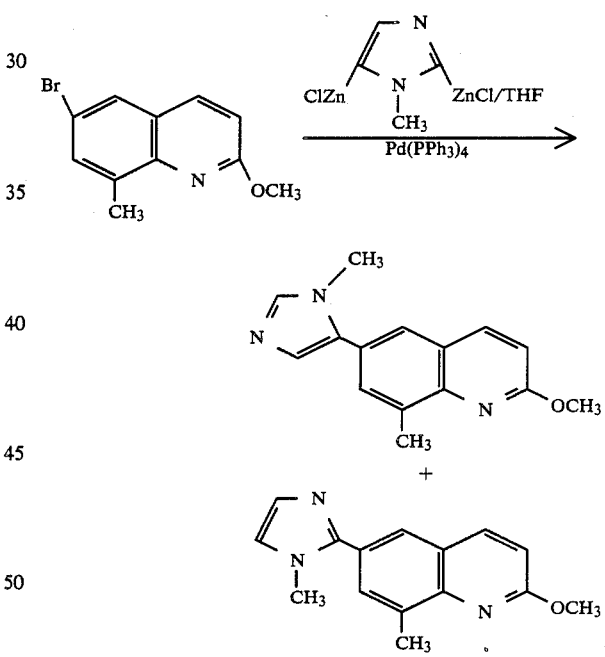

t-Butyllithium (11.9 cm³ of a 2.0M solution in pentane) was added at −70° under nitrogen to a stirred solution of 1-methyl-(1H)-imidazole (0.95 cm³) in THF (8 cm³). After 10 minutes, the mixture was warmed to 0° and stirring was continued for 1 hour. A solution of anhydrous zinc chloride (6.25 g) in THF (45 cm³) was then added and the mixture was stirred for a further 1 hour. 6-Bromo-2-methoxy-8-methylquinoline (1.0 g) and tetrakis (triphenylphosphine) palladium (0) (0.04 g) were added and the mixture was heated under reflux for 18 hours. The cooled mixture was concentrated in vacuo and partitioned between chloroform (200 cm³) and a solution of ethylenediaminetetraacetic acid disodium salt (50 g) in water (250 cm³). The aqueous phase was further extracted with chloroform (2×100 cm³) and the combined and dried (MgSO₄) extracts were evaporated to give a solid which was chromatographed on silica (Merck "MK 60.9385") eluting with chloroform. After combination and evaporation of appropriate fractions, this afforded firstly; ($R_f$ 0.32 in chloroform) 6-[1-methyl-(1H)-imidazol-2-yl]-2-methoxy-8-methylquinoline, m.p. 160°–162° (0.37 g), identical to the product of Preparation 125; and secondly ($R_f$ 0.26 in chloroform) 6-(1-methyl-(1H)-imidazol-5-yl]-2-methoxy-8-methyl-quinoline, m.p. 174°–175°, (0.05 g).

Analysis 5: Found: C, 71.2; H, 6.0; N, 16.2; Calculated for $C_{15}H_{15}N_3$: C, 71.1; H, 6.0; N, 16.6.

We claim:

1. A heterocyclic-substituted 2-quinolone compound of the formula:

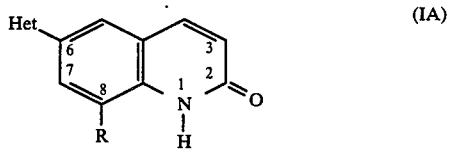

(IA)

or a pharmaceutically-acceptable salt thereof, wherein "Het" is pyridyl or triazolyl, optionally substituted by 1 or 2 substitutents each selected from $C_1$–$C_4$ alkyl, $C_1$–$C_4$ alkoxy, cyano, amino and carbamoyl, said "Het" group being attached by a carbon atom to the 6-position of the quinolone nucleus; and R, which is attached to the 8-position, is hydrogen, $C_1$–$C_4$ alkyl, $C_1$–$C_4$ alkoxy, $C_1$–$C_4$ alkylthio, $C_1$–$C_4$ alkylsulphinyl, $C_1$–$C_4$ alkylsulphonyl, halo, $CF_3$, hydroxy, hydroxymethyl, or cyano.

2. A compound as claimed in claim 1, wherein "Het" is 2,6-dimethylpyrid-3-yl or 1-methyl-(H)-1,2,4-triazol-5-yl.

3. A compound as claimed in claim 2, wherein R is 8-methyl.

4. A compound as claimed in claim 3, wherein "Het" is 2,6-dimethylpyrid-3-yl and which is in the form of a sodium salt.

5. A pharmaceutical cardiac composition stimulant comprising a compound as claimed in claim 1, or a pharmaceutically acceptable salt thereof, together with a pharmaceutically acceptable diluent or carrier.

6. A method for the treatment of congestive heart failure in a patient which comprises administering to the patient a cardiac stimulating effective amount of a compound of the formula (IA) as claimed in claim 1, or a pharmaceutically acceptable salt thereof.

* * * * *